(12) United States Patent
Kim et al.

(10) Patent No.: US 9,968,651 B2
(45) Date of Patent: May 15, 2018

(54) NERVE REGENERATING OR NERVE GROWTH-PROMOTING PHARMACEUTICAL COMPOSITION CONTAINING VAX PROTEIN AS ACTIVE INGREDIENT

(71) Applicant: KOREA ADVANCED INSTITUTE OF SCIENCE AND TECHNOLOGY, Daejeon (KR)

(72) Inventors: Jin Woo Kim, Daejeon (KR); Nam-Suk Kim, Daejeon (KR)

(73) Assignee: Korea Advanced Institute of Science and Technology, Daejeon (KR)

( * ) Notice: Subject to any disclaimer, the term of this patent is extended or adjusted under 35 U.S.C. 154(b) by 0 days. days.

(21) Appl. No.: 15/159,739

(22) Filed: May 19, 2016

(65) Prior Publication Data

US 2016/0250288 A1  Sep. 1, 2016

Related U.S. Application Data

(63) Continuation of application No. PCT/KR2014/011208, filed on Nov. 20, 2014.

(30) Foreign Application Priority Data

Nov. 20, 2013 (KR) .......................... 10-2013-0141193
Nov. 14, 2014 (KR) .......................... 10-2014-0158645

(51) Int. Cl.
| | | |
|---|---|---|
| *A61K 38/17* | (2006.01) | |
| *A61K 48/00* | (2006.01) | |
| *G01N 33/50* | (2006.01) | |
| *A61K 35/30* | (2015.01) | |

(52) U.S. Cl.
CPC .......... *A61K 38/1709* (2013.01); *A61K 48/00* (2013.01); *G01N 33/5058* (2013.01); *A61K 35/30* (2013.01)

(58) Field of Classification Search
CPC ..... A61K 38/18; A61K 38/1709; A61K 35/30
See application file for complete search history.

(56) References Cited

PUBLICATIONS

Jackowski, British J. of Neurosurgery 9 (1995): 303-317.*
Mui et al., "Vax genes ventralize the embryonic eye," *Genes & Development* 19: 1249-1259 (2005).
Vacik et al., "A novel mechanism for the transcriptional regulation of Wnt signaling in development," *Genes & Development* 25:1783-1795 (2011).
Barbieri et al., "Vax2 inactivation in mouse determines alteration of the eye dorsal-ventral axis, misrouting of the optic fibres and eye coloboma," *Development* 129: 805-813 (2002).
Bertuzzi et al., "The homeodomain protein Vax1 is required for axon guidance and major tract formation in the developing forebrain," *Genes and Development* 13: 3092-3105 (1999).
Fuerst et al., "Defects in eye development in transgenic mice overexpressing the heparin sulfate proteoglycan agrin," *Developmental Biology* 303: 165-180 (available online Dec. 2, 2006).
Hallonet et al., "Vax1, a novel homeobox-containing gene, directs development of the basal forebrain and visual system," *Genes and Development* 13: 3106-3114 (1999).
NCBI Reference Sequence NP_033527.1 "ventral anterior homeobox 1 [Mus musculus]" http://www.ncbi.nlm.nih.gov/protein/6678557?sat=18&satkey=28550, 2 pages (Oct. 26, 2013).
NCBI Reference Sequence NP_036042.1 "ventral anterior homeobox 2 [Mus musculus]" http://www.ncbi.nlm.nih.gov/protein/6678557?sat=17&satkey=23083962, 2 pages (Jan. 13, 2013).

* cited by examiner

*Primary Examiner* — Robert C Hayes
(74) *Attorney, Agent, or Firm* — Klarquist Sparkman, LLP

(57) ABSTRACT

The present invention relates to a pharmaceutical composition for the regeneration of nerves comprising Vax protein as an active ingredient. Vax1 is secreted in the ventral hypothalamus (vHT) explant separated from a mouse. The secreted Vax1 combines with extracellular sugar group of heparan sulfate proteoglycans (HSPGs) existing in retinal ganglion cell (RGC) axon of the retinal explant co-cultured so as for the complex invades into axonplasm. Then, the Vax1 conjugated with the sugar group activates the local protein synthesis to accelerate the growth of retinal ganglion cell axon. In some embodiments, Vax protein or a nucleic acid encoding the protein, can be used in a pharmaceutical composition for the regeneration of nerves.

3 Claims, 59 Drawing Sheets

[Figure 1a]
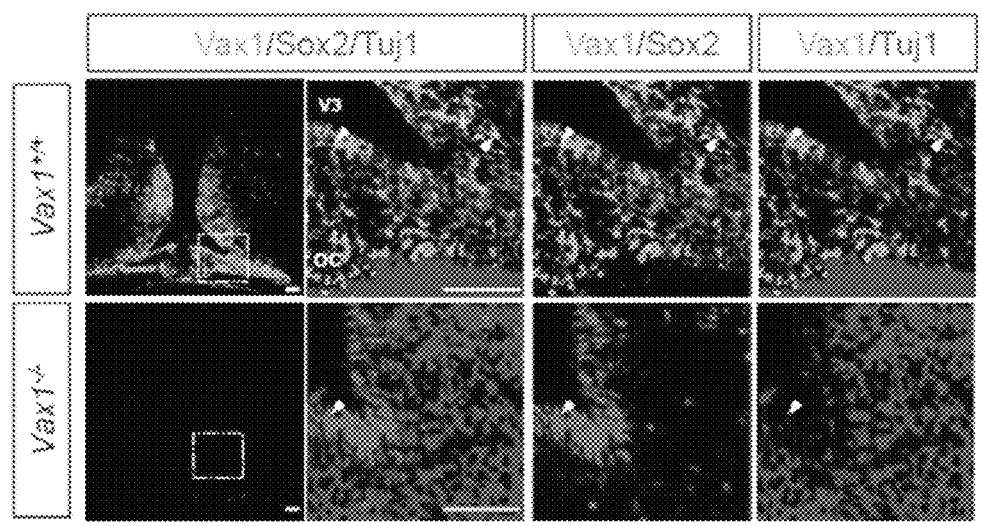

[Figure 1b]
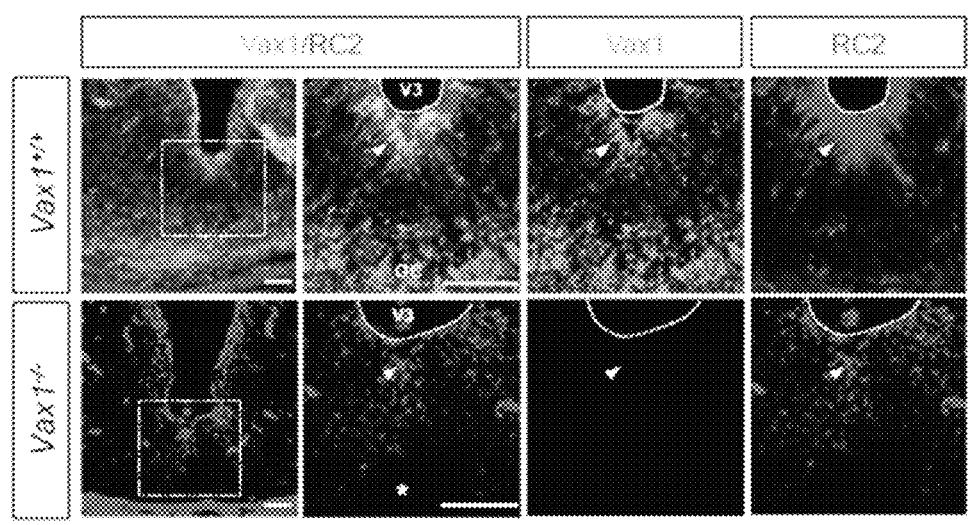

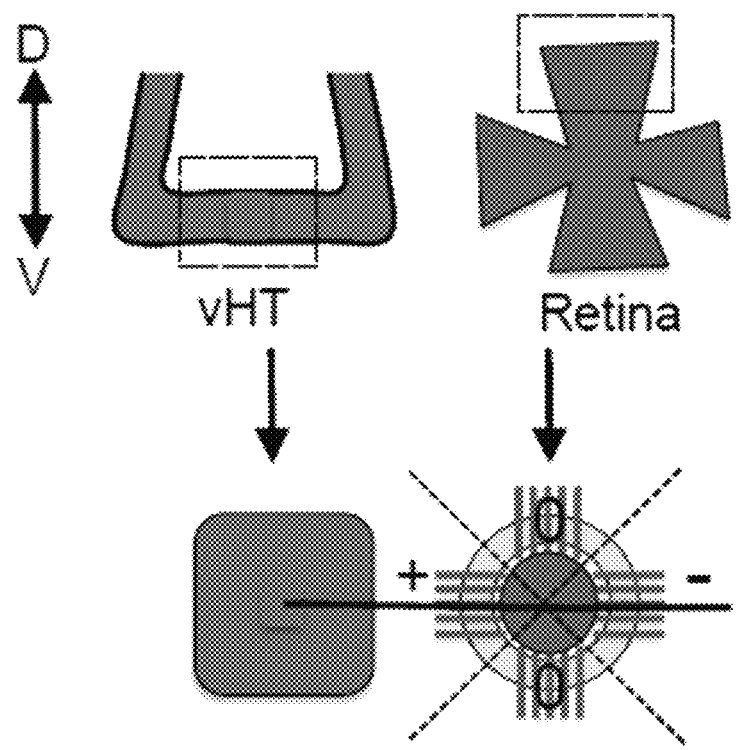
[Figure 2a]

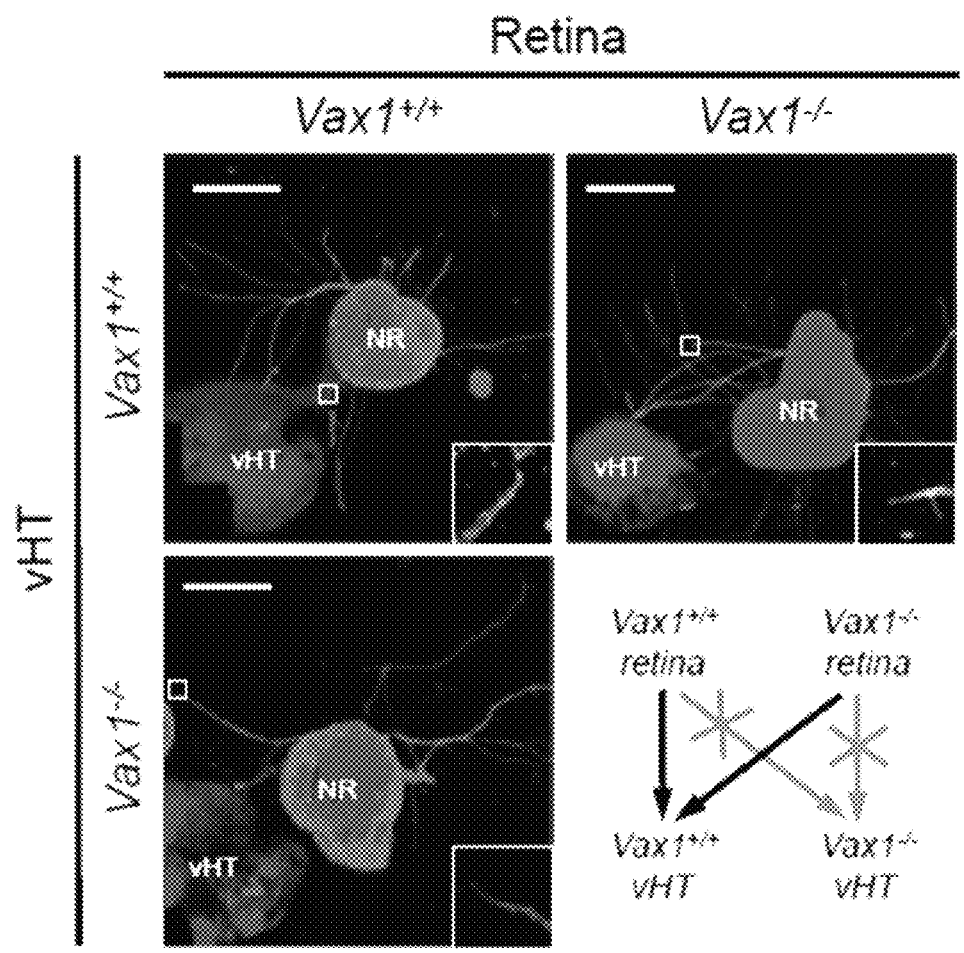
[Figure 2b]

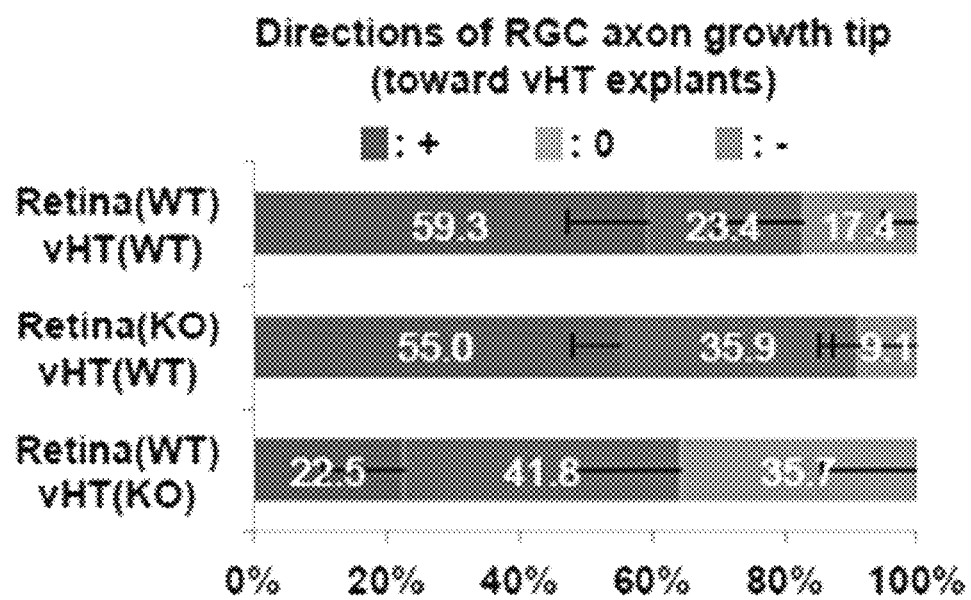

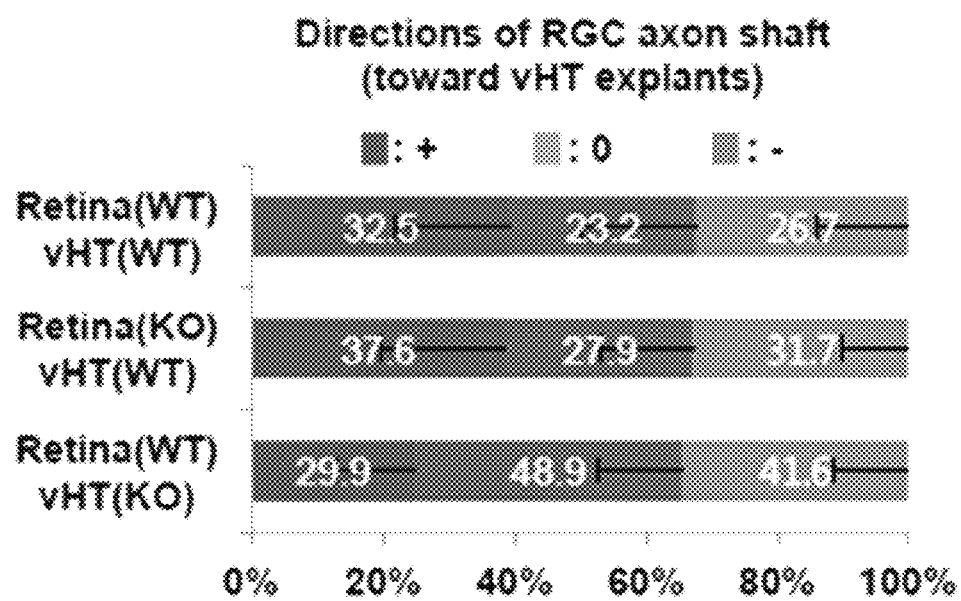
[Figure 2d]

[Figure 2e]
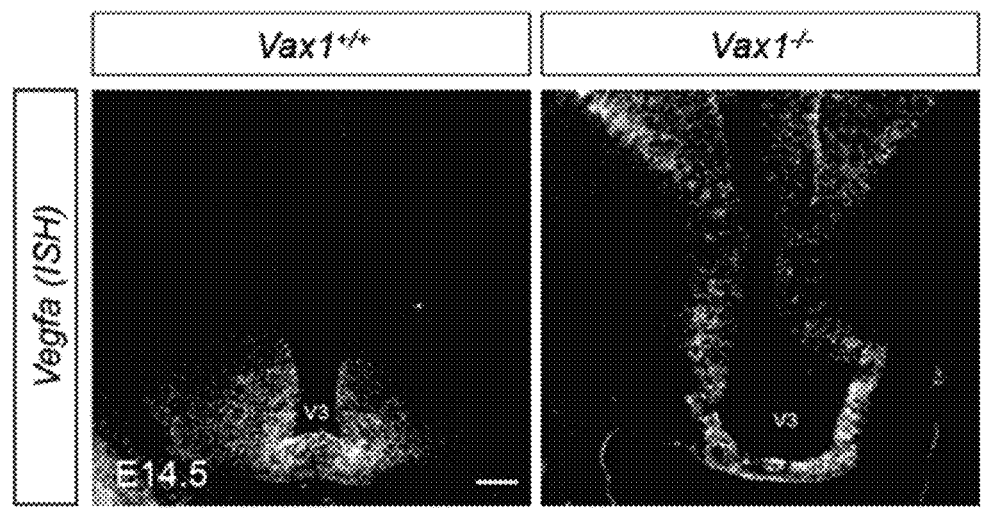
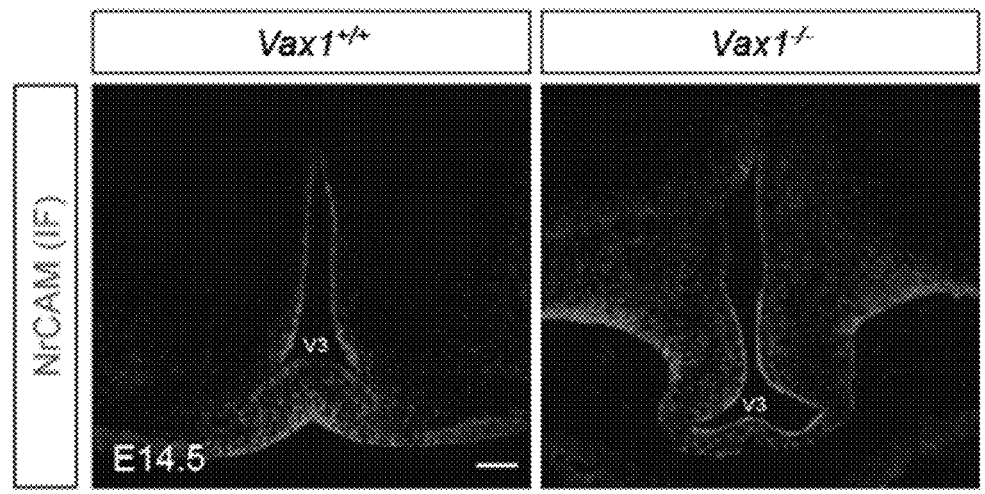

[Figure 3a]
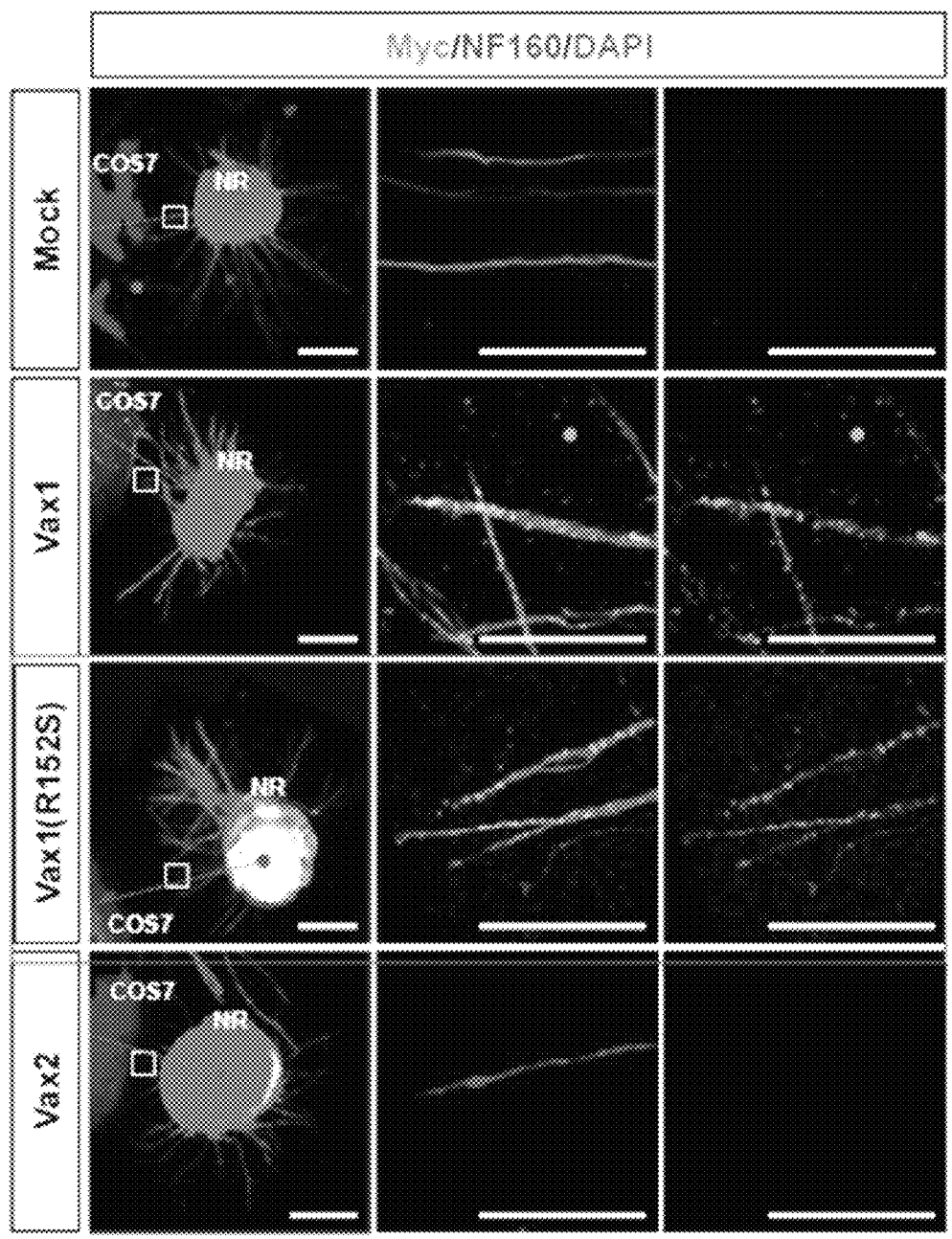

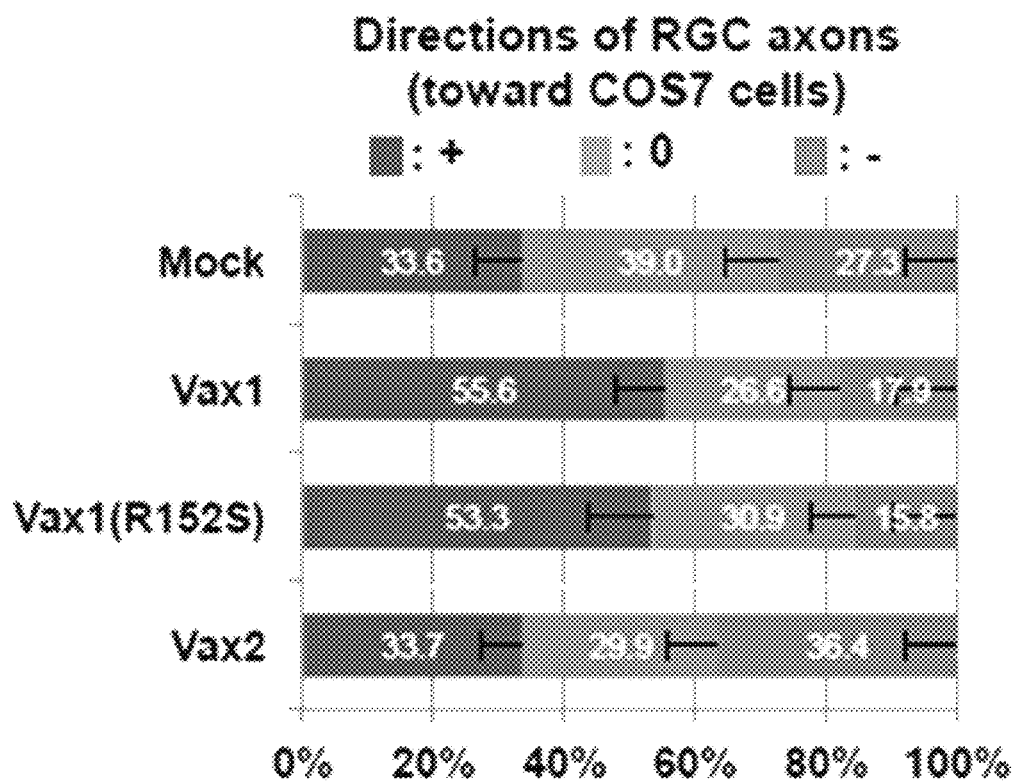

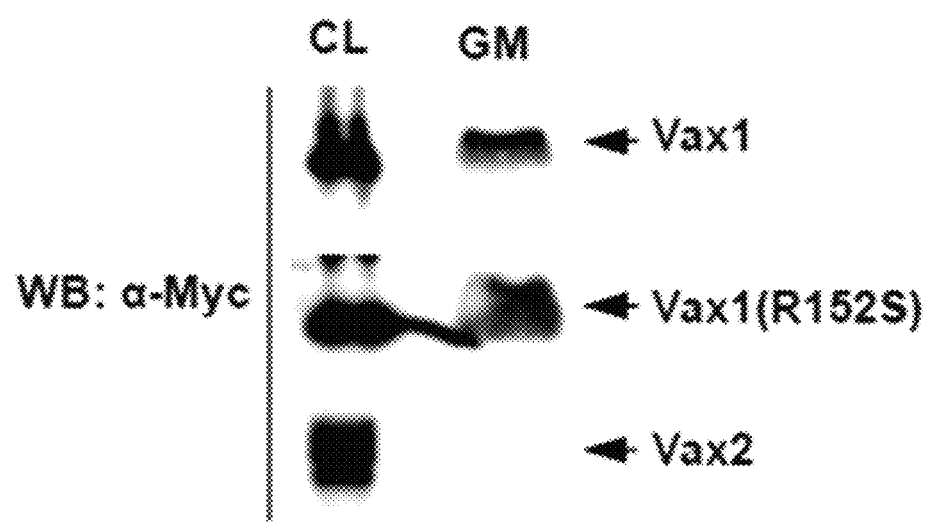
[Figure 3c]

[Figure 4a]
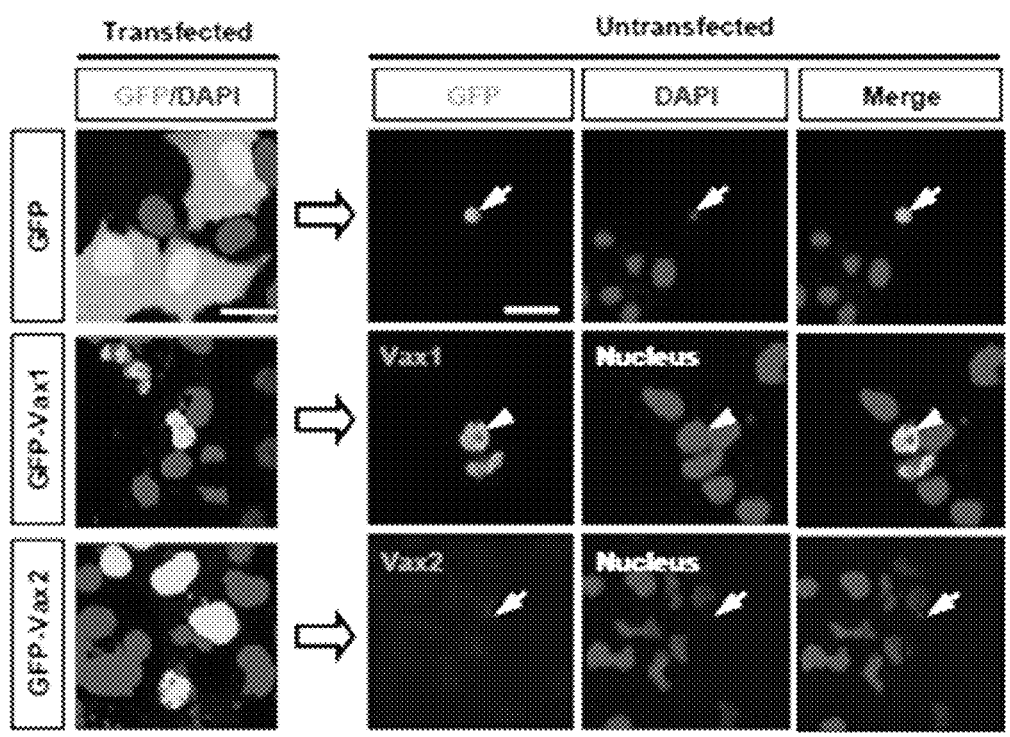

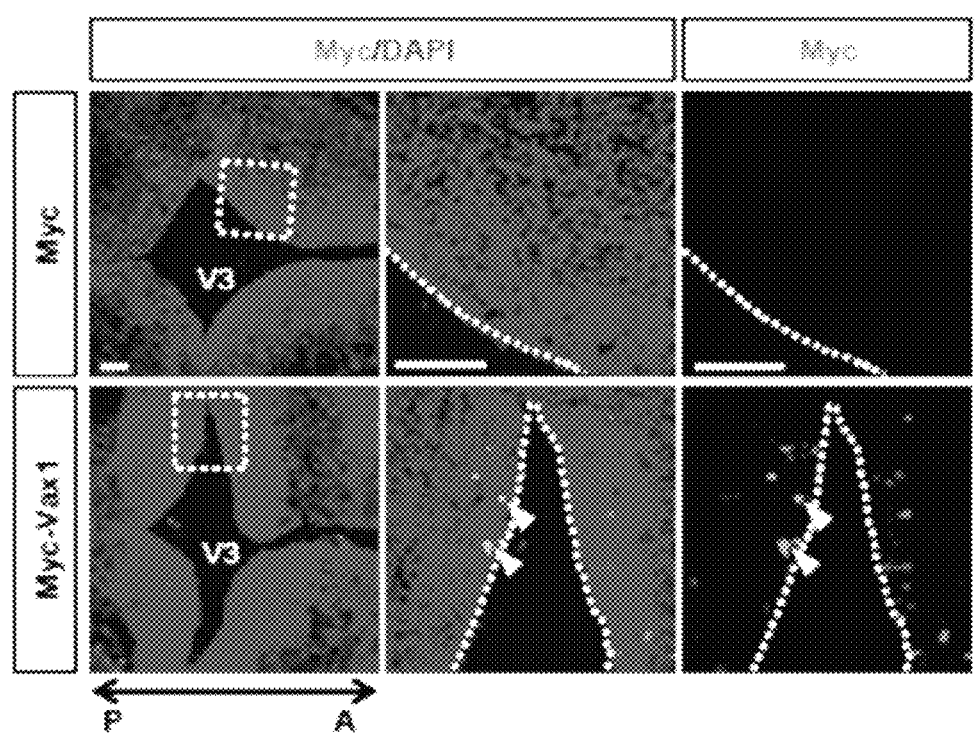
[Figure 4b]

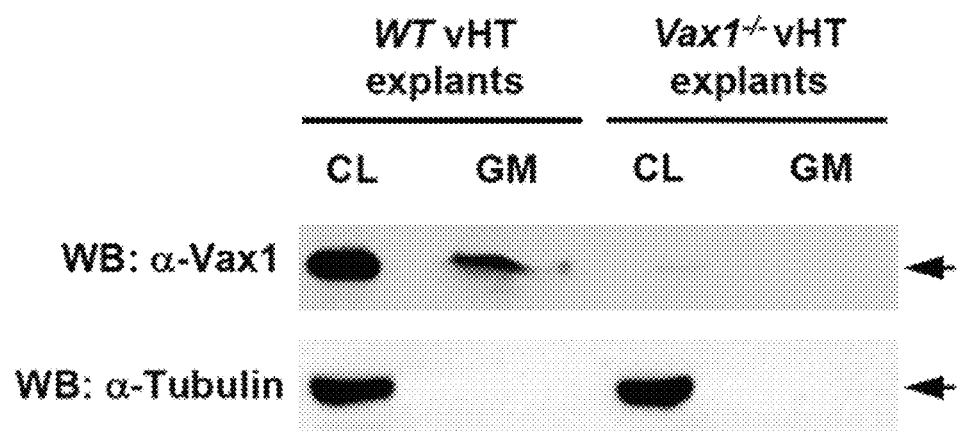

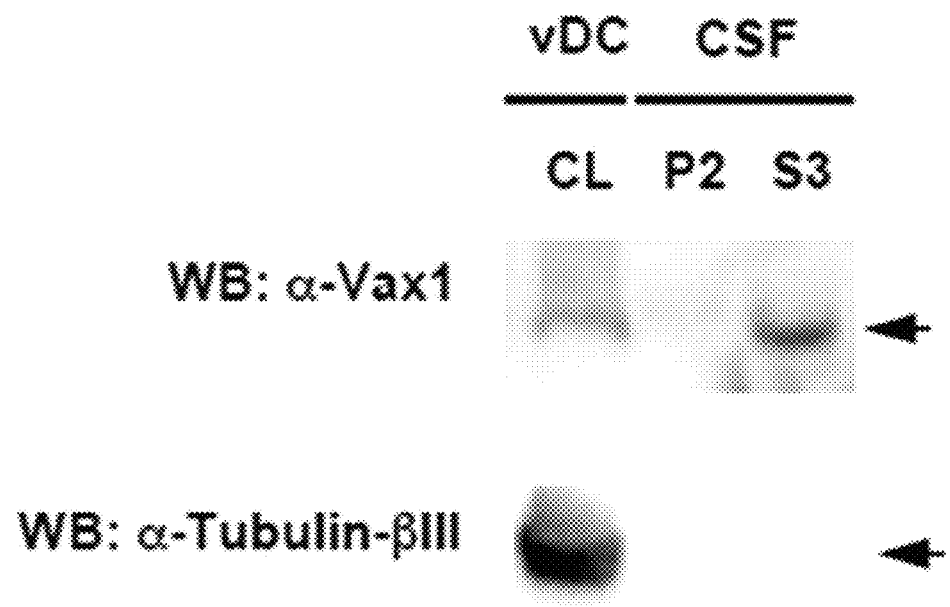
[Figure 4d]

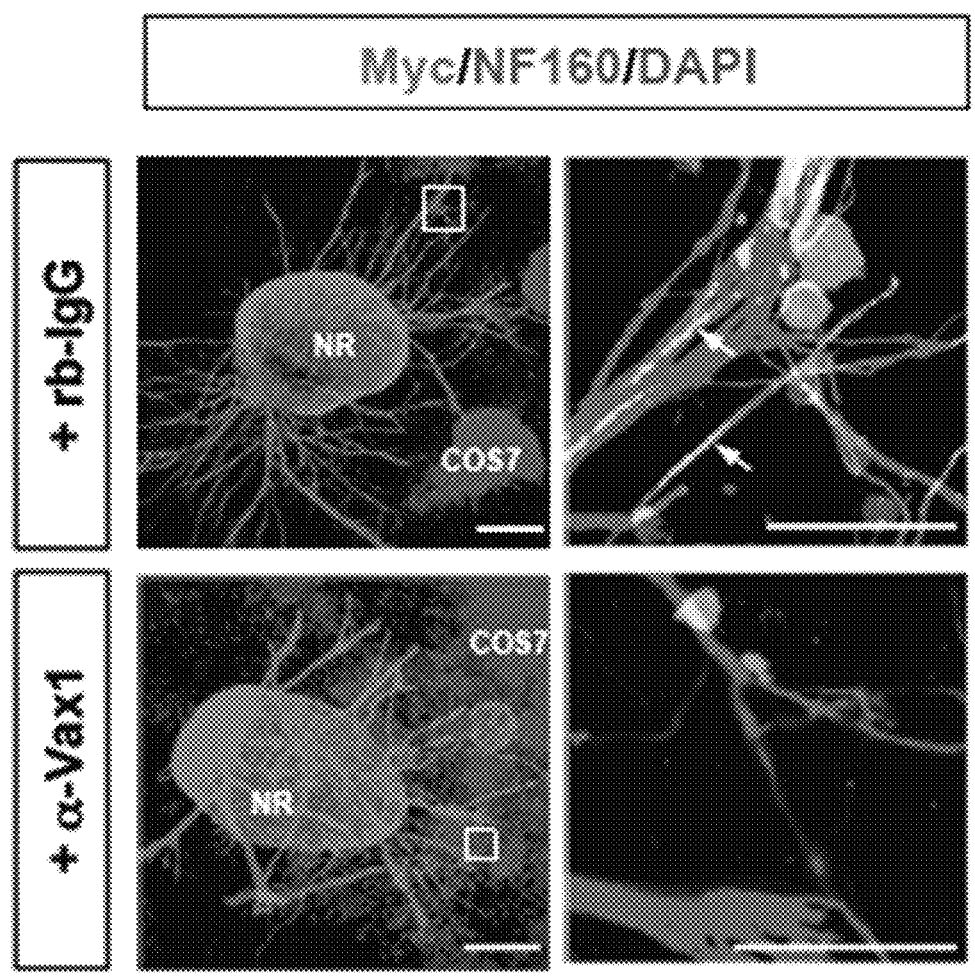
[Figure 4e]

[Figure 5a]
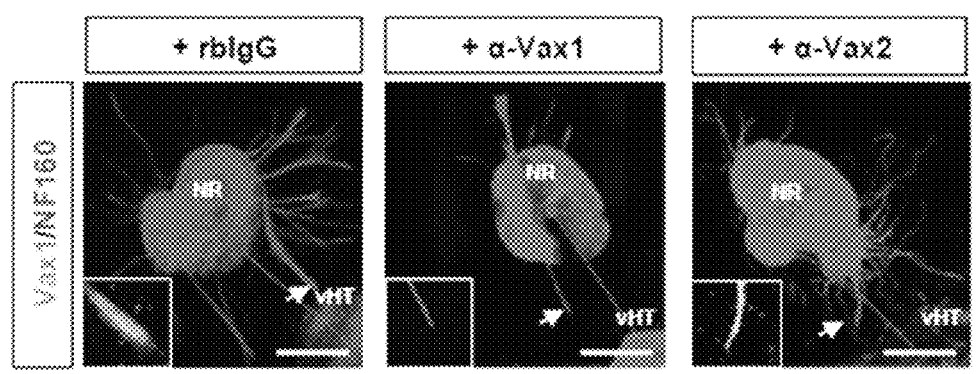

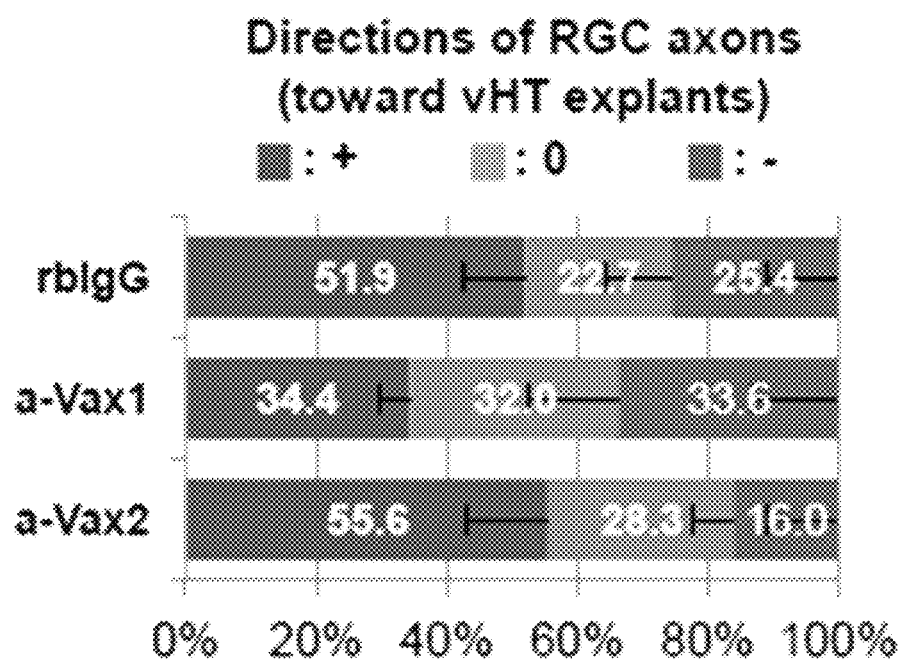
[Figure 5b]

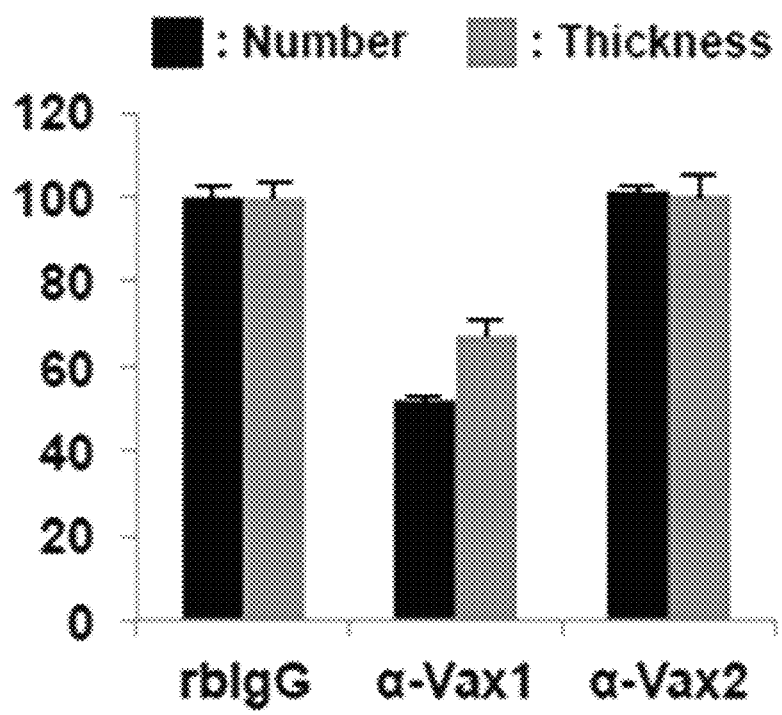

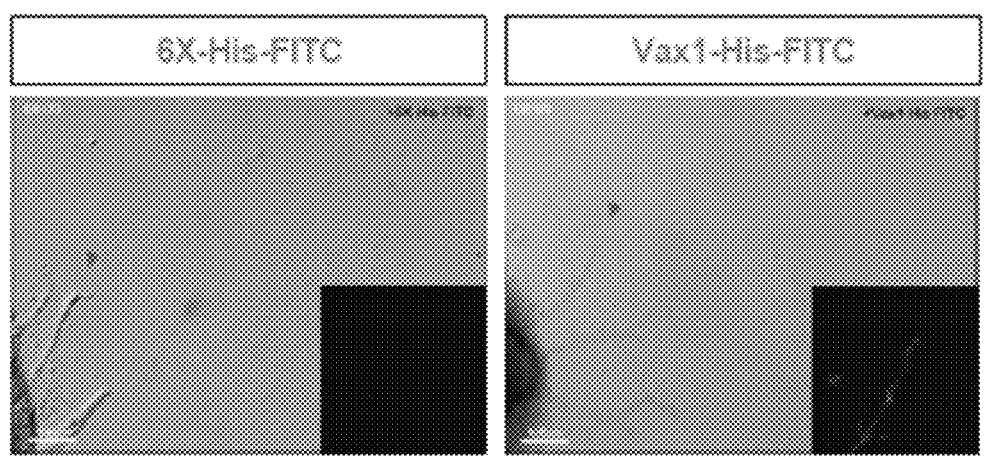
[Figure 5d]

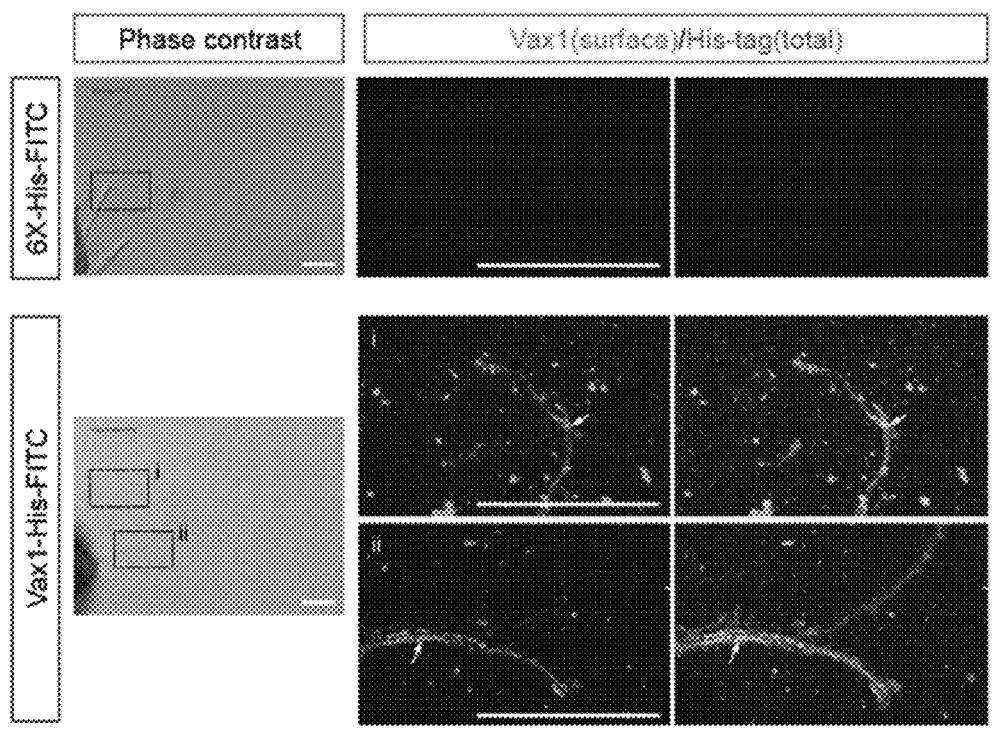
[Figure 5e]

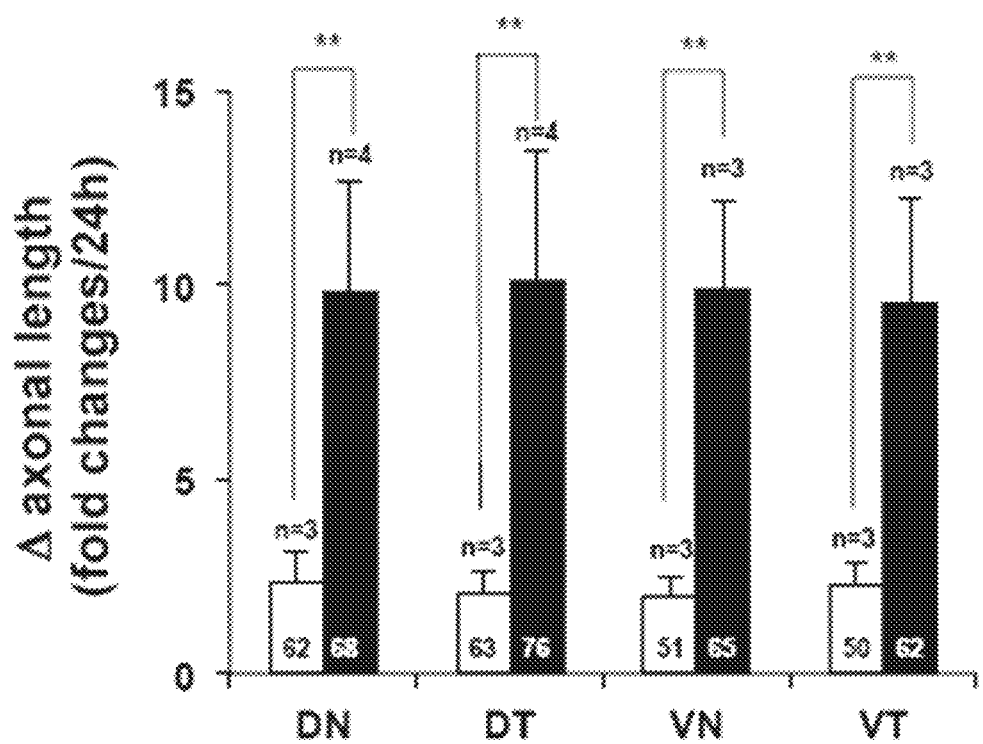
[Figure 5f]

[Figure 5g]
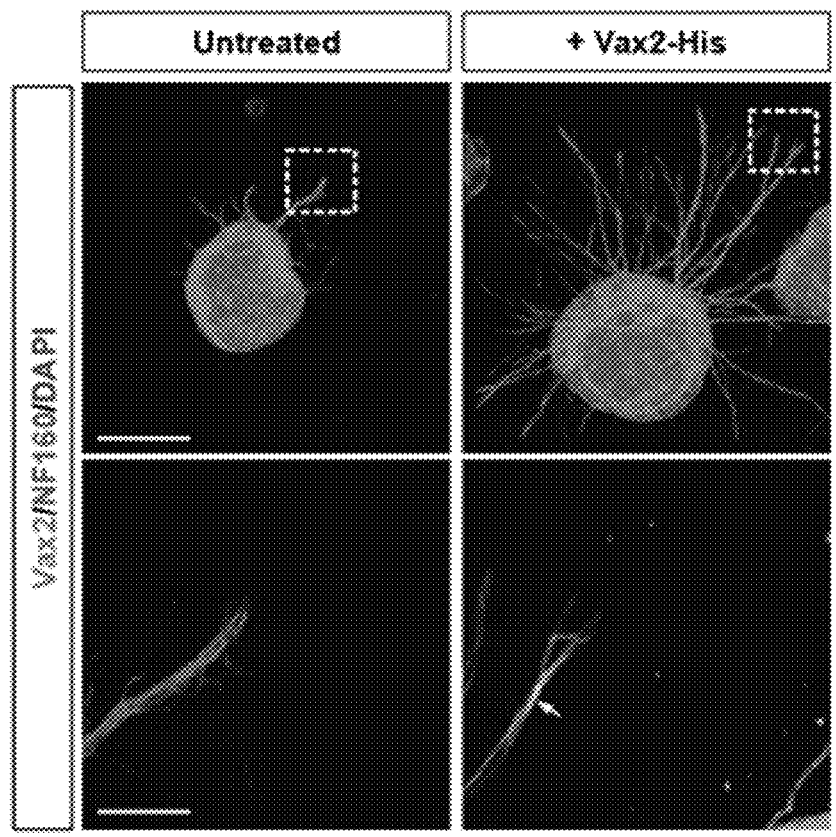
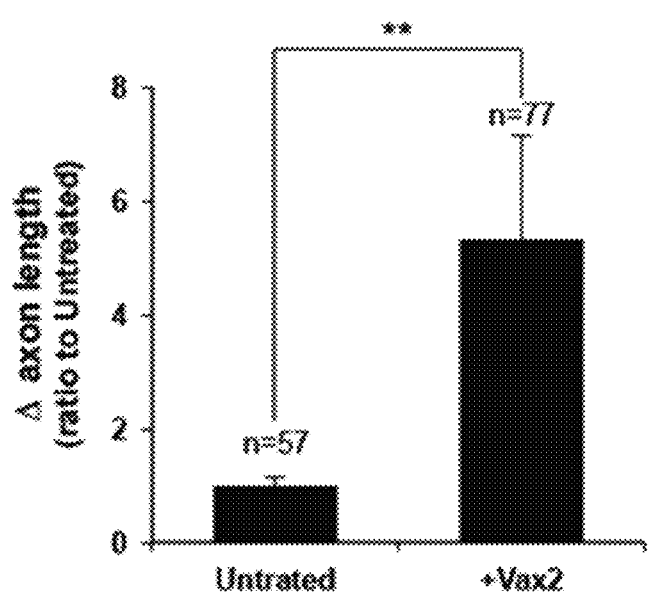

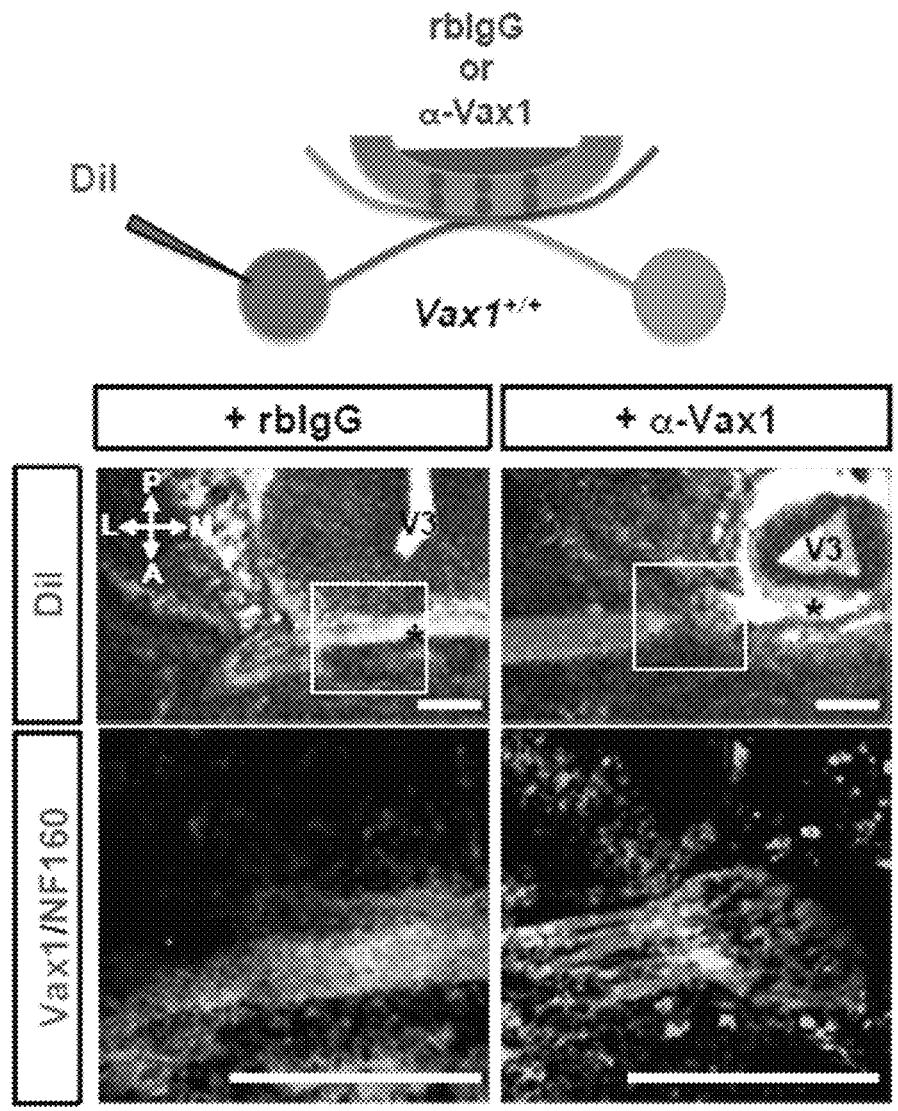

[Figure 6b]
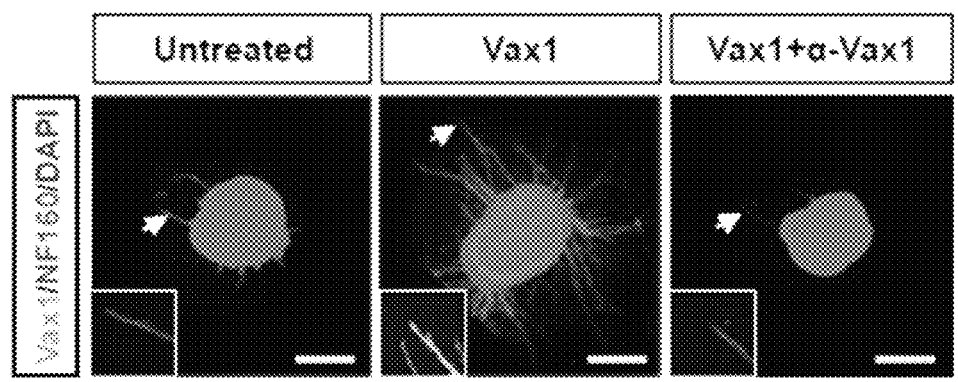

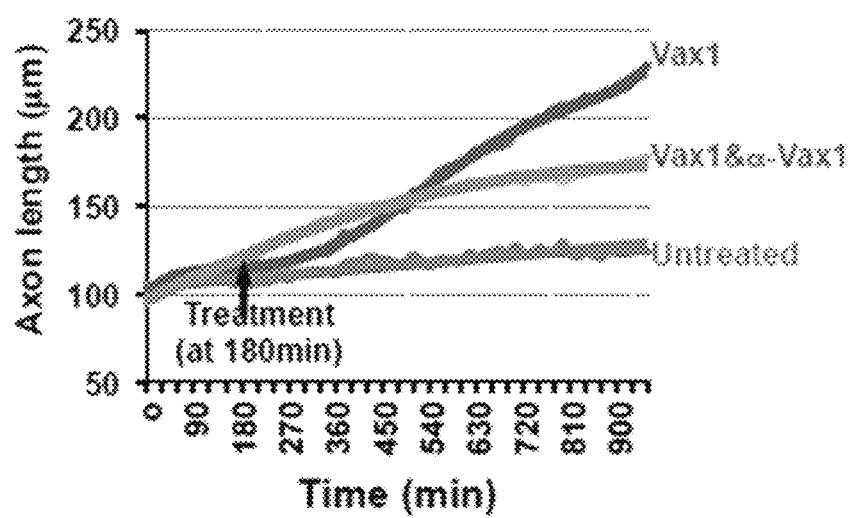

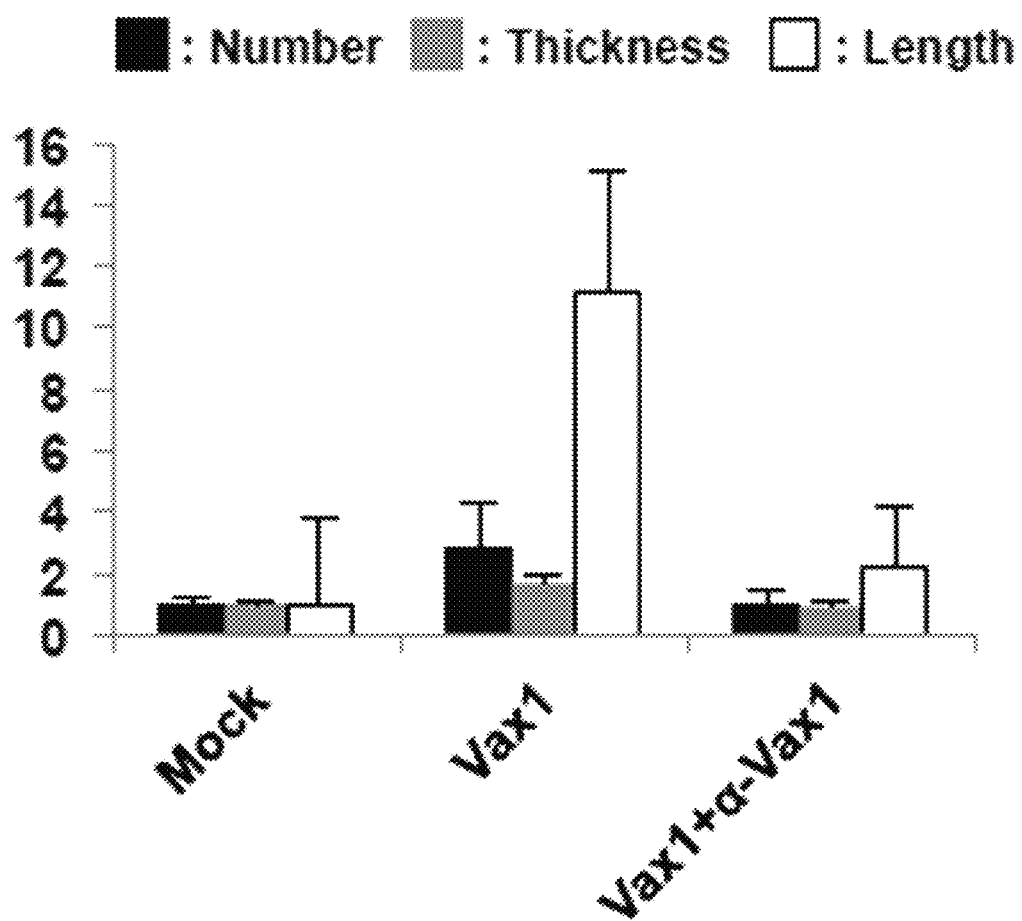
[Figure 6d]

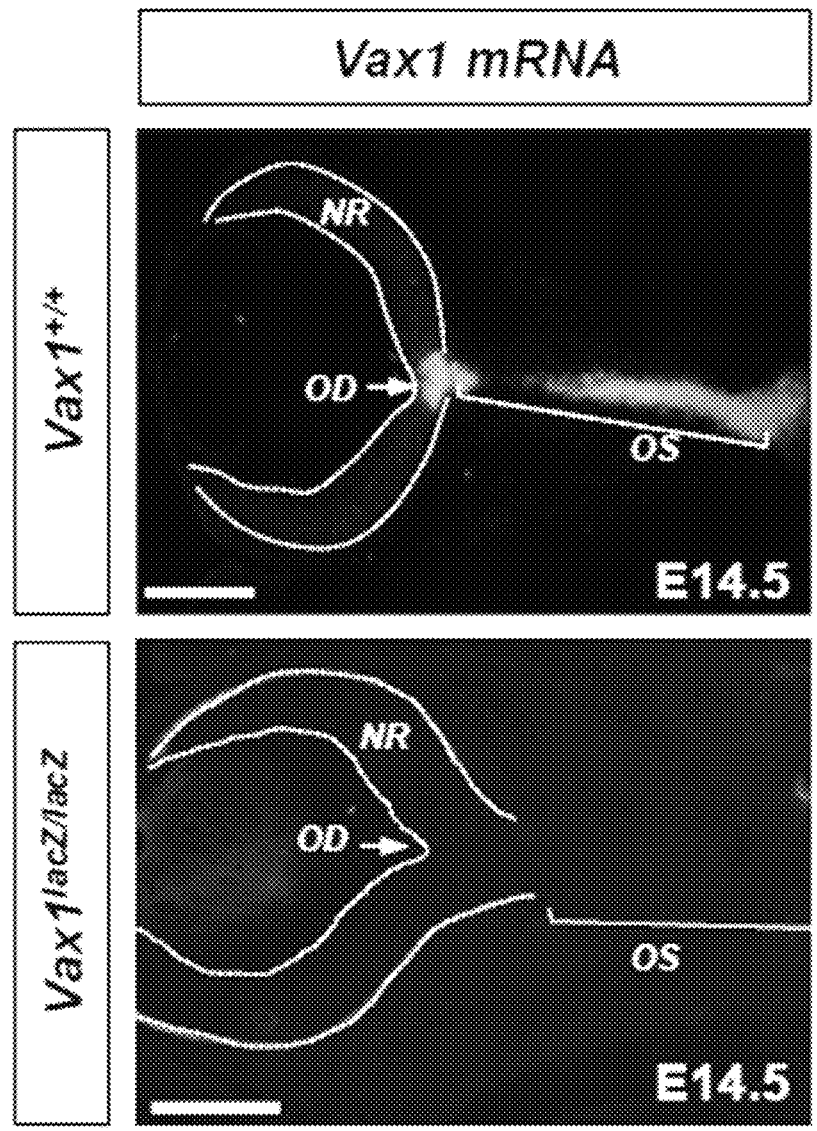

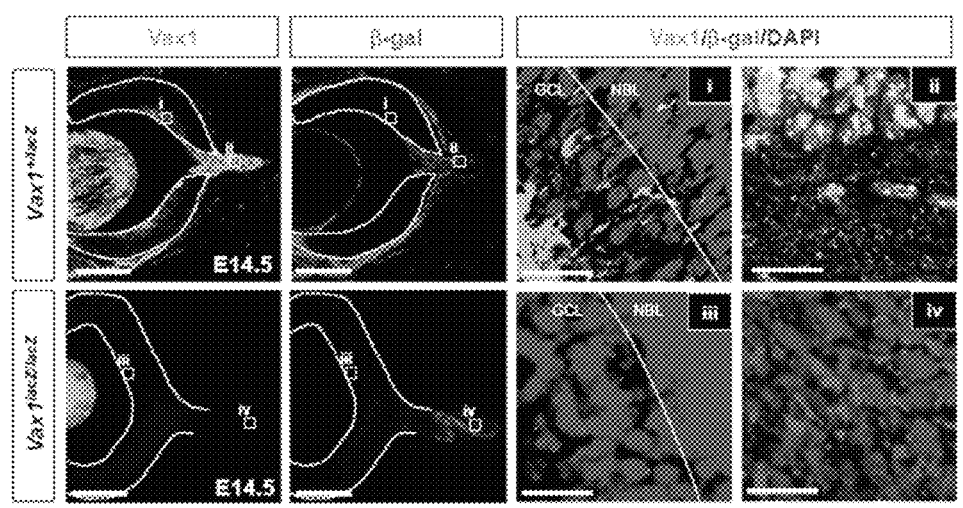
[Figure 7b]

[Figure 7c]
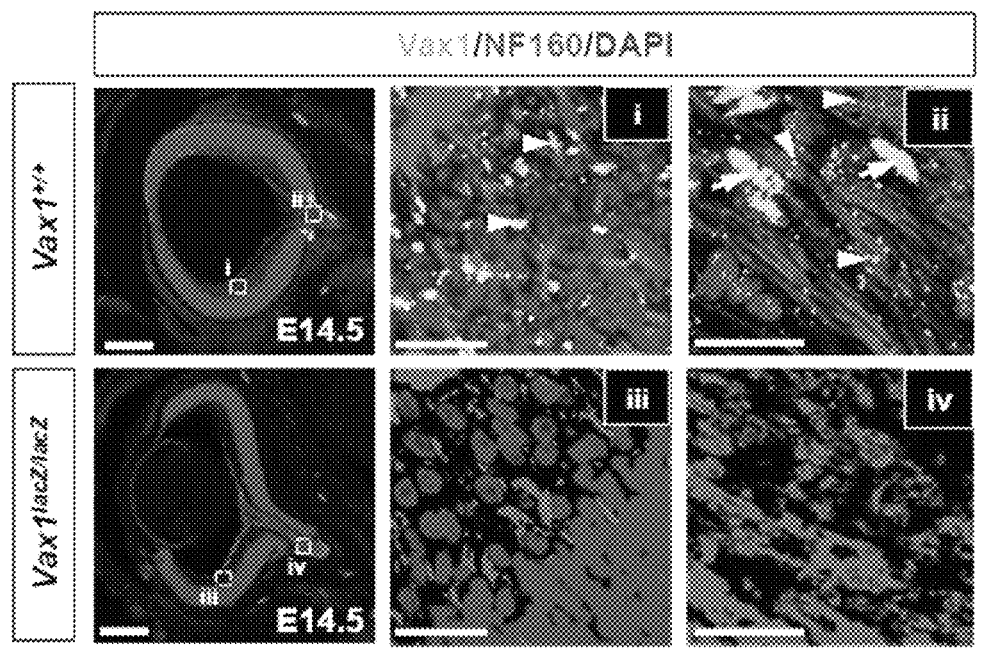

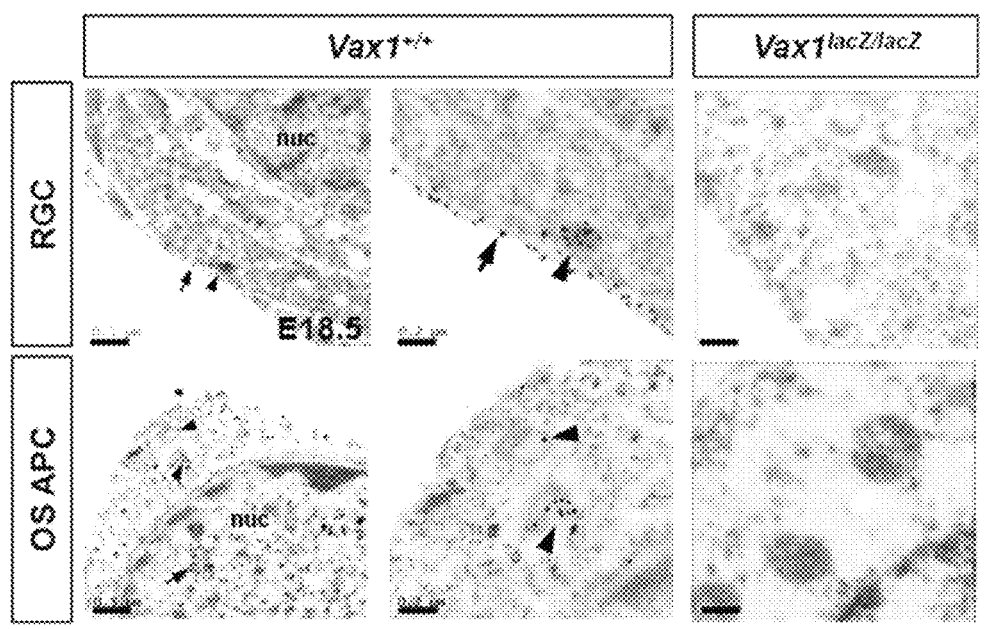
[Figure 7d]

[Figure 7e]
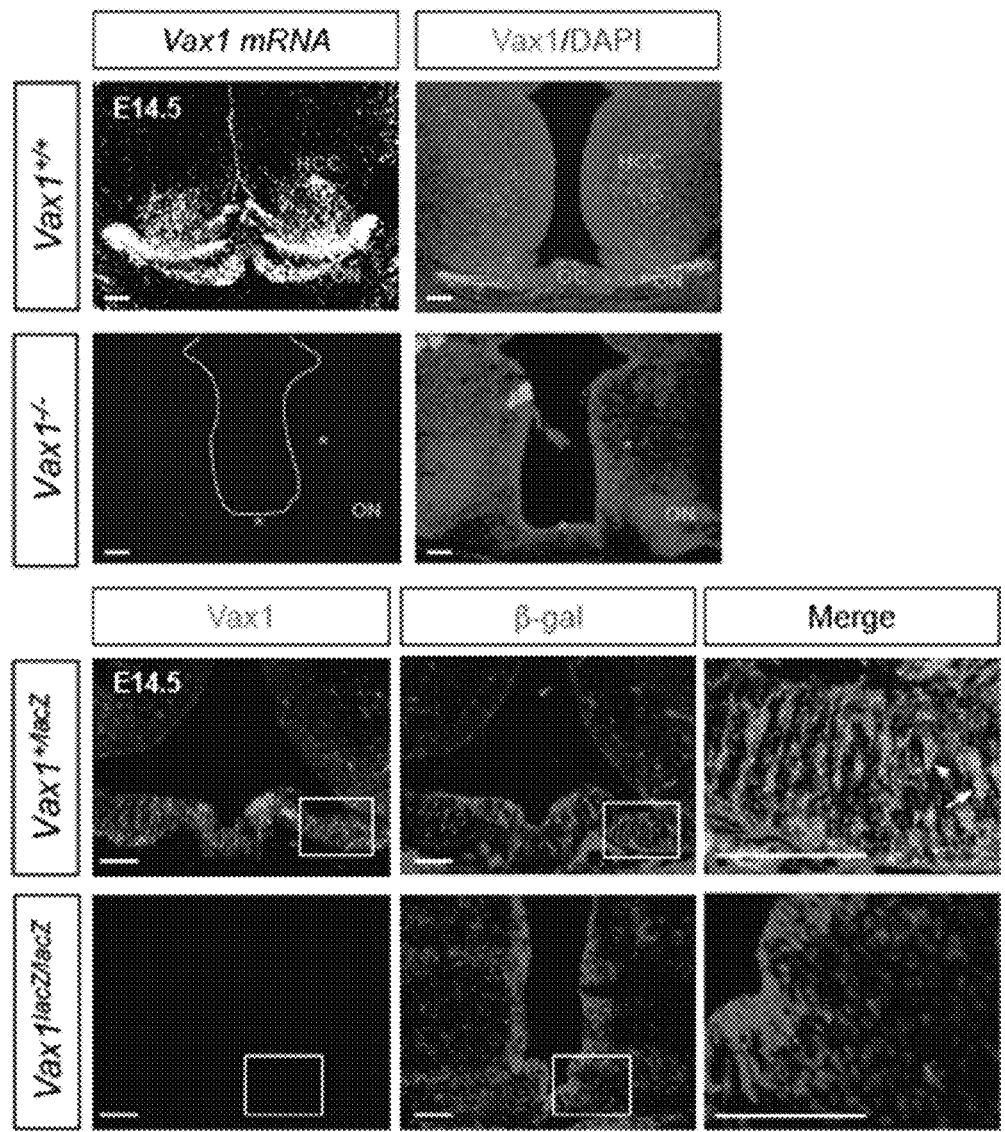

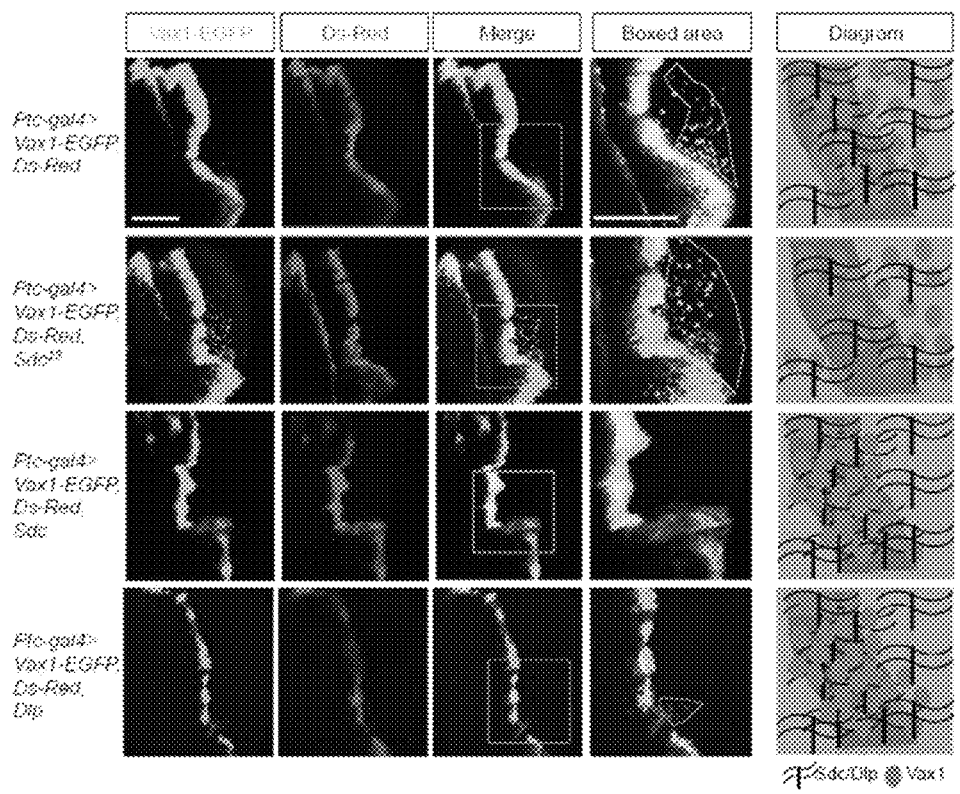

[Figure 9a]
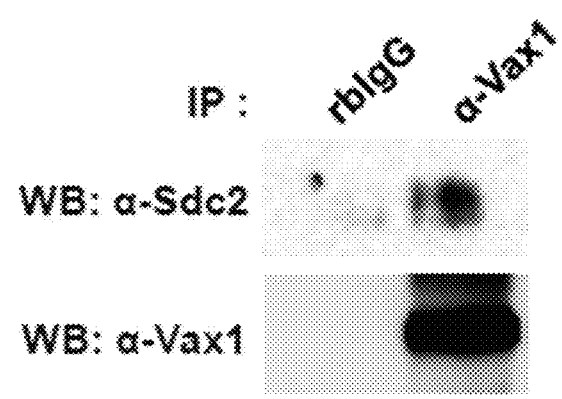
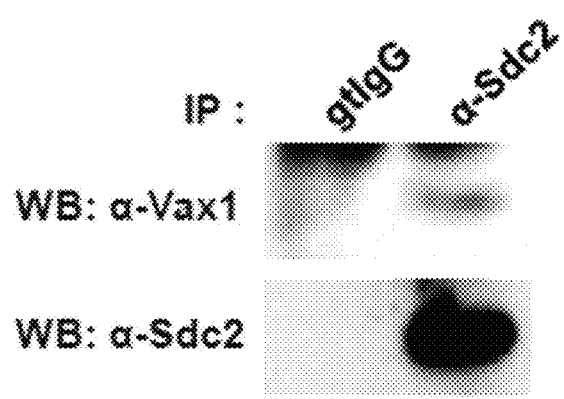

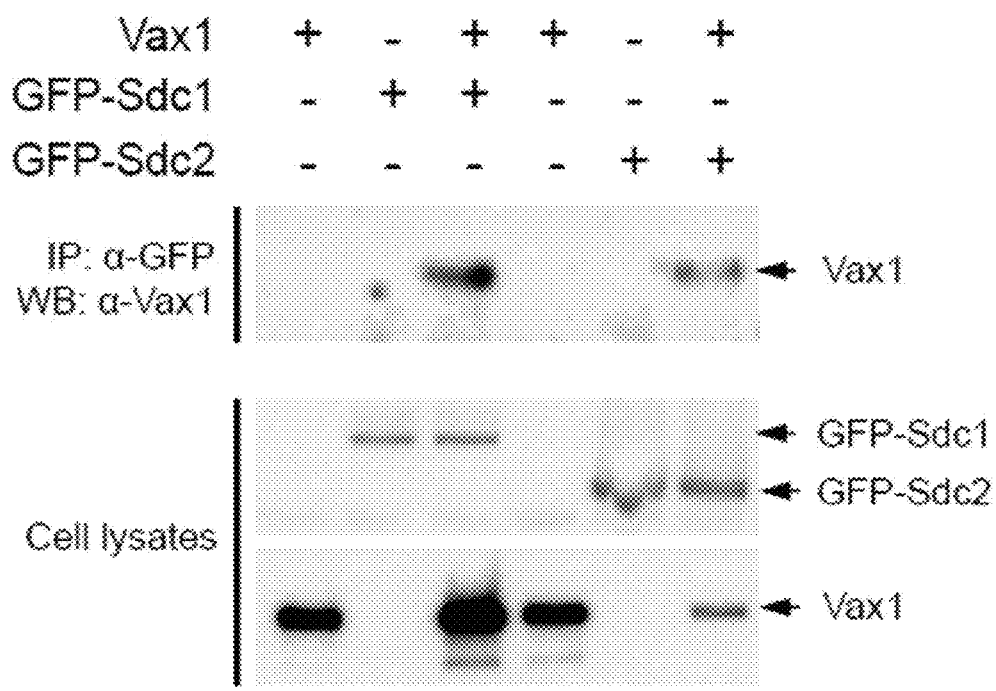
[Figure 9b]

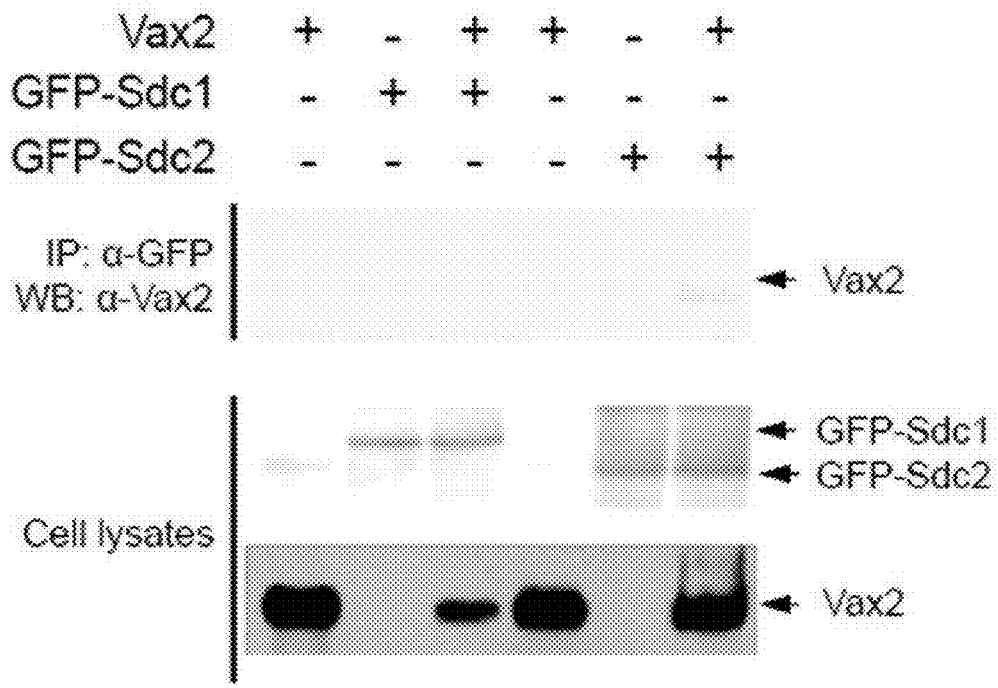

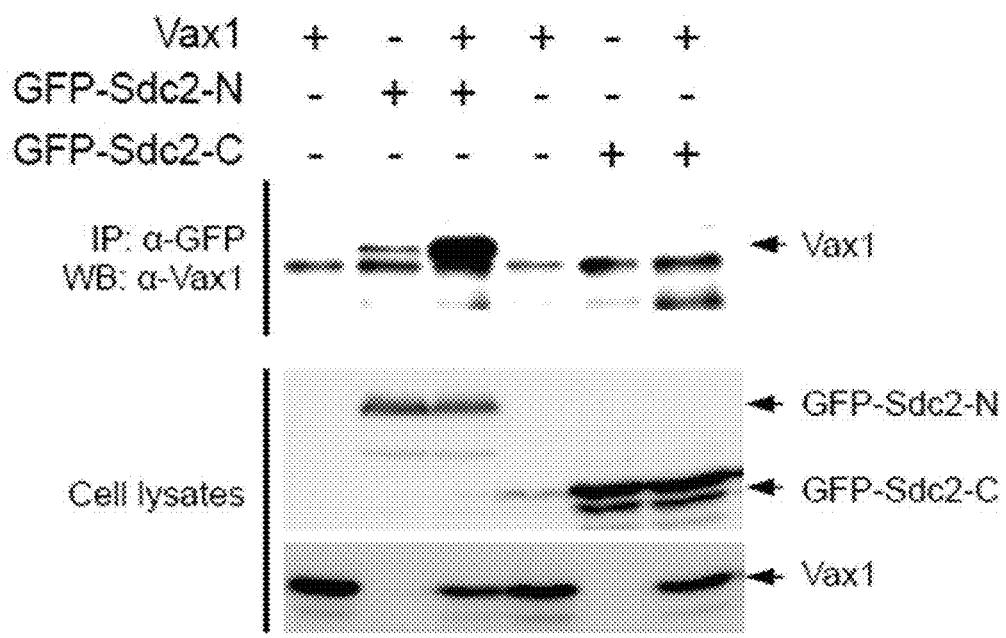

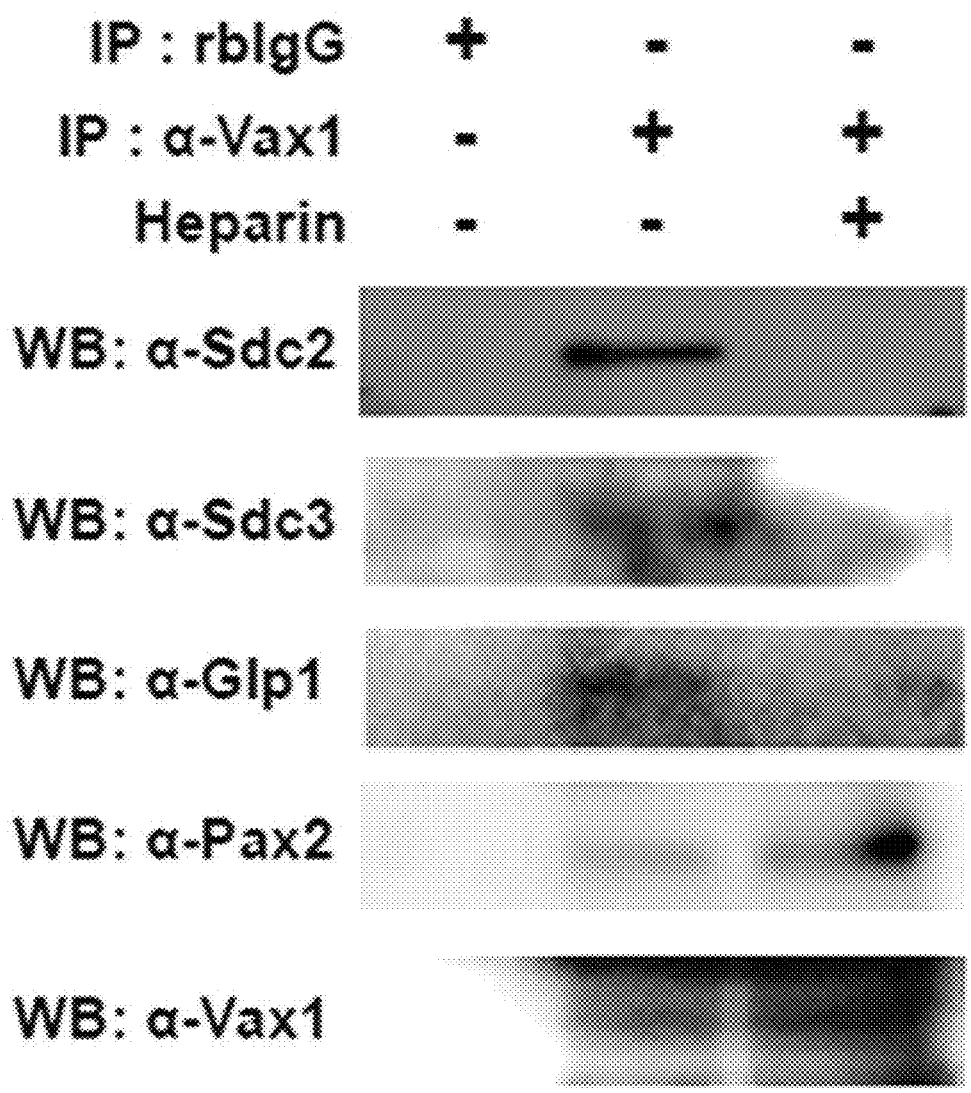
[Figure 9e]

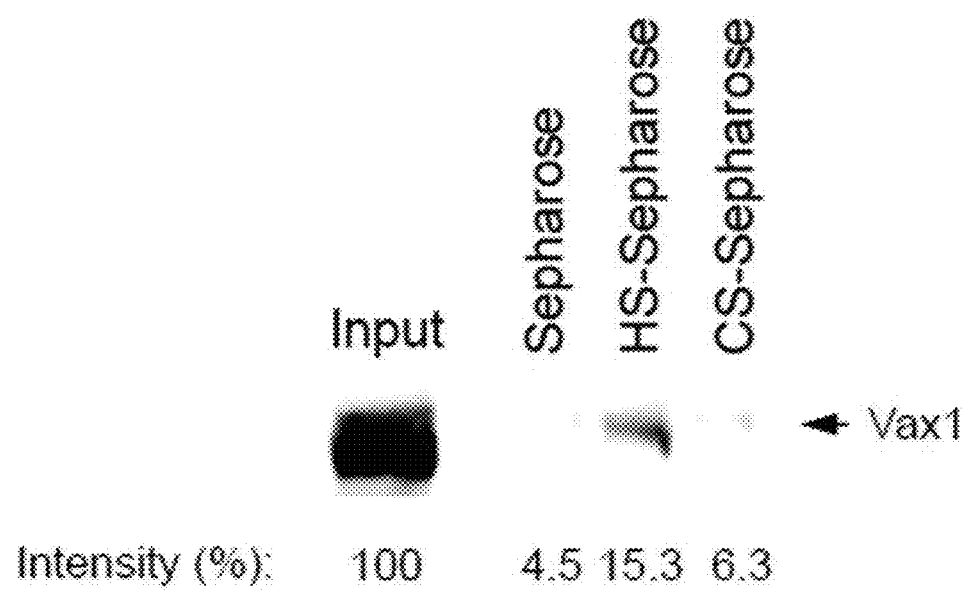
[Figure 9f]

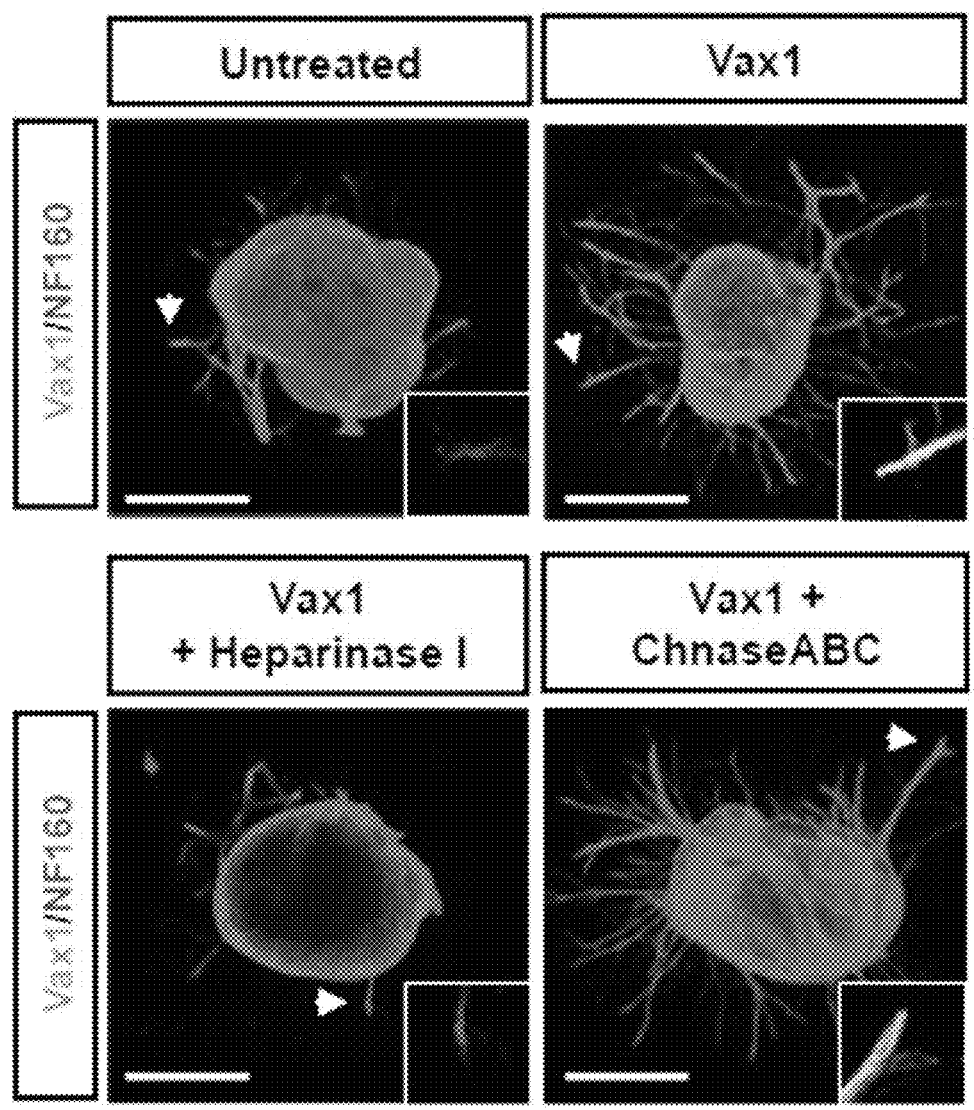
[Figure 10a]

[Figure 10b]
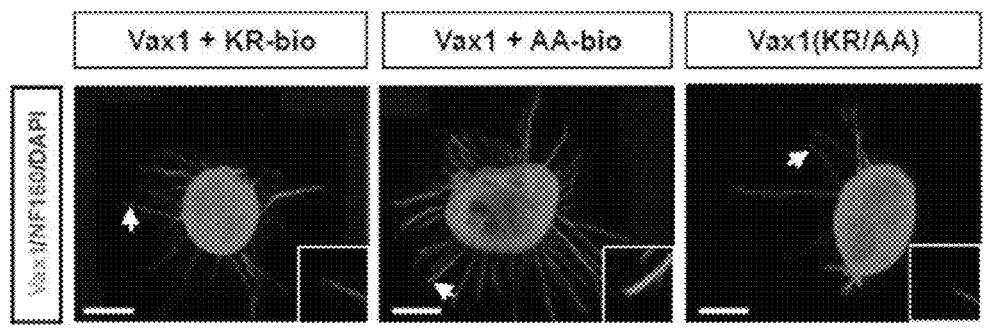

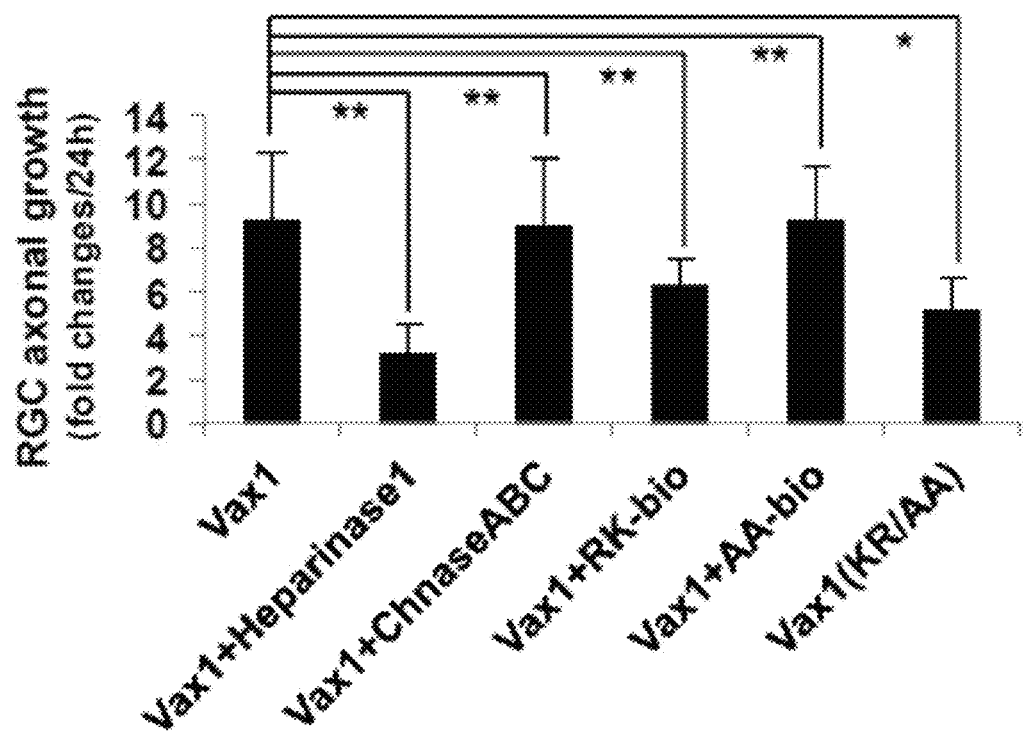
[Figure 10c]

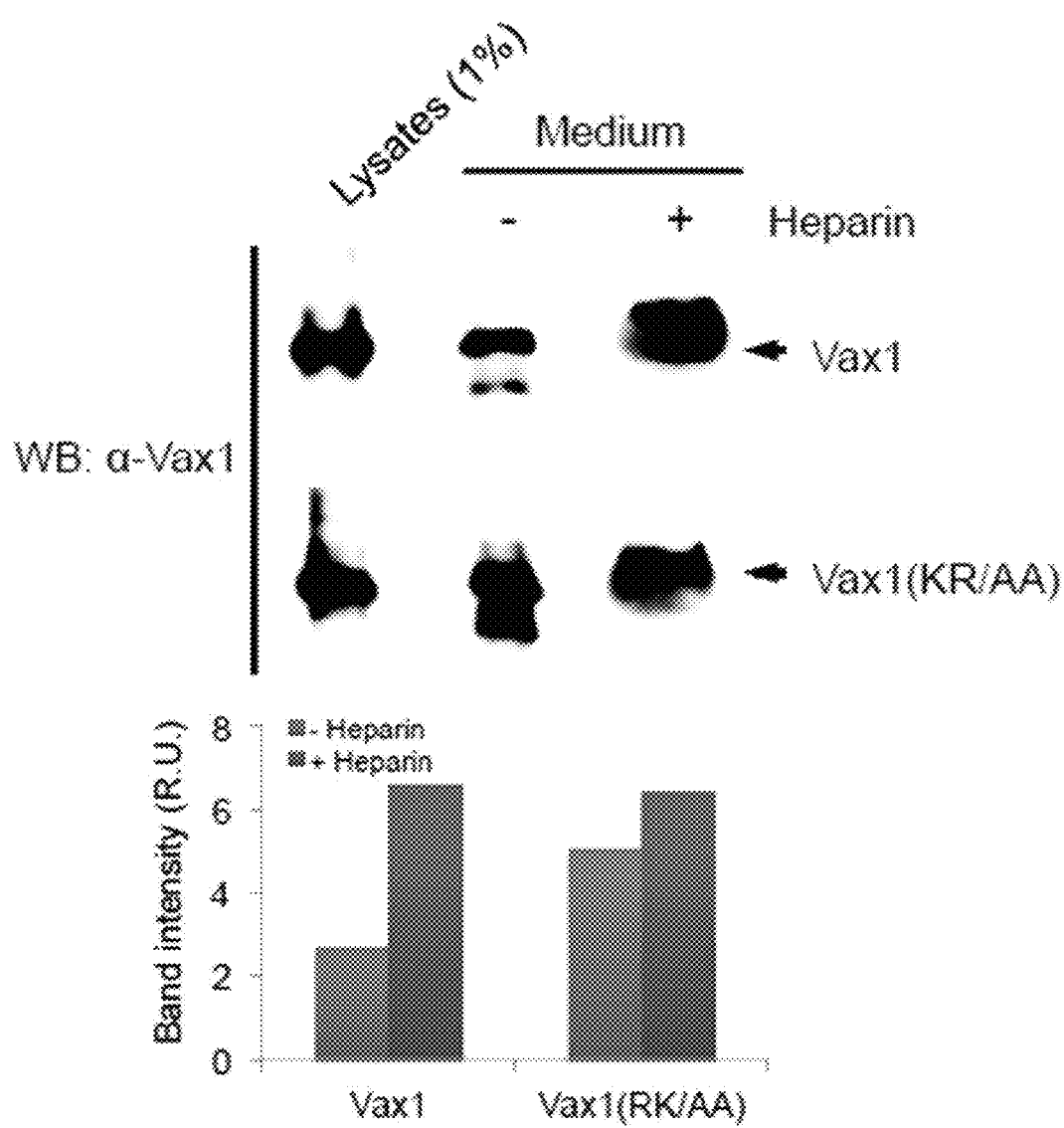

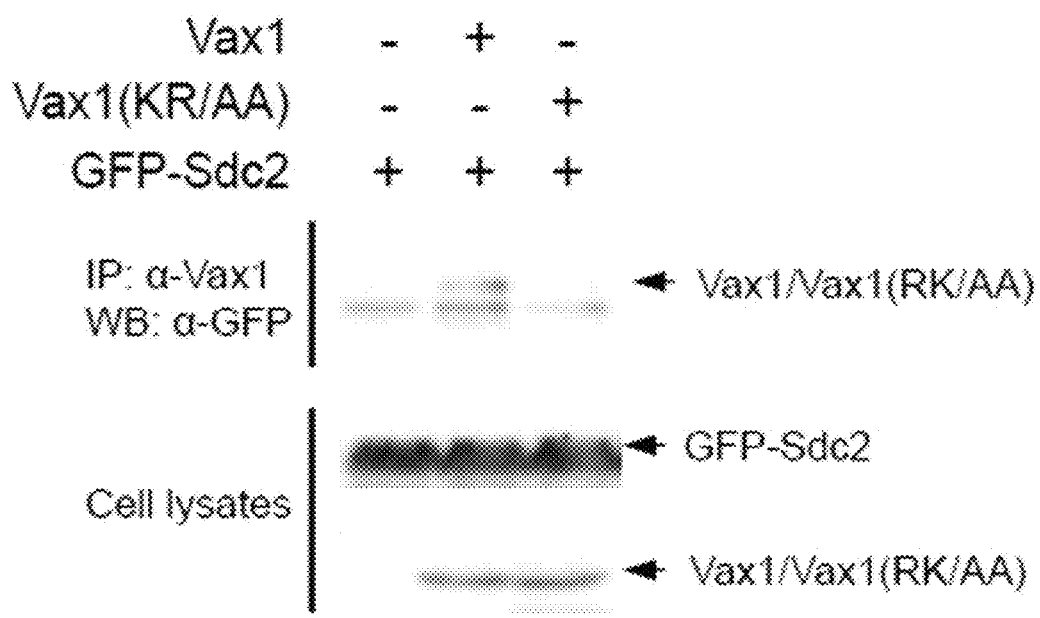
[Figure 11b]

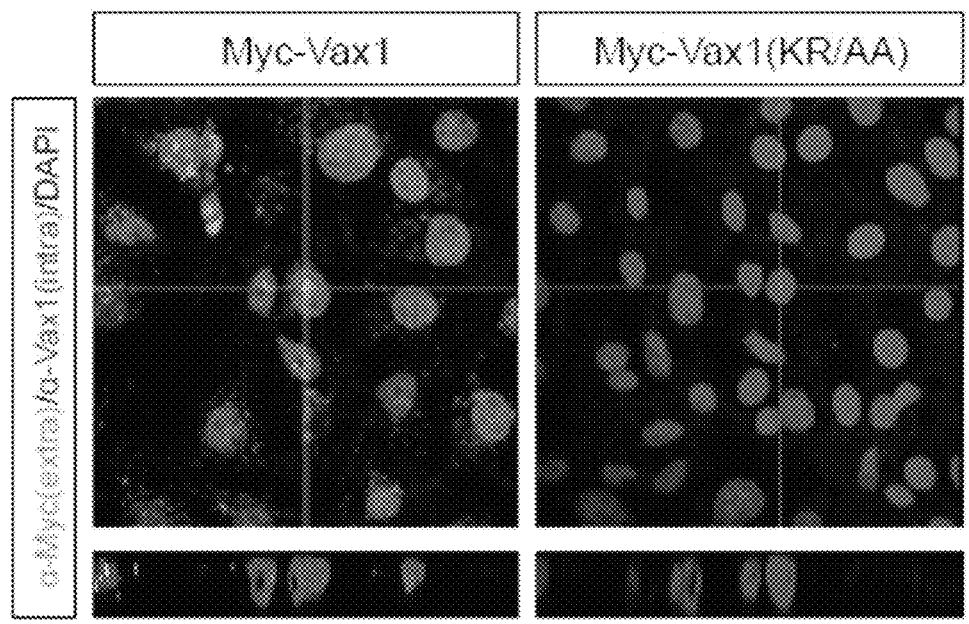
[Figure 11c]

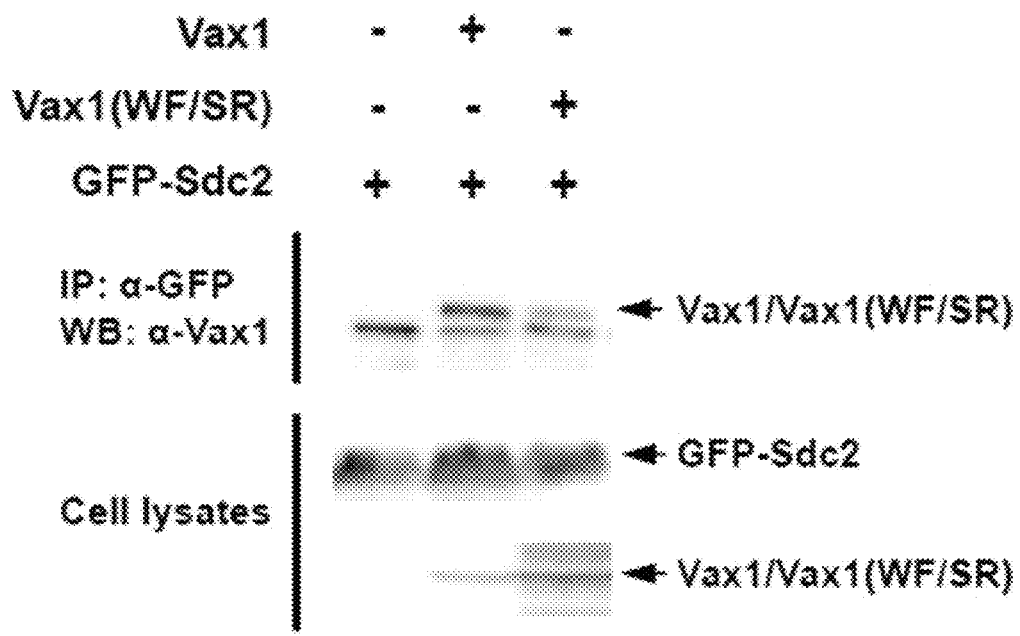
[Figure 12a]

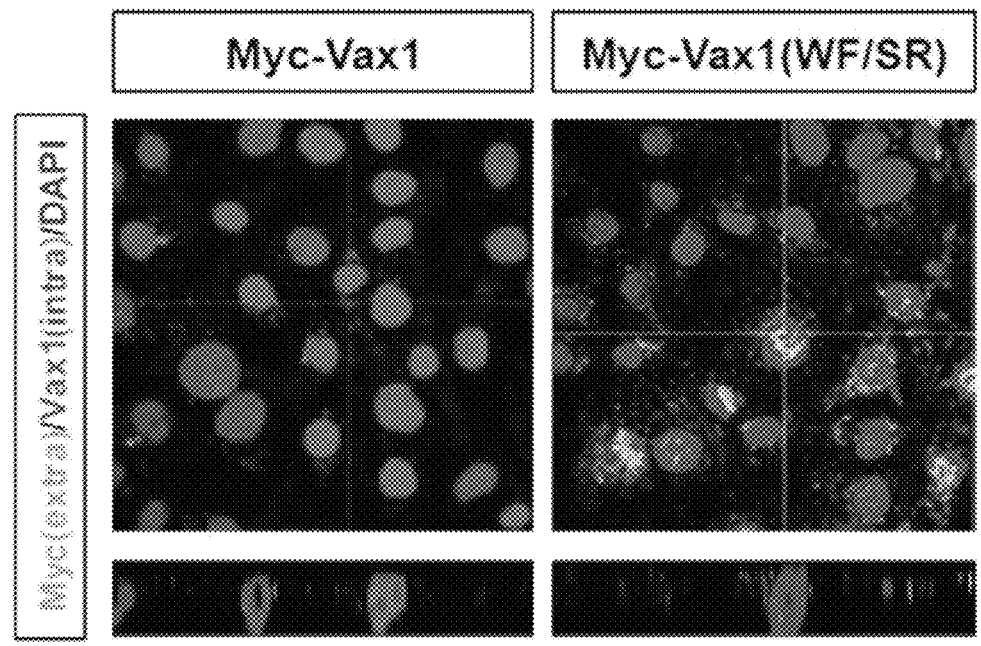
[Figure 12b]

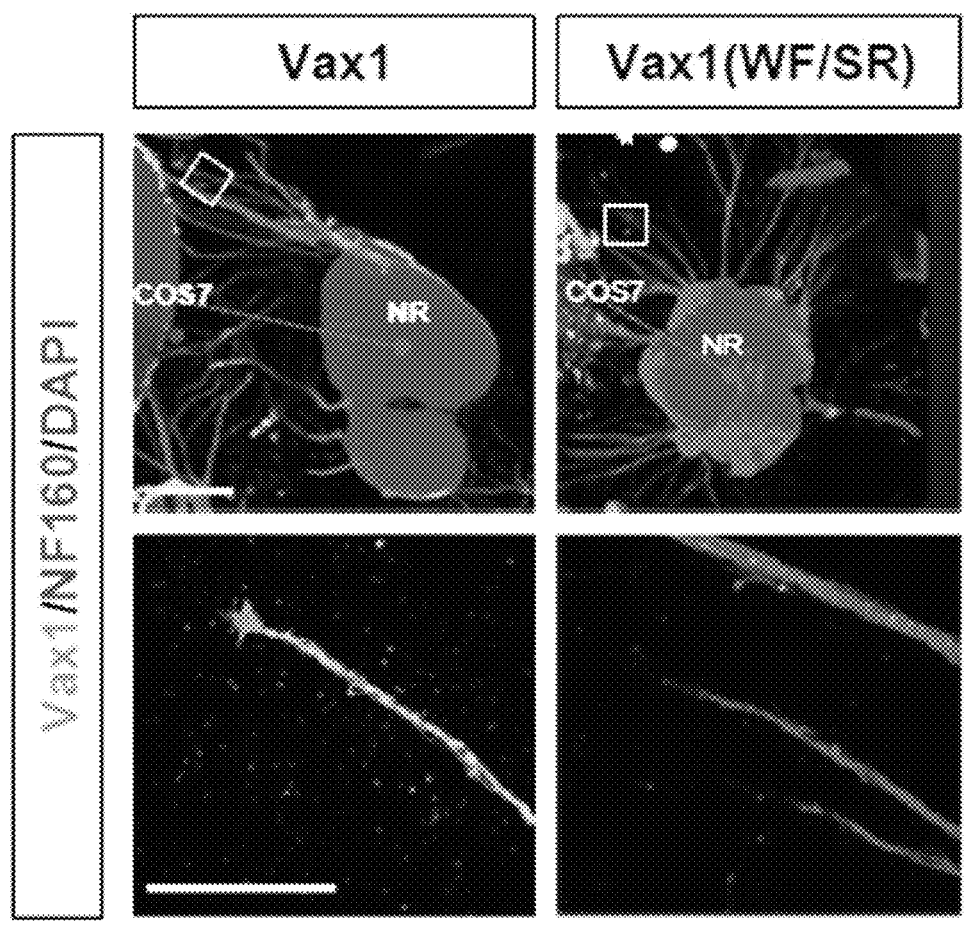

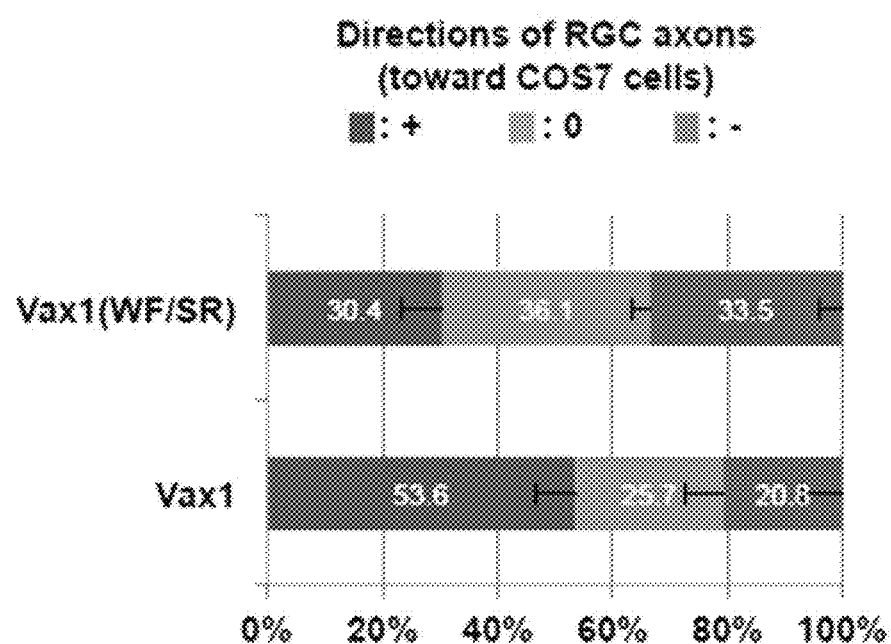
[Figure 12d]

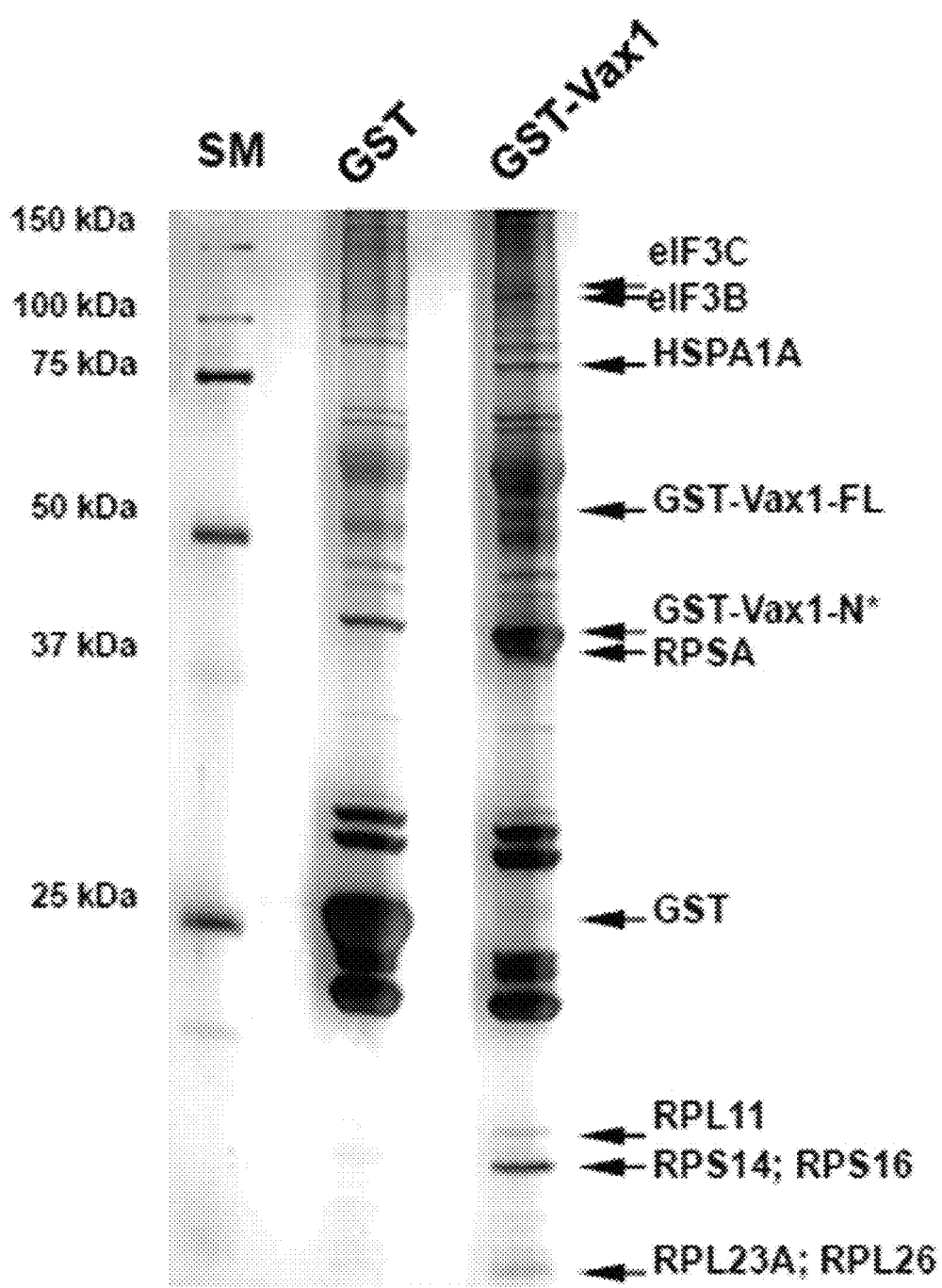
[Figure 13a]

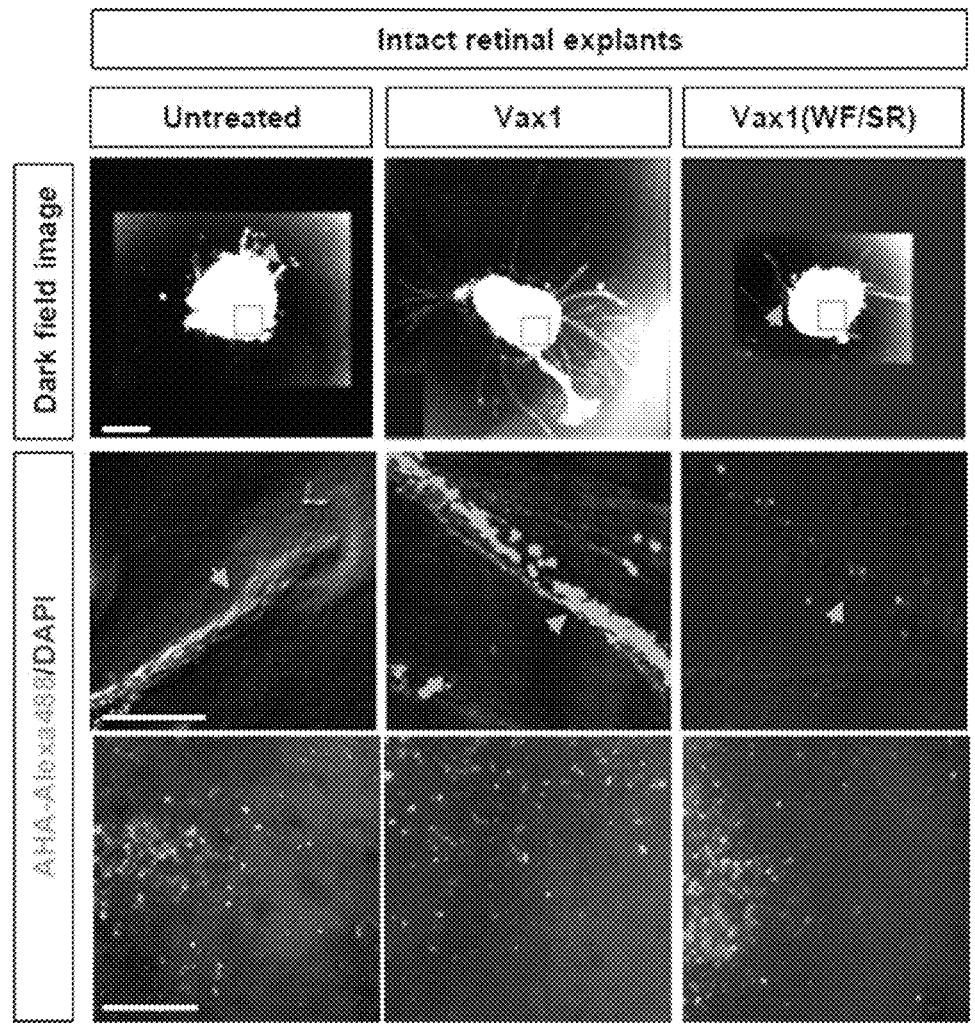

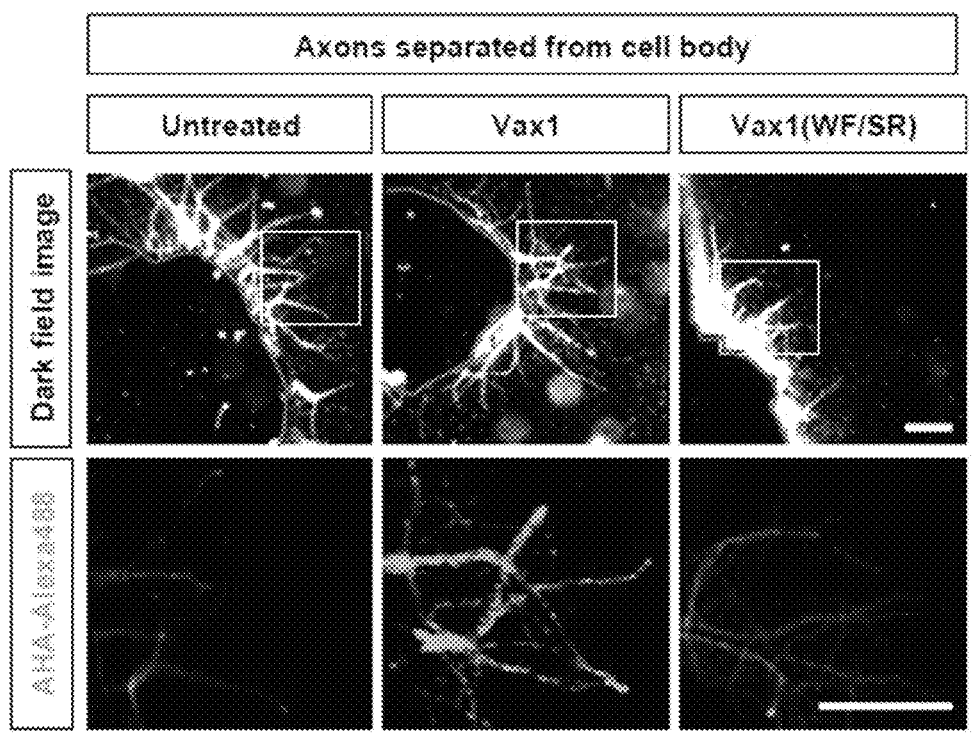
[Figure 13c]

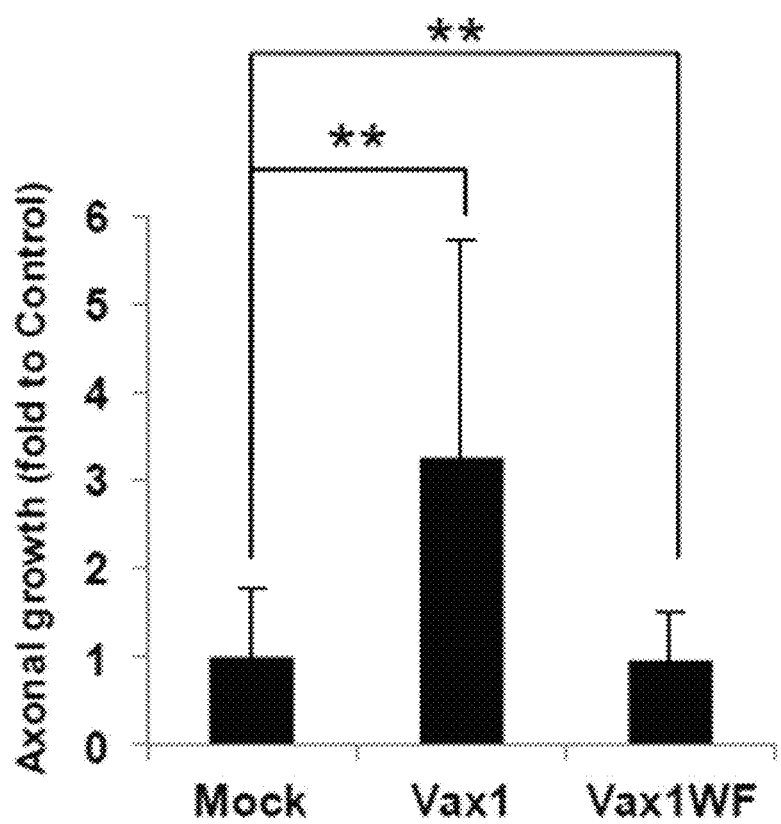
[Figure 13d]

[Figure 14a]
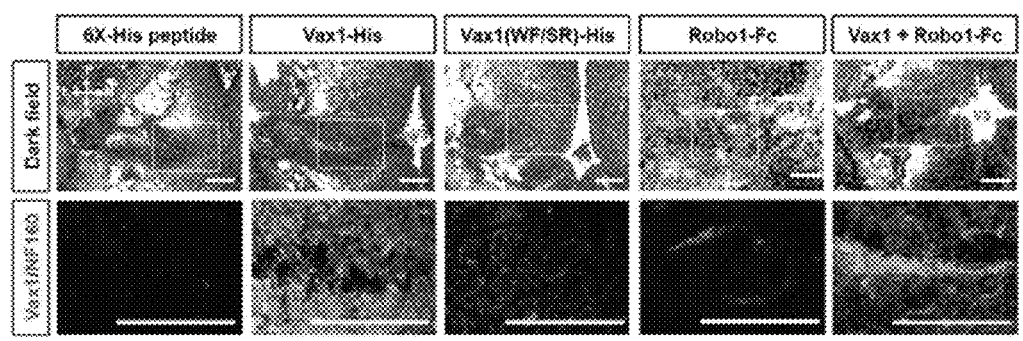
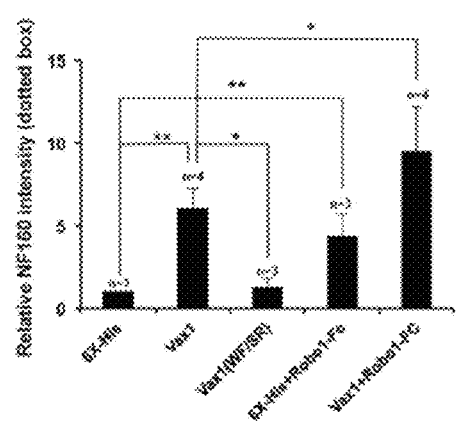

[Figure 14b]
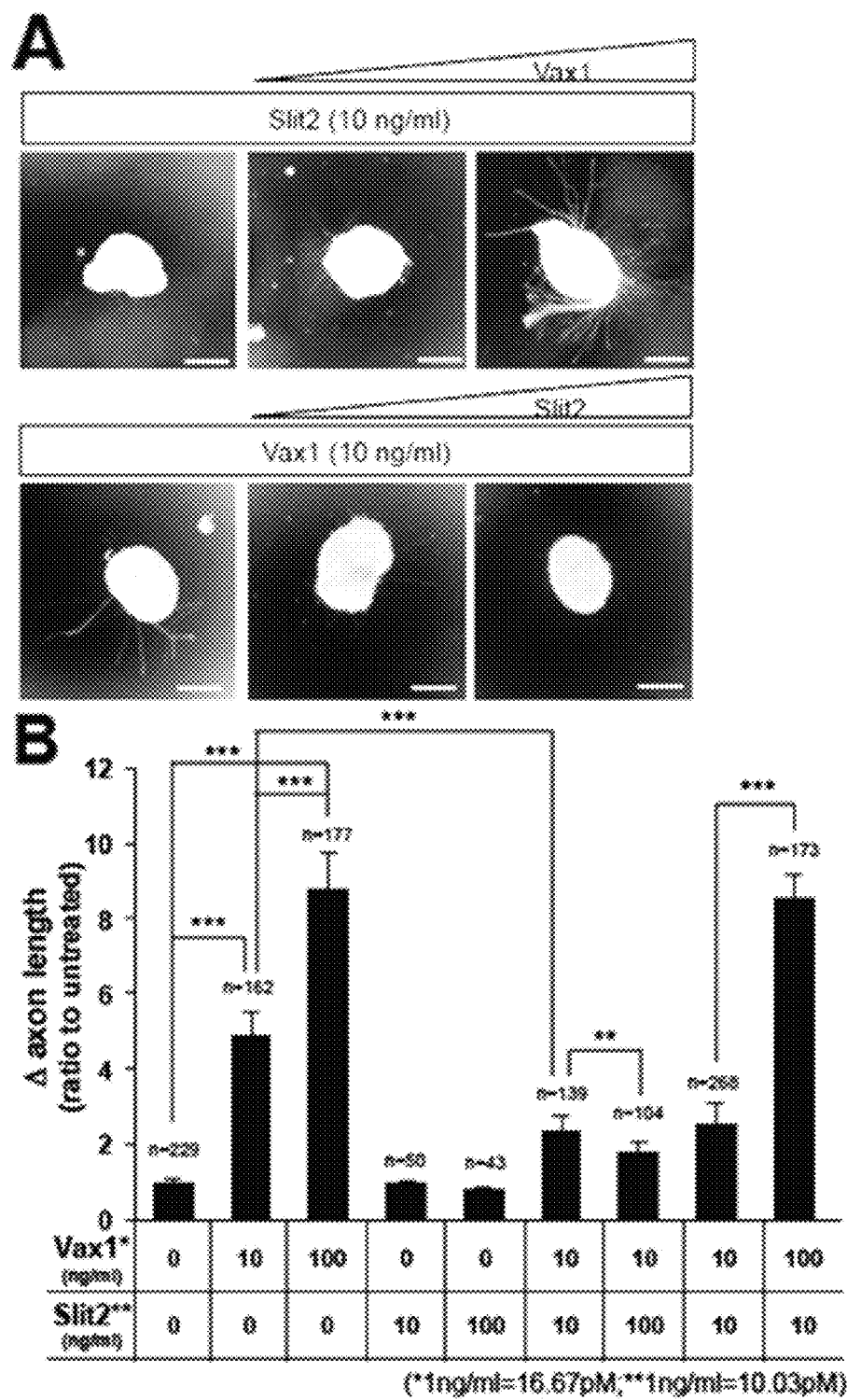

[Figure 14c]
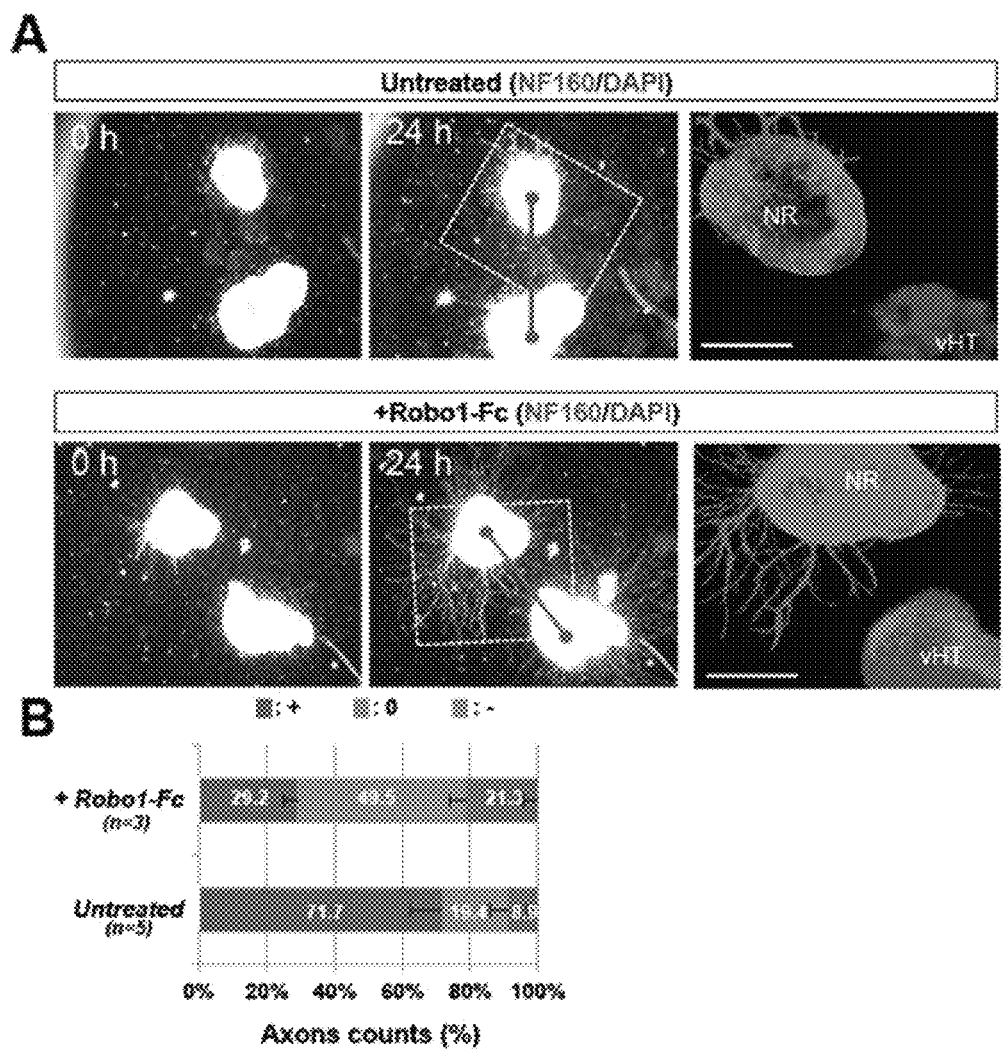

[Figure 14d]
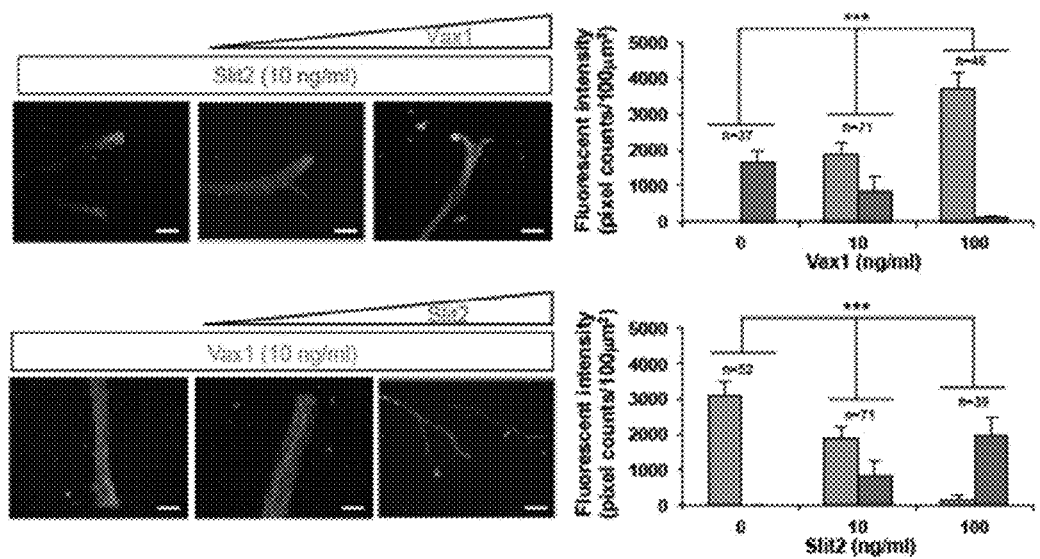

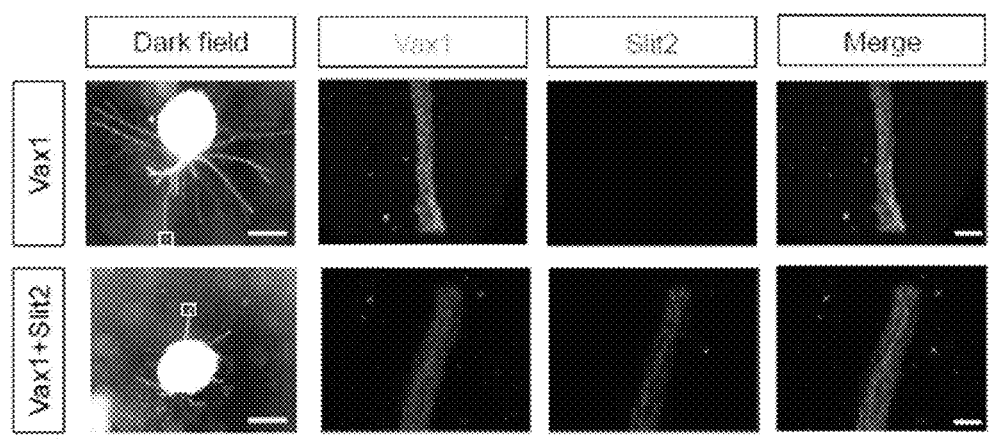
[Figure 14e]

[Figure 14f]
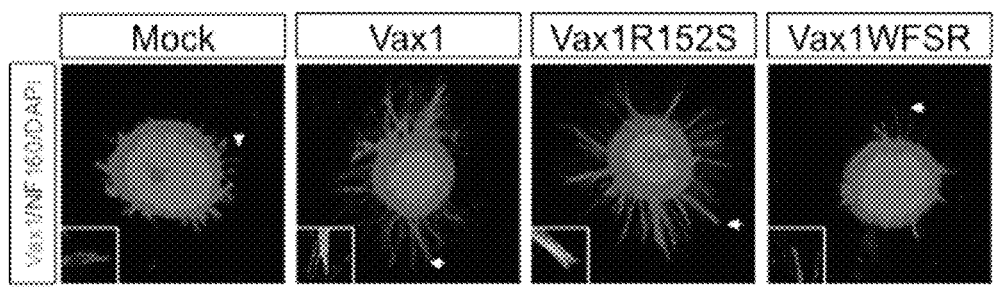

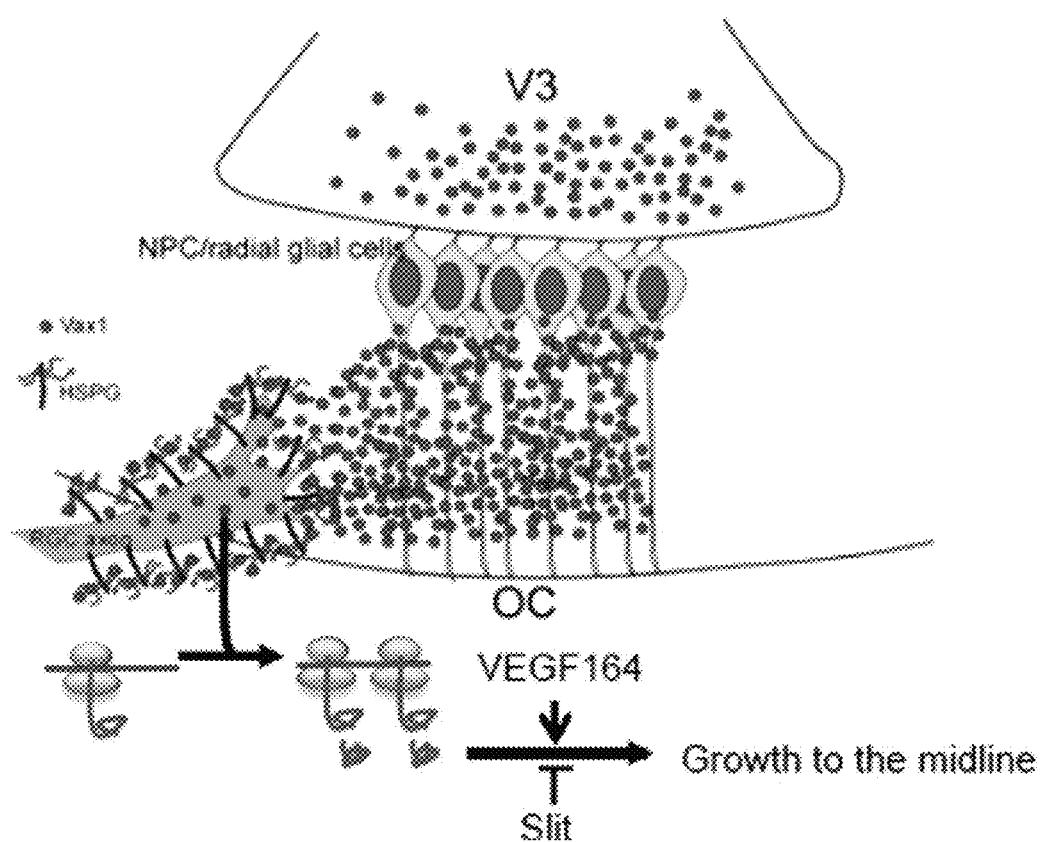
[Figure 14g]

SEQUENCE LISTING

<160> NUMBER OF SEQ ID NOS: 4

<210> SEQ ID NO 1
<211> LENGTH: 338
<212> TYPE: PRT
<213> ORGANISM: Mus musculus

<400> SEQUENCE: 1

```
Met Phe Gly Lys Pro Asp Lys Met Asp Val Arg Cys His Ser Asp Thr
1               5                   10                  15

Glu Ala Ala Arg Val Ser Lys Asn Ala His Lys Glu Ser Arg Glu Ile
            20                  25                  30

Lys Gly Ala Glu Gly Ser Leu Pro Ala Ala Phe Leu Lys Glu Pro Gln
        35                  40                  45

Gly Ala Phe Ser Gly Ser Gly Ala Ser Glu Asp Cys Asn Lys Ser Lys
    50                  55                  60

Ser Asn Ser Ser Ala Asp Pro Asp Tyr Cys Arg Arg Ile Leu Val Arg
65                  70                  75                  80

Asp Ala Lys Gly Ser Ile Arg Glu Ile Ile Leu Pro Lys Gly Leu Asp
                85                  90                  95

Leu Asp Arg Pro Lys Arg Thr Arg Thr Ser Phe Thr Ala Glu Gln Leu
            100                 105                 110

Tyr Arg Leu Glu Met Glu Phe Gln Arg Cys Gln Tyr Val Val Gly Arg
        115                 120                 125

Glu Arg Thr Glu Leu Ala Arg Gln Leu Asn Leu Ser Glu Thr Gln Val
    130                 135                 140

Lys Val Trp Phe Gln Asn Arg Arg Thr Lys Gln Lys Lys Asp Gln Gly
145                 150                 155                 160

Lys Asp Ser Glu Leu Arg Ser Val Val Ser Glu Thr Ala Ala Thr Cys
                165                 170                 175

Ser Val Leu Arg Leu Leu Glu Gln Gly Arg Leu Leu Ser Pro Pro Gly
            180                 185                 190

Leu Pro Ala Leu Leu Pro Pro Cys Ala Thr Gly Ala Leu Gly Ser Ala
        195                 200                 205

Leu Arg Gly Pro Ser Leu Pro Ala Leu Gly Ala Gly Ala Ala Ala Gly
```

```
              210                 215                 220
Ser Ala Ala Ala Ala Ala Ala Ala Thr Ala Pro Gly Pro
225                 230                 235                 240

Ala Gly Ala Ala Ser Gln His Gln Pro Ala Val Gly Gly Ala Pro Gly
                245                 250                 255

Pro Gly Pro Ala Gly Pro Gly Gly Leu His Ala Gly Ala Pro Thr Ala
                260                 265                 270

Ser His Gly Leu Phe Ser Leu Pro Val Pro Ser Leu Leu Gly Ser Val
                275                 280                 285

Ala Ser Arg Leu Ser Ser Ala Pro Leu Thr Met Ala Gly Ser Leu Ala
                290                 295                 300

Gly Asn Leu Gln Glu Leu Ser Ala Arg Tyr Leu Ser Ser Ala Phe
305                 310                 315                 320

Glu Pro Tyr Ser Arg Thr Asn Asn Lys Glu Gly Ala Glu Lys Lys Ala
                325                 330                 335

Leu Asp

<210> SEQ ID NO 2
<211> LENGTH: 292
<212> TYPE: PRT
<213> ORGANISM: Mus musculus

<400> SEQUENCE: 2

Met Gly Asp Gly Gly Ala Glu Arg Asp Arg Gly Pro Lys Arg Arg Glu
1               5                   10                  15

Glu Pro Gly Gly Arg Ser Gly Arg His Gly Glu His Arg Gly Ala Glu
                20                  25                  30

Asp Leu Arg Ala Asp Thr Gly Ser Ala Ser Pro Arg Glu Ile Ala Gly
            35                  40                  45

Thr Ser Ala Ser Ser Pro Ala Gly Ser Arg Glu Ser Gly Gly Asp Ser
50                  55                  60

Asp Gly Gln Gln Ala Leu Gly Glu Thr Asp His Cys Arg Arg Ile Leu
65                  70                  75                  80

Val Arg Asp Ala Lys Gly Thr Ile Arg Glu Ile Val Leu Pro Lys Gly
                85                  90                  95

Leu Asp Leu Asp Arg Pro Lys Arg Thr Arg Thr Ser Phe Thr Ala Glu
                100                 105                 110

Gln Leu Tyr Arg Leu Glu Met Glu Phe Gln Arg Cys Gln Tyr Val Val
            115                 120                 125

Gly Arg Glu Arg Thr Glu Leu Ala Arg Gln Leu Asn Leu Ser Glu Thr
130                 135                 140

Gln Val Lys Val Trp Phe Gln Asn Arg Arg Thr Lys Gln Lys Lys Asp
145                 150                 155                 160

Gln Ser Arg Asp Leu Glu Lys Arg Ala Ser Ser Ala Ser Glu Ala
                165                 170                 175

Phe Ala Thr Ser Asn Val Leu Arg Leu Leu Gln Gly Arg Leu Leu
            180                 185                 190

Ser Val Pro Arg Ala Pro Ser Leu Leu Ala Leu Thr Pro Gly Leu Pro
                195                 200                 205

Gly Leu Pro Ala Ser His Arg Gly Thr Ser Leu Val Asp Pro Arg Asn
                210                 215                 220

Ser Ser Pro Arg Leu Asn Pro Met Pro Ser Ala Ser Ala Ser Ser Pro
225                 230                 235                 240

Leu Pro Pro Pro Leu Pro Ala Ile Cys Phe Ser Ser Ala Pro Leu Leu
```

-continued

```
                245                 250                 255
Asp Leu Pro Ala Gly Tyr Lys Leu Gly Ser Ser Ala Phe Glu Pro Tyr
            260                 265                 270

Ser Arg Leu Glu Gln Gln Lys Val Gly Ser Pro Gly Gln Ser Asp Lys
        275                 280                 285

Lys Ala Asp Ile
    290

<210> SEQ ID NO 3
<211> LENGTH: 12
<212> TYPE: PRT
<213> ORGANISM: Mus musculus

<400> SEQUENCE: 3

Arg Lys Gln Arg Arg Glu Arg Thr Thr Phe Thr Arg
1               5                   10

<210> SEQ ID NO 4
<211> LENGTH: 12
<212> TYPE: PRT
<213> ORGANISM: Mus musculus

<400> SEQUENCE: 4

Lys Arg Thr Arg Thr Ser Phe Thr Ala Glu Gln Leu
1               5                   10
```

NERVE REGENERATING OR NERVE GROWTH-PROMOTING PHARMACEUTICAL COMPOSITION CONTAINING VAX PROTEIN AS ACTIVE INGREDIENT

CROSS REFERENCE TO RELATED APPLICATIONS

This is a continuation of PCT Application No. PCT/KR2014/011208, filed on Nov. 20, 2014, which is incorporated by reference, and which claims priority to Korean Application No. 10-2014-0158645, filed on Nov. 14, 2014 and Korean Application No. 10-2013-0141193, filed on Nov. 20, 2013.

BACKGROUND

1. Field of the Invention

The present invention relates to a pharmaceutical composition for regeneration of nerves or acceleration growth of axons comprising Vax protein as an active ingredient, and a method for screening candidates for the regeneration of nerves or acceleration growth of axons by using Vax protein.

2. Description of the Related Art

The binocular visual system of mammals is formed by the topographic synaptic connection between the neurons of dorsal lateral geniculate nucleus (dLGN) and superior colliculus (SC) and the retinal ganglion cell (RGC) axon. In order for the retinal ganglion cell axon to contact with the target synapse, it recognizes neuroaxon growth guidance cues expressed in optic pathway structure including optic disc (OD), optic stalk (OS), optic chiasm (OC), and optic tract (OT), and then the axon is growing out of retina to the selected direction (Lemke and Reber, 2005; Petros et al., 2008). The said retinal ganglion cell axon guidance cues are exemplified by the cell surface ligands such as semaphorin existing in optic stalk and ephrinB2 exiting in optic chiasm; or the secreted factors such as netrin-1 existing in optic disc and Slit1 existing in optic chiasm (Erskine and Herrera, 2007). However, approximately only 3% of the retinal ganglion cell axon originated from the ventral and temporal areas of mouse retina proceeds to the ipsilateral hemisphere and the rest of it proceeds to the contralateral hemisphere across the midline of ventral hypothalamus where optic chiasm resides.

Ventral hypothalamus cells express those molecules that are responsible for the determination of the direction of retinal ganglion cell axon progress in optic chiasm. For example, ventral hypothalamus radial glial cells express ephrinB2 that binds to EphB1 receptor expressed in the ventral-temporal retinal ganglion cell axon to make the axon heading for ipsilateral optic track retreat (Nakagawa et al., 2000; Williams et al., 2003). In the meantime, the vascular endothelial growth factor 164 (VEGF164) and neuronal cell adhesion molecule (NrCAM) expressed in ventral hypothalamus bind to Neurophilin 1 and Plexin A1 respectively to induce the growth of retinal ganglion cell axon across the ventral hypothalamus midline (Erskine et al., 2011; Kuwajima et al., 2012; Williams et al., 2006). The retinal ganglion cell axon has to pass the ventral-lateral diencephalic area highly expressing repulsive signals such as Slit and sephaphorin in order to receive the direction guidance signals from those molecules in optic chiasm (Erskine and Herrera, 2007). However, those molecules of ventral diencephalic area that induce retinal ganglion axon to grow to the direction of midline with overcoming the repulsive signals have not been identified, yet.

Vax1 (ventral anterior homeobox 1) is a homeodomain transcription factor expressed in various ventral-medial forebrain originated structures including medial and lateral geniculate eminence (MGE and LGE), ventral septum, anterior entopeduncular area (AEP), preoptic area (POA), ventral hypothalamus, and optic disc (Bertuzzi et al., 1999; Hallonet et al., 1998). The genetic malfunction of Vax1 in human and mouse causes not only coloboma of the eye but also agenesis of multiple midline structures of the brain including anterior commissure, corpus callosum, and optic chiasm (Bertuzzi et al., 1999; Hallonet et al., 1999; Slavotinek et al., 2012). In a Vax1 knock out mouse, the retinal ganglion cell axon can grow over optic disc but cannot reach ventral hypothalamus and at last fails in the formation of optic chiasm. Vax1 plays an important role in the growth and fasciculation of retinal ganglion cell axon, but is not expressed in retinal ganglion cells (Bertuzzi et al., 1999).

SUMMARY OF THE INVENTION

The present inventors searched for a molecule that can be function or mediate the growth of retinal ganglion cell axon. The inventors confirmed that Vax1 was secreted in the ventral hypothalamus explant separated from a mouse and the secreted Vax1 could bind to the extracellular sugar group of heparan sulfate proteoglycans (HSPGs) existing in the retinal ganglion cell axon of the retinal explant co-cultured with the above, so that the Vax1 conjugate invaded in the axonplasm and then activated the local protein synthesis therein to accelerate the growth of retinal ganglion cell axon. Therefore, the inventors at last completed this invention by confirming that the Vax1 protein could be effectively used for a pharmaceutical composition for the acceleration of the regeneration or growth of axons including retinal ganglion cells.

It is an object of the present invention to provide a pharmaceutical composition for regeneration of nerves or acceleration growth of axons comprising Vax protein as an active ingredient.

To achieve the above object, the present invention provides a pharmaceutical composition for the regeneration of nerves or acceleration growth of axons comprising Vax protein as an active ingredient.

The present invention also provides a pharmaceutical composition for regeneration of nerves or acceleration growth of axons comprising a vector or cell containing the polynucleotide encoding Vax protein as an active ingredient.

The present invention also provides a method for screening the candidate materials for regeneration of nerves or acceleration growth of axons comprising the following steps:

1) treating the cells obtained from a test subject with the test samples and measuring the growth of neuroaxon;

2) measuring the intensity of binding between Vax1 and heparan sulfate proteoglycans in the cells of step 1); and 3) selecting those test samples that are able to increase the binding intensity between Vax1 and heparan sulfate proteoglycans of step 2), compared with that of the non-treated control.

The present invention also provides a method for regenerating nerves containing the step of administering a pharmaceutically effective dose of Vax protein to a subject having neuronal and axonal damage.

The present invention also provides a method for accelerating the growth of axons containing the step of administering a pharmaceutically effective dose of Vax protein to a subject having neuronal and axonal damage.

The present invention also provides a method for regenerating nerves containing the step of administering a pharmaceutically effective dose of a vector or cell comprising the polynucleotide encoding Vax protein to a subject having neuronal and axonal damage.

The present invention also provides a method for accelerating the growth of axons containing the step of administering a pharmaceutically effective dose of a vector or cell comprising the polynucleotide encoding Vax protein to a subject having neuronal and axonal damage.

The present invention also provides an use of the Vax protein for a pharmaceutical composition for regenerating nerves or accelerating growth of axons.

In addition, the present invention provides an use of the vector or cell harboring the polynucleotide encoding Vax protein for a pharmaceutical composition for regenerating nerves or accelerating growth of axons.

Advantageous Effect

The present invention relates to a pharmaceutical composition for regenerating nerves or accelerating growth of axons comprising Vax protein as an active ingredient. Precisely, Vax1 is secreted in the ventral hypothalamus (vHT) explant separated from a mouse embryo. The secreted Vax1 combines with extracellular sugar group of heparan sulfate proteoglycans (HSPGs) existing in retinal ganglion cell (RGC) axon of the retinal explant co-cultured so as for the complex invades into axonplasm. Then, the Vax1 conjugated with the sugar group activates the local protein synthesis to accelerate the growth of retinal ganglion cell axon. Therefore, the secreted Vax protein can be effectively used as an active ingredient of a composition for regenerating nerves or accelerating growth of axons.

BRIEF DESCRIPTION OF THE DRAWINGS

The application of the preferred embodiments of the present invention is best understood with reference to the accompanying drawings, wherein:

FIGS. 1a-1b. FIG. 1a is a diagram illustrating the expression of Vax1 protein in the neural progenitor cells (NPC) of the Vax1 normal mouse (Vax1+/+) at 13.5 days of the embryonic stage (E 13.5) and the Vax1 knock-out mouse (Vax1−/−) and in the post-mitotic neuronal cells.

FIG. 1b is a diagram illustrating the expression of Vax1 protein in the optic chiasm (OC) forming cells of E13.5 Vax1+/+ mouse and Vax1−/− mouse.

FIGS. 2a-2e. FIG. 2a is a schematic diagram illustrating the method of measuring the direction of retinal ganglion cell (RGC) axon progress.

FIG. 2b is a diagram illustrating the retinal ganglion cell axon growing in the neural retina (NR) explant co-cultured with the ventral hypothalamus (vHT) separated from E13.5 Vax 1+/+ or Vax 1 −/− mouse.

FIG. 2c is a diagram illustrating the direction where the retinal ganglion cell axon tip is pointing that is toward the ventral hypothalamus, observed in the neural retina explant co-cultured with the ventral hypothalamus (vHT) separated from E13.5 Vax 1+/+ or Vax 1 −/− mouse:
WT: Vax1+/+; and
KO: Vax1−/−.

FIG. 2d is a diagram illustrating the direction where the retinal ganglion cell axon shaft is pointing that is toward the ventral hypothalamus, observed in the neural retina explant co-cultured with the ventral hypothalamus (vHT) separated from E13.5 Vax 1+/+ or Vax 1 −/− mouse:
WT: Vax1+/+; and
KO: Vax1−/−.

FIG. 2e is a diagram illustrating the defect in the ventral hypothalamus and retinal ganglion cell axon separated from E13.5 Vax1+/+ or Vax1−/− mouse:
Vegfa: vascular endothelial growth factor, VEGF164;
ISH: In situ hybridization;
NrCAM: neuronal cell adhesion molecule; and
IF: immunofluorescence staining (scale bar: 100 µm).

FIGS. 3a-3c. FIG. 3a is a diagram illustrating the retinal ganglion cell axon growing in the neural retina explant co-cultured with the COS7 cells over-expressing Vax1, transcription inactive Vax1 mutant (Vax1(R152S)), and Vax2.

FIG. 3b is a diagram illustrating the growth direction of the retinal ganglion cell axon toward COS7 cells in the neural retina explant co-cultured with the COS7 cells over-expressing Vax1, transcription inactive Vax1 mutant (Vax1 (R152S)), and Vax2.

FIG. 3c is a diagram illustrating the detection of Vax protein in the growth medium of the COS7 cells over-expressing Vax1, transcription inactive Vax1 mutant (Vax1 (R152S)), and Vax2.

FIGS. 4a-4e. FIG. 4a is a diagram illustrating the location of Vax protein in the COS7 cells (right) treated with the growth medium of the HEK293T cells (left) over-expressing Vax1, GFP-Vax1, and GFP-Vax2:
▶: normal COS7 cells immunostained with GFP; and
→: dead cell debris immunostained with GFP.

FIG. 4b is a diagram illustrating the Vax1 protein existing in the third ventricle of the E13 mouse injected with the growth medium of the HEK293T cells over-expressing Myc-Vax1:
▶: cells expressing Myc-Vax1.

FIG. 4c is a diagram illustrating the Vax1 protein existing in the cell lysate (CL) and growth media (GM) of ventral hypothalamus explant of E14.5 normal mouse and Vax1−/− mouse.

FIG. 4d is a diagram illustrating the Vax1 protein existing in the cell lysate (CL) of ventral hypothalamus explant, the supernatant (S3) of E14.5 mouse cerebrospinal fluid (CSF), and the dead cell debris (P2).

FIG. 4e is a diagram illustrating the retinal ganglion cell axon that is growing toward COS7 in the neural retina (NR) explant co-cultured with COS7 cells after treated with pre-immune rabbit immunoglobulin (rbIgG) and rabbit anti-Vax1 polyclonal antibody (α-Vax1) in order to investigate the function of Vax1 secreted in the COS7 cells over-expressing Vax1 in association with the inducement of growth of the retinal ganglion cell axon:
→: where the tagged mouse Vax1 exists (scale bar: 500 µm (left), scale bar: 100 µm (right)).

FIGS. 5a-5g. FIG. 5a is a diagram illustrating the retinal ganglion cell axon that is growing toward ventral hypothalamus explant in the neural retina (NR) explant co-cultured with the ventral hypothalamus (vHT) explant after treated with pre-immune rabbit immunoglobulin (rbIgG), rabbit anti-Vax1 polyclonal antibody (α-Vax1), and rabbit anti-Vax2 polyclonal antibody (α-Vax2):

→: magnified area, wherein when Vax1 (green) is distributed in the retinal ganglion cell axon labeled with NF160 (red), the two colors are over-lapped and changed into yellow (scale bar: 500 μm).

FIG. 5b is a diagram illustrating the direction of the retinal ganglion cell axon growing toward ventral hypothalamus (vHT) explant in the neural retina (NR) explant co-cultured with the ventral hypothalamus (vHT) explant after treated with pre-immune rabbit immunoglobulin (rbIgG), rabbit anti-Vax1 polyclonal antibody (α-Vax1), and rabbit anti-Vax2 polyclonal antibody (α-Vax2).

FIG. 5c is a diagram illustrating the number and the thickness of the retinal ganglion cell axon growing toward ventral hypothalamus (vHT) explant in the neural retina (NR) explant co-cultured with the ventral hypothalamus (vHT) explant after treated with pre-immune rabbit immunoglobulin (rbIgG), rabbit anti-Vax1 polyclonal antibody (α-Vax1), and rabbit anti-Vax2 polyclonal antibody (α-Vax2).

FIG. 5d is a diagram illustrating that the retina explant was added with the peptide (100 ng/ml) labeled with 6X-His and fluorescein isothiocyanate (FITC) or the recombinant protein (500 ng/ml) labeled with His tagged Vax1 and FITC, followed by culture:
▶: magnified area.

FIG. 5e is a diagram illustrating the immunostaining of the retina explant cultured after treated with 6X-His peptide (100 ng/ml) or Vax1-His-FITC protein (500 ng/ml):
→: location of Vax1 and His protein.

FIG. 5f is a diagram illustrating the measurement of the length of the axon 24 hours after the treatment with 6X-His peptide (25 ng/ml, white rod) or Vax1-His protein (100 ng/ml, black rod) in the quadrant of the retina explant:
DN: Dosal Nasal;
DT: Dosal Temporal;
VN: Ventral Nasal; and
VT: Ventral Temporal.

FIG. 5g (top) is a diagram illustrating the immunostaining of the retina explant cultured for 24 hours with or without the addition of His-tagged Vax2 (100 ng/ml), and FIG. 5g (bottom) is a graph illustrating the length of the retinal ganglion cell axon:
→: location of Vax2-His (scale bar: 500 μm (upper part), scale bar: 100 μm (lower part)).

FIGS. 6a-6d. FIG. 6a is a diagram illustrating the growth of the retinal ganglion cell axon in the E13.5 mouse third ventricle (V3) injected with pre-immune rabbit immunoglobulin (rbIgG) and rabbit anti-Vax1 polyclonal antibody (α-Vax1):
A: anterior;
P: posterior;
M: medial;
L: lateral; and
*: optic chiasm.

FIG. 6b is a diagram illustrating the retinal ganglion cell axon growing in the neural retina explant treated with Vax1 recombinant protein, or Vax1 recombinant protein and rabbit anti-Vax1 polyclonal antibody (α-Vax1):
→: magnified area, wherein when Vax1 (green) is distributed in the retinal ganglion cell axon labeled with NF160 (red), the two colors are over-lapped and changed into yellow (scale bar: 500 μm).

FIG. 6c is a diagram illustrating the time dependent length of the retinal ganglion cell axon in the neural retina explant treated with Vax1 recombinant protein, or Vax1 recombinant protein and rabbit anti-Vax1 polyclonal antibody (α-Vax1).

FIG. 6d is a diagram illustrating the number, the thickness, and the length of the retinal ganglion cell axon in the neural retina explant treated with Vax1 recombinant protein, or Vax1 recombinant protein and rabbit anti-Vax1 polyclonal antibody (α-Vax1).

FIGS. 7a-7e. FIG. 7a is a diagram illustrating the expression of Vax1 mRNA in the retina of Vax1+/+ mouse and Vax1lacZ/lacZ E14.5 mouse.

FIG. 7b is a diagram illustrating the expressions of Vax1 protein and β-galactosidase (β-gal) in the optic pathway structure of Vax1+/lacZ mouse and Vax1lzcZ/lacZ E14.5 mouse:
GCL: ganglion cell layer; and
NBL: neuroblast layer.

FIG. 7c is a diagram illustrating the Vax1 protein existing in the retina of Vax1+/+ mouse and Vax1lacZ/lacZ E14.5 mouse:
▶: the area immunostained with NF160 (neurofilament), the retinal ganglion cell axon marker; and
→: the area immunostained with NF160 and Vax1.

FIG. 7d is a diagram illustrating the Vax1 protein existing in the retina and optic nerve of Vax1+/+ mouse and Vax1lacZ/lacZ E18.5 mouse:
RGC: retinal ganglion cell;
OS APC: optic disc astrocyte precursor cell;
▶ in RGC: Vax1 protein in endocytic vesicle; and
→ in RGC: Vax1 protein conjugated onto the extracellular surface of plasma membrane of RGC;
▶ in OS APC: Vax1 protein in trafficking vesicle trafficking vesicle; and
→ in OS APC: Vax1 protein associated with chromatin in the nucleus.

FIG. 7e (upper two rows, two digital images per row) is a diagram illustrating the Vax1 mRNA expression measured by performing in situ RNA hybridization with the brain section obtained from Vax1+/+ (WT) mouse and Vax1-/- E14.5 mouse by using [33P]-CTP-labeled antisense Vax1 probe according to the method presented in Mui et al., 2005. The radiation intensity of the probe was visualized. And FIG. 7e (lower two rows, three digital images per row) is a diagram illustrating the brain section obtained from E14.5 Vax1+/lacZ mouse and Vax1lacZ/lacZ mouse, which was visualized by immunostaining:
HCC: hypothalamic cell cord;
ON: optic nerve; and
OC: optic chiasm.

FIG. 8 is a diagram illustrating the distribution of the Vax1 protein labeled with the fluorescence protein and the red fluorescence protein (dsRed) in the imaginal disc of Ptc-gal4>Vax1-EGFP,Ds-Red *drosophila*, Ptc-gal4>Vax1-EGFP,Ds-Red,Sdc23 *drosophila*, Ptc-gal4>Vax1-EGFP,Ds-Red,Sdc *drosophila*, and Ptc-gal4>Vax1-EGFP,Ds-Red,Dlp *drosophila*.

FIGS. 9a-9f. FIG. 9a is a diagram illustrating the bond between Vax1 and syndecan2 (Sdc2) in the optic nerve of the mouse on the post-natal day 0, examined by co-immunoprecipitation.

FIG. 9b is a diagram illustrating the bond between Vax1 and syndecan1 (Sdc1) or syndecan2 (Sdc2) in the HEK293T cells over-expressing Vax1 and GFP-Sdc1 or GFP-Sdc2, examined by co-immunoprecipitation.

FIG. 9c is a diagram illustrating the bond between Vax2 and syndecan1 (Sdc1) or syndecan2 (Sdc2) in the HEK293T cells over-expressing Vax2 and GFP-Sdc1 or GFP-Sdc2, examined by co-immunoprecipitation.

FIG. 9d is a diagram illustrating the bond between Vax1 and Sdc2-N or Sdc2-C in the HEK293T cells over-expressing Vax1 and GFP-Sdc1-N or GFP-Sdc2-C, examined by co-immunoprecipitation.

FIG. 9e is a diagram illustrating the protein that binds to Vax1 in the optic nerve of the E14.5 mouse treated with heparin, examined by co-immunoprecipitation.

FIG. 9f is a diagram illustrating the bond between Vax1 protein and the sepharose 4B resin coated with heparan sulfate (HS) or CS.

FIGS. 10a-10c. FIG. 10a is a diagram illustrating the retinal ganglion cell axon growing in the neural retina explant treated with Vax1 protein, Vax1 protein and heparinase I, and Vax1 protein and chondroitinase ABC (Chnase-ABC):

→: magnified area, wherein when Vax1 (green) is distributed in the retinal ganglion cell axon labeled with NF160 (red), the two colors are over-lapped and changed into yellow (scale bar: 500 μm).

FIG. 10b is a diagram illustrating the retinal ganglion cell axon growing in the neural retina explant treated with Vax1 protein and Vax1 KR peptide (KR-bio) labeled with biotin encoding Vax1 amino acid sequence from the residue 101 to 112 displaying homology to Otx2 sugar binding motif, Vax1 protein and AA-bio peptide wherein the major two sugar binding residues 101 lysine and 102 arginine (Lys101-Arg102 (KR)) were substituted with alanine (Ala-Ala (AA)), or Vax1 (KR/AA) mutant protein with the substitution of Lys101-Arg102 (KR) with Ala-Ala (AA):

→: magnified area, wherein when Vax1 (green) is distributed in the retinal ganglion cell axon labeled with NF160 (red), the two colors are over-lapped and changed into yellow (scale bar: 500 μm).

FIG. 10c is a diagram illustrating the retinal ganglion cell axon growing in the neural retina explant treated with Vax1 protein, Vax1 protein and heparinase I, Vax1 protein and chondroitinase ABC, Vax1 protein and Vax1 KR-peptide (KR-bio), Vax1 protein and AA-bio peptide, and Vax1 (KR/AA) mutant protein.

FIGS. 11a-11c. FIG. 11a is a diagram illustrating the investigation of Vax1 protein in the growth medium of the HEK293T cells over-expressing Vax1 and Vax1 (KR/AA) treated with heparin by Western blotting.

FIG. 11b is a diagram illustrating the Vax1 protein binding to Sdc2 in the HEK293T cells over-expressing GFP-Sdc2 and Vax1 or Vax1 (KR/AA), investigated by co-immunoprecipitation.

FIG. 11c is a diagram illustrating the Vax1 protein existed in the COS7 cells added with the growth medium of the HEK293T cells over-expressing Myc-Vax1 or Myc-Vax1 (KR/AA).

FIGS. 12a-12d. FIG. 12a is a diagram illustrating the Vax1 protein binding to Sdc2 in the HEK293T cells over-expressing GFP-Sdc2, and Myc-Vax1 (WF/SR) mutant wherein the 147$^{th}$ residue tryptophan (Trip) and the 148$^{th}$ residue phenylalanine (Phe) (WR) displaying homology to the important residues involved in cell-invasion of antennapedia (Antp) were substituted with Ser-Arg (SR) or Myc-Vax1, investigated by co-immunoprecipitation.

FIG. 12b is a diagram illustrating the Vax1 protein existing in the COS7 cells added with the growth medium of the HEK293T cells over-expressing Myc-Vax1 or Myc-Vax1 (WF/SR), investigated by co-immunoprecipitation.

FIG. 12c is a diagram illustrating the retinal ganglion cell axon growing toward COS7 cells in the neural retina (NR) explant co-cultured with the COS7 cells over-expressing Myc-Vax1 or Myc-Vax1 (WF/SR).

FIG. 12d is a diagram illustrating the direction of the retinal ganglion cell axon heading to COS7 cells in the neural retina (NR) explant co-cultured with the COS7 cells over-expressing Myc-Vax1 or Myc-Vax1 (WF/SR).

FIGS. 13a-13d. FIG. 13a is a diagram illustrating the formation of Vax1 protein complex in the cytoplasm fraction of the HEK293T cells over-expressing GST and GST-Vax1.

FIG. 13b is a diagram illustrating the newly synthesized protein in the neural retina explant cultured in the medium containing Vax1 or Vax1 (WF/SR) protein, confirmed by using a green fluorescence.

FIG. 13c is a diagram illustrating the newly synthesized protein in the axon separated from the neural retina explant cultured in the medium containing Vax1 or Vax1 (WF/SR) protein, confirmed by using a green fluorescence.

FIG. 13d is a diagram illustrating the growth of the axon separated from the neural retina explant cultured in the medium containing Vax1 or Vax1 (WF/SR) protein.

FIGS. 14a-14g. FIG. 14a (A) is a diagram illustrating the growth of the retinal ganglion cell axon in the third ventricle of the Vax1lacZ/lacZ mouse embryo injected with His-peptide, Vax1-His, Vax1(WF/SR)-His, and Robo1-Fc explant, examined by immunostaining, and FIG. 14a (B) is a graph illustrating the fluorescence intensity thereof.

FIG. 14b (A) is a diagram illustrating the retinal ganglion cell axon growing in the neural retina explant treated with both Vax1 and Slit2 at different concentrations, and FIG. 14b (B) is a graph illustrating the length of the retinal ganglion cell axon growing in the neural retina explant treated with both Vax1 and Slit2 at different concentrations.

FIG. 14c (A) is a diagram illustrating that the neural retina explant of E13.5 mouse and the ventral hypothalamus explant of Vax1 knock-out mouse were co-cultured in the presence or absence of Robo 1-Fc for 24 hours, followed by visualization and immunostaining, and FIG. 14c (B) is a graph illustrating the direction of the retinal ganglion cell axon:

+: forward;

0: neutral; and

−: reverse.

FIG. 14d is a graph illustrating the fluorescence intensity of the immunostained retinal ganglion cell axon growing in the neural retina explant treated with both Vax1 and Slit together at different concentrations (scale bar: 20 μm).

FIG. 14e is a diagram illustrating the Vax1 protein invading in the retinal ganglion cell axon in the neural retina explant treated with Vax1, or Vax1 and Slit2.

FIG. 14f is a diagram illustrating the Vax1 protein invading in the cortical explant axon treated with Vax1, Vax1 (R152S) and Vax1 (WF/SR), confirmed by immunofluorescent staining.

FIG. 14g is a schematic diagram illustrating the growth regulation model of the retinal ganglion cell axon by the secreted Vax1 protein.

SEQUENCE LISTING

The Sequence Listing is submitted as an ASCII text file [7037-96982-01_Sequence_Listing.txt, May 18, 2016, 6.20 KB], which is incorporated by reference herein.

DETAILED DESCRIPTION OF SEVERAL EMBODIMENTS

Hereinafter, the present invention is described in detail.

The present invention provides a pharmaceutical composition for regenerating nerves or accelerating growth of axons comprising Vax (ventral anterior homeobox) protein as an active ingredient The said Vax protein is preferably selected from the group consisting of Vax1 protein comprising the amino acid sequence represented by SEQ. ID. NO: 1 and Vax2 protein comprising the amino acid sequence represented by SEQ. ID. NO: 2, but not always limited thereto.

The said neuron is preferably selected from the group consisting of Vax1 deficient optic nerve, cortical commissural nerve, hippocampal commissural nerve, hypothalamic commissural nerve, and trigeminal nerve, but not always limited thereto.

The said Vax1 herein preferably binds to heparan sulfate proteoglycan (HSPG), but not always limited thereto.

In a preferred embodiment of the present invention, the present inventors constructed Vax2lacZ/+ and vax1lacZ/lacZ knock-in and Vax1−/− knock-out mice in order to investigate the functions of Vax1 protein in association with the growth of the retinal ganglion cell axon. The neural retina (NR) explant and the ventral hypothalamic (vHT) explant were separated from the constructed mice, followed by culture. Also, Vax1 over-expressing Ptc-Gal4>UAS-Vax1-EGFP,UAS-DsRed;+, Ptc-Gal4>UAS-Vax1-EGFP,UAS-DsRed;Sdc23, Ptc-Gal4>UAS-Vax1-EGFP,UAS-DsRed; Sdc, and Ptc-Gal4>UAS-Vax1-EGFP,UAS-DsRed;Dlp *drosophilas* were constructed.

To investigate the effect of Vax1 on optic pathway structure, the present inventors performed immunostaining with the optic chiasm forming cells of Vax1+/+ (WT) and Vax1−/− mice. As a result, Vax1 was found in Sox2 (SRY box2) positive neural stem cells and nestin (RC2) positive radial glial cells. Neural stem cells and radial glial cells, the optic chiasm forming cells, were normally growing in Vax1−/− mouse. That is, Vax1 is expressed in the optic chiasm existing in neural stem cells and radial glial cells, and the abnormal development of optic chiasm in Vax1−/− mouse was not attributed to the mal-formation of the ventral hypothalamic cells associated with the formation of optic chiasm (see FIG. 1a and FIG. 1b).

To investigate the effect of Vax1 on the development of optic chiasm, the present inventors co-cultured the neural retina explant and the ventral hypothalamus explant obtained from E13.5 Vax1+/+ (WT) mouse and Vax1−/− (KO) mouse and then observed the growth of the retinal ganglion cell axon and investigated the direction of the growth. As a result, it was observed that the number of the retinal ganglion cell axon that was growing toward the Vax1−/− (KO) ventral hypothalamic explant in the Vax1+/+ (WT) neural retina explant was decreased, suggesting that the Vax1 originated from the ventral hypothalamic explant induced directly or indirectly the growth of the retinal ganglion cell axon in the retina. Therefore, it was confirmed that Vax1 could regulate the growth of the retinal ganglion cell axon with the axon inducing molecules secreted via non-cell autonomous method (see FIGS. 2a~2e).

To investigate the effect of the transcriptional activity of Vax1 on the growth of the retinal ganglion cell axon, the present inventors performed immunostaining with Vax1, transcription inactive VAx1 mutant (Vax1 (R152S)), and the COS7 cells over-expressing Vax2 sharing homeodomain with Vax1, measuring the growth direction of the retinal ganglion cell axon therein, and western blotting with the protein included in the medium. As a result, the number of the retinal ganglion cell axon that was growing toward the COX7 cells over-expressing Vax1 and Vax1 (R152S) in the neural retina explant was significantly increased, compared with that of the control. Interestingly, Vax1 and Vax2 (R152S) proteins were observed in the retinal ganglion cell axon that did not express them on their own. Vax1 and Vax1 (R152S) proteins were also observed in the cell lysate (cell lysate, CL) of the COS7 cells over-expressing Vax1 and Vax1 (R152S) and the growth media (GM) thereof, suggesting that Vax1 secreted extracellularly and induced the growth of the retinal ganglion cell axon regardless of the transcriptional activity (see FIG. 3a~FIG. 3c).

To investigate whether or not Vax1 was secreted in the course of inducing the growth of the retinal ganglion cell axon, the present inventors injected the growth media of the HEK293T cells over-expressing Vax1 and the COS7 cells added with the growth media of the HEK293T cells over-expressing Vax1 or Vax2 into the cerebral ventricle of E13.5 mouse, followed by immunostaining and Western blotting with the brain sections obtained therefrom. As a result, Vax1 protein in the growth medium of the HEK293T cells was found in the COS7 cells cultured in vitro and the ventral diencephalic (vDC) cultured in vivo. The Vax1 protein was also found in the cell lysate of the ventral hypothalamic explant and the growth medium thereof, and cerebrospinal fluid (CSF). Therefore, it was confirmed that the Vax1 protein is a protein secreted not only in vitro culture but also in vivo, and therefore it is a protein secreted in the ventral hypothalamus regardless of the transcriptional activity (see FIGS. 4a~4e).

To investigate whether or not the secreted Vax1 protein was the protein involved in inducing the growth of the retinal ganglion cell axon toward the ventral hypothalamic explant, the present inventors investigated the direction of the growth of the retinal ganglion cell axon and the length thereof in the neural retina explant and the ventral hypothalamic explant co-cultured in the isolation of extracellular Vax protein by using rabbit anti-Vax1 polyclonal antibody and anti-Vax2 polyclonal antibody. As a result, the number and the thickness of the retinal ganglion cell axon that was growing toward the ventral hypothalamic explant in the neural retina explant treated with anti-Vax1 antibody were decreased, suggesting that the extracellular Vax1 played an important role in fasciculation of the axon. From the result of the analysis using Vax1-His-FITC protein, it was confirmed that Vax1 could stimulate the growth of the retinal ganglion cell axon significantly. It was also confirmed that Vax2 induced the growth of the retinal ganglion cell axon as similarly as Vax1 did (see FIGS. 5a~5g).

To investigate the role of the extracellular Vax1 in the growth of the retinal ganglion cell axon in vivo, the present inventors performed the detection of DiI axon colourant and immunostaining with the E13.5 mouse brain section transplanted with anti-Vax1 polyclonal antibody in the third ventricle. As a result in the mouse transplanted with the anti-Vax1 polyclonal antibody, the retinal ganglion axon growing toward optic chiasm was decreased and the axon growth was stopped in the ventral diencephalic outer wall. It was also confirmed that the Vax1 protein distribution in the retinal ganglion cell axon was reduced.

The present inventors also performed immunostaining after treating Vax1 recombinant protein or anti-Vax1 polyclonal antibody to the culture medium of neural retina explant, followed by the measurement of the growth and the thickness of the retinal ganglion cell axon. As a result, the number, the thickness, and the length of the retinal ganglion cell axon were increased in the neural retina explant treated with Vax1 recombinant protein. In the meantime, the number, the thickness, and the length of the retinal ganglion axon were reduced in the neural retina explant treated with neural retina Vax1 recombinant protein and anti-Vax1 polyclonal antibody. From the above results, it was confirmed that the said recombinant Vax1 protein could directly stimulate the growth of the retinal ganglion cell axon (see FIGS. 6a~6d).

To investigate the expression of Vax1 mRNA and Vax1 protein in the retina, the present inventors performed in situ RNA hybridization with the retina and the brain sections obtained from Vax1+/+, Vax1lacZ/lacZ and Vax1+/lacZ mice. As a result, it was confirmed that Vax1 mRNA was found in optic disc (OD), optic stalk (OS), and preoptic area (POA) of the mouse eyeball and optic nerve except in the retina. The inventors also performed immunostaining with the eyeball section obtained from Vax1+/lacZ mouse expressing Vax1 and beta-galactosidase (lacZ) in each homologous chromosome by using anti-Vax1 polyclonal antibody and beta-galactosidase antibody. As a result, it was confirmed that Vax1 was expressed in optic disc (OS) astrocyte precursor cell (APC) of Vax1+/lacZ mouse expressing both Vax1 and beta-galactosidase at the same time. It was also confirmed that Vax1 was detected in the retinal ganglion cells that did not express beta-galactosidase. The inventors confirmed by immune electron microscopy performed to investigate the microdistribution of Vax1 protein in the cells that Vax1 protein was bound to the extracellular surface of the retinal ganglion cell plasma membrane in Vax1+/+ mouse and also found in the endocytic vesicles in the retinal ganglion cells. Therefore, it was confirmed that Vax1 was expressed and secreted in the optic stalk astrocytes, except in the retina, and the secreted Vax1 protein migrated into the retinal ganglion cells (see FIGS. 7a~7e).

To investigate whether or not syndecan (Sdc), the heparan sulfate proteoglycan (HSPG), played a certain role in the involvement of Vax1 in the regulation of intercellular migration, the inventors performed immunostaining with Vax1 over-expressing Ptc-Gal4>UAS-Vax1-EGFP,UAS-DsRed;+, Ptc-Gal4>UAS-Vax1-EGFP,UAS-DsRed;Sdc23, Ptc-Gal4>UAS-Vax1-EGFP,UAS-DsRed;Sdc, and Ptc-Gal4>UAS-Vax1-EGFP,UAS-DsRed;Dlp *drosophilas*. As a result in the *drosophila* expressing mutant syndecan, the number of cells expressing only Vax1 was increased in front of the imaginal disc that did not express red fluorescent protein co-expressed with Vax1-EGFP protein. In the meantime, in front of the imaginal disc co-expressing Dlp, the *drosophila* homologous protein to syndecan and HSPG glypican (Gip), with Vax1-EGFP and red fluorescent protein, the number of those cells expressing only Vax1 was reduced. The result above indicated that syndecan and Dlp were bound to Vax1 protein to interrupt the distribution of Vax1 in the neighboring cells and the intercellular migration of Vax1 was mediated by heparan sulfate proteoglycans (see FIG. 8).

To investigate the role of syndecan in the migration of Vax1, the present inventors performed immuno-precipitation and Western blotting with the optic nerve of the mouse at post-natal day 0 (P0) and the HEK293T cells over-expressing Vax1, syndecan 1 (Sdc1), syndecan 2 (Sdc2), N-terminal extracellular domain deficient Sdc2-C, and C-terminal domain deficient Sdc2-N. As a result, it was confirmed that Vax1 was precipitated by Sdc2 and Sdc2-N in the optic nerve and HEK293T cells, suggesting that the said Vax1 interacted with Sdc2, in particular with the extracellular domain of Sdc2 (see FIGS. 9a~9d).

To investigate whether or not Vax1 could bind to the side chain of heparan sulfate (HS) of Sdc2, the present inventors performed immuno-precipitation with the optic nerve of E14.5 mouse added with high concentration of heparin. As a result, it was confirmed that none of Sdc2, Sdc3, and Glp1 were precipitated, except Pax2 in the optic nerve treated with heparin. Vax1 protein was precipitated by HS-sepharose 4B resin coated with heparin. Therefore, it was confirmed that the Vax1 competed with heparin and was bound to the heparan sulfate side chain of the heparan sulfate proteoglycan protein (see FIGS. 9e and 9f).

To investigate whether or not the stimulation of the growth of the retinal ganglion cell axon by Vax1 was mediated by the Vax1 bond with heparin sugar chain, the present inventors treated Vax1 with heparinase I or chondroitinase ABC (ChnaseABC). As a result, it was confirmed that the growth of the retinal ganglion cell axon stimulated by Vax1 and the accumulation of Vax1 in the axon were suppressed by the treatment of heparinase I (see FIG. 10a).

To investigate whether or not the bond between Vax1 with heparan sulfate proteoglycans was mediated by Vax1 amino acid sequence ranging from the $101^{st}$ residue to the $112^{th}$ residue displaying the homology with Otx2 sugar binding motif, the present inventors performed immunostaining with the neural retina explant treated with Vax1 KR-peptide labeled with the biotin encoding the region above (KR-bio), AA-bio peptide wherein the two major sugar binding residues the $101^{st}$ lysine and the $102^{nd}$ arginine (Lys101-Arg102 (KR)) were substituted with alanine (Ala-Ala (AA)), or Vax1(KR/AA)-His mutant protein having the substitution of Lys101-Arg102 (KR) with Ala-Ala (AA), in order to measure the growth of the retinal ganglion cell axon. As a result, it was confirmed that the growth of the retinal ganglion cell axon was suppressed in the neural retina explant treated with KR-bio peptide. In the neural retina explant treated with Vax1 (KR/AA) mutant protein, the growth of the retinal ganglion cell axon was also suppressed. Therefore, it was confirmed that the Vax1 stimulated the growth of the retinal ganglion cell axon by binding with heparan sulfate using the sugar binding motif (see FIG. 10c).

To investigate the interaction between the secretion of Vax1 (KR/AA) mutant protein and syndecan2, the present inventors added heparin to the growth medium of the HEK293T cells over-expressing Vax1 or Vax1 (KR/AA). The levels of Vax1 and Vax1 (KR/AA) secreted in the growth medium were compared with those in the heparin free growth medium. The present inventors then performed immunoprecipitation and Western blotting using the HEK293T cells over-expressing Sdc2 and Vax1 or Vax1 (KR/AA). As a result, the interaction between Vax1 and Vax1 (KR/AA) protein and Sdc2 was confirmed (see FIG. 11b). The growth medium of the 293T cells over-expressing Vax1 or Vax1 (KR/AA) was added to COS7 cells, followed by immunostaining. As a result, Vax1 (KR/AA) could not migrate into the COS7 cells added with the growth medium of the HEK293T cells over-expressing Vax1 (KR/AA), indicating that the sugar binding motif of Vax1 was bound to heparan sulfate of heparan sulfate proteoglycans so that it could migrate into the retinal ganglion cell axon and induce the growth of the axon there (see FIG. 11c).

To investigate whether or not Vax1 could stimulate the growth of the retinal ganglion cell axon by regulating cytoplasm response after invading in the cells or whether or not Vax1 could activate the down stream signal of heparan sulfate proteoglycans so as to stimulate the growth of the retinal ganglion cell axon, the present inventors performed immuno-precipitation and Western blotting using the HEK293T cells over-expressing Vax1 or Vax1 (WF/SR) mutant that could bind to cell surface heparan sulfate proteoglycans but could not invade in the target cells. In addition, the inventors also performed immunostaining with the COS7 cells treated with the growth medium of the HEK293T cells over-expressing Vax1 or Vax1 (WF/SR). Another immunostaining was performed with the neural retina explant co-cultured with the COS7 cells over-expressing Vax1 or Vax1 (WF/SR) and the growth direction of the retinal ganglion cell axon was analyzed. As a result, it was confirmed that Vax1 (WF/SR) could bind to syndecan2, but was not found in COS7 cells, suggesting that Vax1 (WF/SR) mutant could bind to heparan sulfate proteoglycans but could not invade in the cells. It was also confirmed that the number of the retinal ganglion cell axon growing toward the COS7 cells over-expressing Vax1 (WF/SR) in the neural retina explant was reduced, indicating that the Vax1 induced the growth of the axon after invading in the retinal ganglion cells (see FIGS. 12a~12d).

To investigate the function of Vax1 in the cytoplasm, the present inventors purified the protein complex interacting with the GST-Vax1 protein over-expressed in 293T cells and performed silver staining with the same. The proteins therein were identified by MALDI-TOF. As a result, the proteins were confirmed as Vax1; ribosomal components such as ribosomal proteins (RPs) L11, L23A, L26, S14, and S16; translation regulators such as eIF (eukaryotic translation initiation factor) 3B and 3C; and HSPA1A (chaperon heat shock 70-KD protein 1A). Therefore, it was confirmed that the Vax1 was involved in the synthesis of local protein, similarly to that cytoplasm En2 is involved in the regulation of the growth of the retinal ganglion cell axon (see FIG. 13a).

To investigate whether or not Vax1 was involved in the synthesis of local protein, the present inventors performed immunostaining with the E13.5 mouse neural retina explant cultured in the medium supplemented with Vax1 or Vax1 (WF/SR) mutant protein, and measured the growth of the retinal ganglion cell axon. As a result, it was confirmed that the synthesis and the growth of the retinal ganglion cell axon were increased in the neural retina explant over-expressing Vax1. However in the neural retina explant over-expressing Vax1 (WF/SR), the synthesis and the growth of the retinal ganglion cell axon were suppressed, indicating that the Vax1 could invade in the cells to accelerate the synthesis of the local protein and stimulate the growth of the retinal ganglion cell axon there (see FIGS. 13a and 13d).

To investigate whether or not the damaged retinal ganglion cell axon in Vax1−/− mouse could be recovered by the extracellular Vax1, the present inventors transplanted the Vax1 recombinant protein and the collagen gel containing the Vax1 (WF/SR) recombinant protein in the third ventricle of Vax1lacZ/lacZ mouse, followed by immunostaining. As a result, it was confirmed that the retinal ganglion cell axon in the mouse transplanted with Vax1 (WF/SR) did not approach nor grow to the hypothalamus, unlike the mouse transplanted with Vax1 protein. When the mouse was transplanted with the collagen gel mixed with Robo 1-Fc fragment, the growth of the retinal ganglion cell axon in the ventral hypothalamus was accelerated when the mixture additionally contained Vax1-His. Therefore, it was confirmed that the Vax1 protein invaded in the axoplasm independently on the expression of axon inducing molecule and stimulated the growth of the retinal ganglion cell axon therein (see FIG. 14a).

To investigate the interaction between Vax1 and Slit2, the present inventors performed immunostaining using the neural retina explant treated with Vax1 and Slit2 proteins at the different concentrations and thereafter measured the length of the retinal ganglion cell axon. As a result, in the group treated with Vax1 together with Slit, the growth of the retinal ganglion cell axon was more suppressed than in the group treated with Vax1 alone, while the invasion of Vax1 into the retinal ganglion cell axon was not much affected by Slit 2. When the cells were cultured in the presence of both Vax1 and Robo 1-Fc, the growth of the retinal ganglion cell axon was significantly stimulated, and the competition was once again confirmed in the group treated with both Vax1 and Slit2. So, it was confirmed that Vax1 did not compete with Slit2 for the conjugation to heparan sulfate proteoglycans and instead their relationship laid in reciprocal antagonism (see FIGS. 14b~14e). Cerebral section was treated with Vax1, Vax1 (R152S), and Vax1 (WF/SR), followed by immunostaining. As a result, it was confirmed that the Vax1 protein induced not only the growth of the retinal ganglion cell axon but also the growth of the cerebral nerve axon, and the possibility of the Vax1 protein to control the cerebral midline pass of various types of neuroaxon in Vax1 knock-out mouse and human, similarly to the regulation of the retinal ganglion cell axon (see FIG. 14f).

In addition, the present inventors constructed the retinal ganglion cell axon growth regulation model controlled by Vax1 after confirming that Vax1 was expressed in radial glial cells and neural progenitor cells of the ventral hypothalamus of the mammalian brain and migrated extracellularly; the secreted Vax1 was bound to the heparan sulfate proteoglycans including syndecan so as to invade in the retinal ganglion cell axon; and then Vax1 stimulated the growth of the retinal ganglion cell axon by accelerating the synthesis of the local protein in the axoplasm (see FIG. 14g).

Therefore, the Vax1 secreted in the ventral hypothalamus and the cerebral septum binds to the extracellular sugar group of heparan sulfate proteoglycans exiting in the retinal ganglion cells and the cortical commissural nerve axon so as to invade in the axonplasm; and activates the local protein synthesis therein to stimulate the growth of the retinal ganglion cell axon, suggesting that the Vax1 of the present invention can be efficiently used as an active ingredient of a pharmaceutical composition for the acceleration of the regeneration or growth of axons.

The present invention also provides a pharmaceutical composition for regenerating nerves or accelerating growth of axons comprising a vector or cell harboring the polynucleotide encoding Vax protein as an active ingredient.

The said Vax protein is preferably selected from the group consisting of Vax1 protein comprising the amino acid sequence represented by SEQ. ID. NO: 1 and Vax2 protein harboring the amino acid sequence represented by SEQ. ID. NO: 2, but not always limited thereto.

The vector herein is preferably a linear DNA, a plasmid DNA, or a recombinant virus vector, but not always limited thereto.

The recombinant virus herein is preferably selected from the group consisting of retrovirus, adenovirus, adeno-associated virus (AAV), herpes simplex virus, and lentivirus, but not always limited thereto.

The cell herein is preferably selected from the group consisting of hematopoietic stem cells, dendritic cells, autologous tumor cells, and established tumor cells, but not always limited thereto.

The Vax protein of the present invention secreted in the ventral hypothalamus and the cerebral septum binds to the extracellular sugar group of heparan sulfate proteoglycans exiting in the retinal ganglion cells and the cortical commissural nerve axon so as to invade in the axonplasm, and activates the local protein synthesis to stimulate the growth of the retinal ganglion cell axon. Therefore the vector or cell comprising the polynucleotide encoding the Vax protein can be efficiently used as an active ingredient of a pharmaceutical composition for the acceleration of the regeneration or growth of axons.

The composition of the present invention can additionally include any generally used carriers, excipients, and diluents.

The composition of the present invention can be administered by parenterally and the parenteral administration includes external skin application, intraperitoneal injection, intralectal injection, subcutaneous injection, intravenous injection, intramuscular injection or intrathoracic injection, or solid transplantation, but not always limited thereto.

The composition of the present invention can be formulated in the forms of external use, suppositories and sterile injections, etc. The carriers, excipients and diluents are exemplified by lactose, dextrose, sucrose, sorbitol, mannitol, xylitol, erythritol, maltitol, starch, acacia rubber, alginate, gelatin, calcium phosphate, calcium silcate, cellulose, methyl cellulose, microcrystalline cellulose, polyvinyl pyrrolidone, water, methylhydroxybenzoate, propylhydroxybenzoate, talc, magnesium stearate and mineral oil. Formulations can be prepared by using generally used excipients or diluents such as fillers, extenders, binders, wetting agents, disintegrating agents and surfactant. Formulations for parenteral administration are sterilized aqueous solutions, water-insoluble excipients, suspensions, emulsions, lyophilized preparations, suppositories and injections. Water insoluble excipients and suspensions can contain, in addition to the active compound or compounds, propylene glycol, polyethylene glycol, vegetable oil like olive oil, injectable ester like ethylolate, etc. Suppositories can contain, in addition to the active compound or compounds, witepsol, macrogol, Tween 61, cacao butter, laurin butter, glycerogelatin, etc.

The effective dose of the composition of the present invention can be determined according to weight and condition of a patient, severity of a disease, preparation of a drug, administration pathway and time. The effective dose is preferably 0.0001~1 g/kg per day, and more preferably 0.001~200 mg/kg per day. The administration frequency can be once a day or a few times a day. The above dose cannot limit the scope of the invention in any way.

The present invention also provides a method for screening the candidate materials for regenerating nerves or accelerating growth of axons comprising the following steps:

1) treating the cells obtained from a test subject with the test samples and measuring the growth of axons;

2) measuring the intensity of binding between Vax1 and heparan sulfate proteoglycans in the cells of step 1); and 3) selecting those test samples that are able to increase the binding intensity between Vax1 and heparan sulfate proteoglycans of step 2), compared with that of the non-treated control.

In the method above, the intensity of binding was measured by a method selected from the group consisting of immunofluorescence method, mass spectrometry, protein chip assay, Western blotting, and ELISA, but not always limited thereto.

The Vax protein of the present invention secreted in the ventral hypothalamus and the cerebral septum binds to the extracellular sugar group of heparan sulfate proteoglycans exiting in the retinal ganglion cells and the cortical commissural nerve axon so as to invade in the axonplasm, and activates the local protein synthesis to stimulate the growth of the retinal ganglion cell axon. Therefore, the Vax protein of the present invention can be efficiently used for screening the candidate materials for the acceleration of the regeneration and growth of axons.

The present invention also provides a method for regenerating nerves containing the step of administering a pharmaceutically effective dose of Vax protein to a subject having neuronal and axonal damage.

The present invention also provides a method for accelerating the growth of axons containing the step of administering a pharmaceutically effective dose of Vax protein to a subject having neuronal and axonal damage.

The present invention also provides a method for regenerating nerves containing the step of administering a pharmaceutically effective dose of a vector or cell comprising the polynucleotide encoding Vax protein to a subject having neuronal and axonal damage.

The present invention also provides a method for accelerating the growth of axons containing the step of administering a pharmaceutically effective dose of a vector or cell comprising the polynucleotide encoding Vax protein to a subject having neuronal and axonal damage.

The Vax protein of the present invention secreted in the ventral hypothalamus and the cerebral septum binds to the extracellular sugar group of heparan sulfate proteoglycans exiting in the retinal ganglion cells and the cortical commissural nerve axon so as to invade in the axonplasm, and activates the local protein synthesis to stimulate the growth of the retinal ganglion cell axon. Therefore, the Vax protein above or the vector or cell comprising the polynucleotide encoding the said Vax protein can be efficiently used for the method for regenerating nerves or accelerating growth of axons by administering thereof.

The present invention also provides an use of Vax protein for a pharmaceutical composition for regenerating nerves or accelerating growth of axons.

In addition, the present invention provides an use of a vector or cell harboring the polynucleotide encoding Vax protein for a pharmaceutical composition for regenerating nerves or accelerating growth of axons.

The Vax protein of the present invention secreted in the ventral hypothalamus and the cerebral septum binds to the extracellular sugar group of heparan sulfate proteoglycans exiting in the retinal ganglion cells and the cortical commissural nerve axon so as to invade in the axonplasm, and activates the local protein synthesis to stimulate the growth of the retinal ganglion cell axon. Therefore, the Vax protein above or the vector or cell comprising the polynucleotide encoding the Vax protein can be efficiently used for a pharmaceutical composition for regenerating nerves or accelerating growth of axons.

Practical and presently preferred embodiments of the present invention are illustrative as shown in the following Examples.

However, it will be appreciated that those skilled in the art, on consideration of this disclosure, may make modifications and improvements within the spirit and scope of the present invention.

EXAMPLE 1

Construction of Vax1 Over-expressing, Vax1 Knock-out, and Vax1 Knock-in Animal Models <1-1> Separation and Culture of the Neural Retina (NR) and Ventral Hypothalamic (vHT) Explants from Vax1 Knock-out Mouse Vax1lacZ/+, Vax1−/− knock-out, and Vax1lacZ/lacZ knock-in mice were constructed according to the method presented in the following references (Bertuzzi et al., 1999; Hallonet et al., 1999). The neuronal retina (NR) and ventral hypothalamic (vHT) explants were obtained from the constructed mice above according to the method presented in the following reference (Sato et al., 1994). The obtained neural retina or the ventral hypothalamic explant was added to the collagen mixture (Invitrogen). The collagen mixture containing the neural retina or the ventral hypothalamic explant was loaded in the plate coated with 10 μg/ml of poly-L-lysine and 10 μg/ml of laminin, followed by culture at 37° C. for 1 hour, leading to gelling. Then, the culture was continued in the neurobasal medium comprising B27 adjuvant (Invitrogen).

<1-2> Construction of Vax1 Over-expressing Drosophila

Ptc-Gal4, UAS-DsRed, UAS-Sdc, UAS-Dlp, and sdc23 drosophilas were obtained from Bloomington stock center. The mouse Vax1 (SEQ. ID. NO: 1) was cloned in the vector pUAS-EGFP, resulting in the preparation of the vector pUAS-Vax1-EGFP. The vector was injected in the *drosophila*, resulting in the construction of UAS-Vax1-EGFP *drosophila*. The third instar larvae of Ptc-Gal4>UAS-Vax1-EGFP,UAS-DsRed;+ was obtained by the cross breeding of Ptc-Gal4>UAS-DsRed;TM6B *drosophila* and UAS-Vax1-EGFP *drosophila*. The third instar larvae of Ptc-Gal4>UAS-Vax1-EGFP,UAS-DsRed;Sdc23 was obtained by the cross breeding of Ptc-Gal4>UAS-DsRed;Sdc23 *drosophila* and UAS-Vax1-EGFP *drosophila*. The third instar larvae of Ptc-Gal4>UAS-Vax1-EGFP,UAS-DsRed;Sdc was obtained by the cross breeding of Ptc-Gal4>UAS-DsRed;Sdc *drosophila* and UAS-Vax1-EGFP *drosophila*. The third instar larvae of Ptc-Gal4>UAS-Vax1-EGFP,UAS-DsRed;Dlp was obtained by the cross breeding of Ptc-Gal14>UAS-DsRed;Dlp *drosophila* and UAS-Vax1-EGFP *drosophila*.

EXAMPLE 2

Regulation of Non-cell Autonomous Retinal Ganglion Cell (RGC) Axon Growth by Vax1

<2-1> Confirmation of the Normal Development of Optic Chiasm (OC) Forming Cells in Vax1−/− Mouse Vax1 is expressed in the cells located in the optic pathway structure such as optic stalk (OC) and optic chiasm (OC), and is known to play an important role in the fasciculation of retinal ganglion cell axon and the formation of optic chiasm (Bertuzzi et al., 1999; Hallonet et al., 1999). To investigate the effect of Vax1 on the optic pathway structure, immunostaining was performed with the optic chiasm forming cells of Vax1−/− mouse.

Particularly, the brain obtained from the E14.5 Vax1+/+ and Vax1−/− mouse embryo according to the same manner as described in Example <1-1>, was cut into sections (coronal: 12 μm). The obtained brain sections were washed with 1×PBS, and then fixed in 4% (v/v) paraformaldehyde (PFA)/PBS at 4° C. for 2~16 hours. The brain sections were then cultured in 20% (w/v) sucrose/PBS at 4° C. for 16 hours. The sections invaded in OCT medium, which were then frozen. The frozen brain sections were cultured in the blocking solution supplemented with 0.2% TritonX-100, 5% normal donkey serum, and 2% bovine serum albumen (BSA), followed by reaction with rabbit anti-Vax1 antibody (Mui et al., 2005, green), goat anti-Sox2 antibody (Santa Cruz Biotechnology, red) for the visualization of the neural progenitor cell (NPC) marker Sox2, and mouse anti-Tuj1 antibody (Covance, blue) for the visualization of the post mitotic neuronal marker tubulin-betaIII. The sections were washed with PBS three times. Then, the sections were reacted with Alexa488, Cy3 or Cy5-conjugated secondary antibody (Jackson ImmunoResearch Laboratories, West Glove, Pa., USA) diluted at room temperature for 2 hours at the ratio of 1:1000, followed by washing with PBS. Visualization was performed by using Zeiss LSM710 conforcal microscope (FIG. 1a). As explained hereinbefore, the brain sections were fixed, followed by invading and blocking. Then, the sections were immunostained with anti-Vax1 antibody (green), anti-nestin (RC2) antibody (red, Millipore), followed by visualization (FIG. 1b).

As a result, as shown in FIG. 1a and FIG. 1b, Vax1 was found in Sox2 (SRY box 2)-positive neural progenitor cells providing a signal involved in the inducement of retinal ganglion cell axon and nestin-positive radial glial cells wherein RC2 was detected, but was not found in Tuj1-positive neurons (FIG. 1a and FIG. 1b, line 1). And, it was confirmed that the optic chiasm forming cells were normally developed in Vax1−/− mouse (FIG. 1a and FIG. 1b, line 2). Therefore, it was also confirmed that the Vax1 was expressed in the optic chiasm existing in Sox2-positive neural progenitor cells and nestin-positive radial glial cells. The abnormal development of the optic chiasm in the Vax1 knock out mouse was not attributed to the mal-formation of optic chiasm forming ventral hypothalamic cells (FIGS. 1a and 1b).

<2-2> Regulation of Non-cell Autonomous Retinal Ganglion Cell Axon Growth by Vax1

To investigate the effect of Vax1 on the development of optic chiasm, the present inventors co-cultured the ventral hypothalamic and neural retina explants separated from Vax1−/− mouse and then observed the growing direction of the retinal ganglion cell axon.

Particularly, the ventral hypothalamic (vHT) and neural retina (NR) explants separated from the E13.5 Vax1 normal mouse (Vax+/+, WT) and the Vax1 knock out mouse (Vax−/−, KO) obtained by the same manner as described in Example <1-1> were co-cultured with the combinations of Vax1+/+ vHT/Vax1+/+ NR, Vax1+/+ vHT/Vax1−/− NR, and Vax1−/− vHT/Vax1+/+ NR for 48 hours, followed by fixing at 4° C. for 2~16 hours with 4% PFA/PBS. Immunostaining was performed by using the mouse anti-NF160 antibody (DSHB, red) for the visualization of the retinal ganglion cell axon marker NF160 and by using DAP1 (4′,6-diamidino-2-phenylindole, blue) for the visualization of the nucleus of the explant by the same manner as described in Example <2-1> (FIG. 2b). Then, the growing direction of the retinal ganglion cell axon was measured. As shown in the schematic diagram of FIG. 2, all the meaningful retinal axon growing sites in the range of 20 μm~40 μm in the outer layer of the neural retina explant were marked as a yellow ring. The clockwise direction angle formed by the parallel lines at the end of the retinal axon/bundle and the line connecting the centers of the neural retina (NR) and the ventral hypothalamic (vHT) explants was measured. If the angle was between 0°~60° and between 301°~360°, it was judged as the positive (+; red) direction. If the angle was between 61°~120° and between 241°~300°, it was judged as the neutral direction (0; green). If the angle was between 121°~240°, it was judged as the negative direction (−; blue). So, the direction of the tip of the retinal ganglion cell axon (FIG. 2c) and the direction of the shaft of the retinal ganglion cell axon (FIG. 2d) in the yellow ring region were presented in the graph (FIG. 2c and FIG. 2d).

As a result, as shown in FIGS. 2b~2d, the number of the retinal ganglion cell axon growing toward the ventral hypothalamic explant of the Vax+/+ mouse was increased in the Vax1+/+ and Vax1−/− mouse retina, while the number of the retinal ganglion cell axon growing toward the ventral hypothalamic explant of the Vax1−/− mouse was reduced. The result indicates that the Vax1 originated from the ventral hypothalamic explant induces the growth of the retinal ganglion cell axon in the retina (FIGS. 2b~2d).

<2-3> Regulation of Non-cell Autonomous Retinal Ganglion Cell Axon Growth by Vax1 Confirmed by In Situ Hybridization (ISH) and Immunofluorescence Staining (IF)

To investigate the effect of Vax1 on the development of optic chiasm, the present inventors first examined the malfunction in the inducement of the retinal ganglion cell axon of the ventral hypothalamus separated from the Vax1−/− mouse. To do so, the presence of the retinal ganglion cell axon growth factor, vescular endothelial growth factor (VEGF164), and neuronal cell adhesion molecule (NrCAM) were first investigated.

Particularly, the embryo heads separated from the E14.5 Vax1 normal mouse (Vax+/+, WT) and the Vax1 knock out mouse (Vax −/−, KO) obtained by the same manner as described in Example <1-1> were fixed in 4% PFA/PBS at 4° C. for 2~16 hours, which were prepared as frozen sections. The expression of the Vegfa mRNA in the section was confirmed by in situ hybridization. The expression of NrCAM protein was confirmed by immunofluorescent staining (scale bar: 100 μm).

As a result, as shown in FIG. 2e, it was confirmed that the optic chiasm forming cell marker NrCAM and the optic chiasm signal Vegfa were expressed in the Vax1−/− mouse. It was also confirmed that the expression region was widened (FIG. 2e).

Therefore, it was confirmed in Example 2 that the Vax1 regulated the growth of the retinal ganglion cell axon via non-cell autonomous method.

EXAMPLE 3

Transcriptional Activity Non-dependent Extracellular Vax1 Secretion

<3-1> Transcriptional Activity Non-dependent Stimulation of the Retinal Ganglion Cell Axon Growth by Vax1

Transcription inactive Vax1 (R152S) mutant has been identified in the patients with coloboma, cleft palate, and agenesis of corpus callosum (ACC). It displays a similar phenotype to that of the Vax1 knock out mutant mouse (Slavotinek et al., 2012). To investigate the effect of Vax1 transcriptional activity on the growth of the retinal ganglion cell axon, immunostaining was performed with the COS7 cells over-expressing Vax1, transcription inactive Vax1 mutant (Vax1 (R152S)), and Vax2 sharing the homeodomain with Vax1, and then the growing direction of the retinal ganglion cell axon was measured by Western blotting.

Particularly, the constructs encoding Myc-tagged mouse Vax1, Myc-tagged mouse transcription inactive Vax1 mutant wherein the $152^{nd}$ arginine had been substituted with serine (Vax1 (R152S)), and Myc-tagged mouse Vax2 were constructed. COS7 cells (ATCC) were transfected with the said constructs by using calcium phosphate. The transfected cells were co-cultured with the neural retina explant obtained by the same manner as described in Example <1-1> for 48 hours. Immunostaining was performed using anti-Myc antibody (Santa Cruz Biotechnology, green), anti-NF160 antibody (red), and DAPI (blue) for the visualization by the same manner as described in Example <2-1>. The centers of the two explants above were connected by a red dotted line (scale bar: 500 μm (first row), scale bar:100 μm (second and third rows)) (FIG. 3a).

The angle formed by the red dotted line connecting the centers of the retinal ganglion cell explant and COS7 cells was measured by the same manner as described in Example <2-2> in order to make a graph presenting the growing direction of the retinal ganglion cell axon. The value of the graph was presented as mean value and the error bar was presented by SD (control (n=21), Vax1 (n=17), Vax1 (R152s) (n=8), Vax2 (n=7)). P value was calculated by ANOVA (0.001<p<0.005) (FIG. 3b).

In addition, Western blot analysis was performed to investigate the presence of Vax protein in the growth medium of the COS7 cells over-expressing Vax1, Vax1 (R152S) or Vax2. First, the growth medium and the grown COS7 cells transfected with Myc-Vax1, Myc-Vax1 (R152S), or Myc-Vax2 were obtained. The obtained cells were lysed in the lysis buffer containing 10 mM Tris-HCA (pH 7.4), 200 nM NaCl, and 1% NP-40. The obtained growth medium was centrifuged at 500×g for 10 minutes twice, followed by the additional centrifugation at 2,000×g for 15 minutes twice to obtain supernatant (S3) fraction. The obtained supernatant fraction was added with 3 M trichloroacetic acid (TCA) solution at the equal amount to the volume of the supernatant fraction, leading to the precipitation of macro molecules. The TCA precipitate was washed with 100% acetone twice, which was then dried to give pellet. The obtained cell lysate and pellet were added with 2×SDS sample buffer to terminate the reaction. SDS-PAGE was performed and the reactant was transferred onto PVDF membrane (polyvinylidene fluoride membrane, Millipore, USA). As a primary antibody, anti-Myc antibody was treated thereto, followed by reaction. HRP-conjugated secondary antibody was conjugated to the primary antibody attached on the membrane, confirmed by ECL (Pierce chemical Co, USA) (FIG. 3c).

As a result, as shown in FIG. 3a and FIG. 3b, the number of the neurofilament 160 kDa (NF 160)-positive retinal ganglion cell axon growing toward the COS7 cells over-expressing Vax1 co-cultured with the neural retina explant was significantly increased, compared with the control. In the meantime, the number of the retinal ganglion cell axon growing toward the COS7 cells over-expressing Vax2 or wild type COS7 cells co-cultured with the same was not changed. When the COS7 cells expressing the transcription inactive Vax1 (R152S) mutant was co-cultured, the number of the retinal ganglion cell axon growing therein was as much increased as shown when the COS7 cells over-expressing wild type (WT) Vax1 was co-cultured. Vax1 and Vax1 (R152S) were also identified in the NF160-positive retinal ganglion cell axon separated from the retina explant co-cultured with the cells, suggesting that the activation of growth stimulation of the retinal ganglion cell axon was specific to Vax1, that is the Vax1 induced the retinal ganglion cell axon growth transcription independently (FIGS. 3a and 3b).

As shown in FIG. 3c, Vax1 and Vax1 (R152S) were also detected in the growth medium (GM) of the transformed COS7 cells, while Vax2 protein was not found there. Therefore, it was confirmed that the Vax1 was secreted extracellularly, regardless of the transcriptional activity, to induce the growth of the retinal ganglion cell axon (FIG. 3c).

<3-2> Vax1 Secretion in the Cells Cultured In Vivo and In Vitro

To confirm the secretion of Vax1 in the course of the retinal ganglion cell axon growth induction, immunostaining and Western blotting were performed with the cells cultured in vitro and in vivo.

Particularly, the constructs encoding EGFP, EGFP-tagged Vax1, and EGFP-tagged Vax2 were constructed. HEK293T cells (ATCC) were transfected with those constructs by the same manner as described in Example <3-1>. The growth medium was obtained 48 hours later, followed by centrifugation. After eliminating the cells, the supernatant (S3) containing the secreted protein and extracellular membrane vesicles was obtained. The obtained supernatant was added to the non-transfected COS7 cells, followed by culture for 12 hours. Immunostaining was performed with the HEK293T cells and COS7 cells using mouse anti-GFP antibody (Santa Cruz Biotechnology, green) and DAPI (blue) by the same manner as described in Example <2-1> for the visualization (scale bar: 20 μm) (FIG. 4a).

HEK293T cells were transfected with the Myc or Myc-Vax1 construct by the same manner as described in Example <3-1>. The supernatant (S3) of the growth medium was obtained 48 hours later. The obtained growth medium supernatant was concentrated by using Centricon filters (cut-off limit 20 kDa; Millipore) according to the manufacturer's protocol. 2 μl of the concentrated supernatant containing 50 μl of the protein was injected in the lateral ventricle of E13.5 mouse in utero. 12 hours later, the brain of the mouse was extracted by the same manner as described in Example <2-1> and the brain sections (horizontal: 20 μm) were obtained, followed by immunostaining using mouse anti-Myc antibody and DAPI for the visualization (FIG. 4b).

The ventral hypothalamic explant separated from E13.5 mouse by the same manner as described in Example <1-1> was cultured for 24 hours. Pellet and cell lysate were obtained from the growth medium (GM) by the same manner as described in Example <3-1>. Western blotting was performed with the obtained pellet and cell lysate using anti-Vax1 antibody and anti-tubulin-betaIII antibody (FIG. 4c). Cerebrospinal fluid (CSF) was obtained from the lateral ventricle of E14.5 mouse. The supernatant (S3) was separated from the dead cell debris (P2) by the same manner as described in Example <3-1>. Western blotting was performed with the obtained supernatant (S3), the dead cell debris (P2), and the ventral hypothalamic explant cell lysate (CL) using anti-Vax1 and anti-tubulin-beta III antibody by the same manner as described in Example <3-1> (FIG. 4d).

As a result, as shown in FIG. 4a and FIG. 4b, the HEK293T cells transfected with EGFP, EGFP-Vax1, and EGFP-Vax2 demonstrated similar cell survival rates among themselves. The Vax1 protein identified in the HEK293T cells transfected with Vax1 was also found in the COS7 cells cultured in vitro (FIG. 4a, line 2) and also in the ventral diencephalic (vDC) explant cultured in vivo (FIG. 4b, line 2). Therefore, it was confirmed that the Vax1 protein was secreted from the HEK293T cells transfected with Vax1 and then migrated into the retinal ganglion cell axon co-cultured with the same (FIG. 4a and FIG. 4b).

As shown in FIG. 4c and FIG. 4d, the intracellular expression level of Vax1 in the ventral hypothalamic explant was similar to the over-expressed Vax1 level in COS7 cells (FIG. 3c) and the Vax1 expression was also confirmed in the ventral hypothalamic explant growth medium (FIG. 4c, GM) and in CSF (FIG. 3d, CSF; S3). Therefore, it was confirmed that the Vax1 was the protein secreted not only in vivo but also in vitro.

<3-3> Vax1 Secretion in the Cells Cultured In Vitro

To investigate the Vax1 secretion in the course of the retinal ganglion cell axon growth induction, immunostaining was performed with the cells cultured in vitro.

Particularly, COS7 cells were transfected with Myc-tagged mouse Vax1 by using calcium phosphate. The transfected cells were co-cultured with the retinal ganglion cell explant obtained by the same manner as described in Example <1-1> for 24 hours. Co-culture was continued in the medium supplemented with rb-IgG (1 μg/ml) or anti-Vax1 antibody (1 μg/ml) further for 24 hours. Immunostaining was performed using anti-Myc antibody (green), anti-NF160 antibody (red), and DAPI (blue) by the same manner as described in Example <2-1> for the visualization. The boxed area in the left presents in the right and the arrow indicates the location of the Myc-tagged mouse Vax1 in the retinal ganglion cell axon (scale bar: 500 μm (left), scale bar: 100 μm (right)).

As a result, as shown in FIG. 4e, the axon Vax1 immunostaining signal was significantly reduced in the presence of the anti-Vax1 antibody (α-Vax1) (FIG. 4e).

Therefore, it was confirmed from the above result of Example 3 that the Vax1 was the protein secreted in the ventral hypothalamus regardless of the transcriptional activity.

EXAMPLE 4

Stimulation of the Retinal Ganglion Cell Axon Growth by the Secreted Vax1 Protein <4-1> Induction of the Retinal Ganglion Cell Axon Growth by the Vax1 Secreted in the Ventral Hypothalamic Explant To investigate whether or not the secreted Vax1 could induce the growth of the retinal ganglion cell axon toward the ventral hypothalamic explant, the extracellular Vax protein was separated by using rabbit anti-Vax1 polyclonal antibody and anti-Vax2 polyclonal antibody, followed by immunostaining. The growing direction of RGC axon and the length of RGC axon were measured.

Particularly, 1 μg/ml of pre-immune rabbit IgG (rbIgG), 1 μg/ml of anti-Vax1 polyclonal antibody (α-Vax1), or 1 μg/ml of anti-Vax2 polyclonal antibody (α-Vax2) was treated to the ventral hypothalamic explant and the neural retina explant obtained and co-cultured by the same manner as described in Example <1-1>, followed by culture for 48 hours. Immunostaining was performed using rabbit anti-Vax1 antibody (green) and anti-NF160 antibody (red) by the same manner as described in Example <2-2> for the visualization. The centers of the two explants above were connected by a red dotted line and the arrow designated part was presented as enlarged (scale bar: 500 μm) (FIG. 5a).

The angle formed by the red dotted line was measured by the same manner as described in Example <2-2>, based on which the growing direction of the retinal ganglion cell axon was made as a graph. The value of the graph was presented as mean value and the error bar was presented by SD (rbIgG (n=17), α-Vax1 (n=19), α-Vax2 (n=11)). p-value was calculated by ANOVA ($0.001 < p < 0.005$) (FIG. 5b).

NF160 immunofluorescence image pixel was calculated to make a graph of the relative number and the thickness of the axon/bundle growing out from the retina. NF160 immunofluorescence image was changed into binary image, from which the pixel number was counted by using the Histogram function of image-J software. The relative number of the axon/bundle was calculated by subtracting the number of pixels in the inner side of the neural retina explant from the number of total pixels of the explant comprising the axon/bundle. The thickness was calculated by measuring the number of pixels in 30~40 μm range of each axon/bundle. The value of the graph was presented as mean value and the rbIgG treated group was considered as 100%. The error bar was presented by SD (FIG. 5c).

The retina explant obtained by the same manner as described in Example <1-1> was cultured for 24 hours, to which 6X-His FITC fluorescein isothiocyanate (FITC) labeled peptide (100 ng/ml) or His-tagged Vax1 recombinant protein labeled with FITC (500 ng/ml) was added, followed by further culture for 24 hours. During the culture, the neuroaxon growing in the retina explant and the FITC fluorescence signal presented in the neuroaxon were detected and visualized every 15 minutes. The red arrow indicates the enlarged image (FIG. 5d). The retina explant was washed with PBS, followed by immunostaining using rabbit α-Vax1 (green) and anti-His antibody (red) by the same manner as described in Example <2-1> for the visualization. The box in the right of the image indicates the enlarged image of the left, and the arrow indicates Vax1 and His protein located in the retinal ganglion cell axon (FIG. 5e) (scale bar: 100 μm).

The quadrant of the retina explant obtained by the same manner as described in Example <1-1> was treated with 6X-His peptide (25 ng/ml, white rod) or Vax1-His protein (100 ng/ml, black rod). 24 hours later, the changes in the length of the axon were measured and presented as a graph. The value of the graph was presented as mean value and the error bar was presented by SD. The number written on the rod indicates the number of the analyzed axon and the number of the analyzed explant presented on top. p-value was calculated by t-test (**, p<0.001). The results were obtained by repeating the independent experiment twice (FIG. 5f).

The retina explant obtained by the same manner as described in Example <1-1> was added or not added with His-tagged Vax2 (100 ng/ml), followed by culture for 24 hours. Immunostaining was performed using rabbit anti-Vax2 antibody (green), mouse anti-NF160 antibody (red), and DAPI (blue) by the same manner as described in Example <2-1> for the visualization. The box on top indicates the enlargement of the image of the bottom and the arrow indicates the His-tagged Vax2 located in the retinal ganglion cell axon (scale bar: 500 μm (upper part), scale bar: 100 μm (lower part)) (FIG. 5g-A). The length of the axon was measured and presented as a graph. The value of the graph was presented as mean value and the error bar was presented by SD. The number written on the rod indicates the number of the analyzed axon, and the number of the analyzed explant is as follows. 6X-His n=5), Vax2 (n=4). P-value was calculated by t-test (**, p<0.001) (FIG. 5g-B).

As a result, as shown in FIG. 5a and FIG. 5b, when the cells were treated with anti-Vax1 polyclonal antibody, unlike when the cells were treated with rabbit IgG and anti-Vax2 polyclonal antibody, Vax1 was not detected in the retinal ganglion cell axon (FIG. 5a) and the growth of the retinal ganglion cell axon toward the ventral hypothalamic explant was reduced (FIG. 5b). Therefore, it was confirmed that the activity of Vax1 to stimulate the migration and the growth of the retinal ganglion cell axon was suppressed by the anti-Vax1 polyclonal antibody.

As shown in FIG. 5c, when the cells were treated with rabbit IgG and anti-Vax2 polyclonal antibody, the number of the retinal ganglion cell axon/bundle and the thickness thereof were not changed. In the meantime, when the cells were treated with anti-Vax1 polyclonal antibody, the number and the thickness of the retinal ganglion cell axon/bundle were reduced. Therefore, it was confirmed that the extracellular Vax1 played an important role in the fasciculation of the axon (FIG. 5c).

As shown in FIGS. 5d-5f, when the FITC labeled recombinant protein was added to the His-tagged Vax1, the growth of the retinal ganglion cell axon was strongly stimulated (FIGS. 5d-5e). This phenomenon was equally observed in the quadrant of the retina explant (FIG. 5f).

As shown in FIG. 5g, it was confirmed that Vax2 could induce the growth of the retinal ganglion cell axon as much as Vax1 could do (FIG. 5g).

<4-2> Stimulation of the Retinal Ganglion Cell Axon Growth by Extracellular Vax1 In Vivo To investigate the role of the extracellular Vax1 in the growth of the retinal ganglion cell axon in vivo, immunostaining was performed with the mouse transplanted with collagen gel and the number, the thickness, and the length of the retinal ganglion cell axon were measured.

Particularly, as shown in the schematic diagram of FIG. 6a (upper part), the lipophilic fluorescent dye DiI (25 μM) was injected in the left eyeball of E13.5 mouse in order to label the retinal ganglion cell axon. Half of the dorsal brain and the lower part of the mouth were cut. It was placed with the dorsal part down in the culture slide camber. The mouse brain slab including eyeball, forebrain, and midbrain structures were obtained. Then, the collagen solution containing 1 μg/ml of non-immune rabbit IgG (rbIgG) or 1 μg/ml of rabbit anti-Vax1 polyclonal antibody (α-Vax1) was transplanted in the third ventricle of the slab above, to which the culture medium was added, followed by culture in a 37° C. 7% $CO_2$ incubator for 12 hours. The brain slab was cut by the same manner as described in Example <2-1>, resulting in the obtainment of the brain section (horizontal: 12 μm). The brain section was fixed in 4% PFA/PBS, and then frozen with OCT medium. The frozen brain section was observed under Olympus FV1000 conforcal microscope to visualize the DiI epifluorescence for the confirmation of the DiI-labeled axon growth (FIG. 6, bottom, line 1). Immunostaining was performed with the frozen brain section containing optic chiasm using anti-Vax1 antibody (green) and anti-NF160 antibody (red) by the same manner as described in Example <2-1> for the visualization (scale bar: 200 μm) (FIG. 6, bottom, line 2).

The retina explant obtained by the same manner as described in Example <1-1> was cultured for 24 hours, followed by the treatment with or without 1 μg/ml of rabbit anti-Vax1 polyclonal antibody. The retina explant was treated with 0.1 μg/ml of Vax1-His recombinant protein, followed by further culture for 24 hours. 24 hours later, immunostaining was performed with anti-Vax1 antibody (green), anti-NF160 antibody (red), and DAPI (blue) by the same manner as described in Example <2-1> for the visualization. The arrow indicates the enlargement area (scale bar: 500 μm) (FIG. 6b). 24 hours before the immunostaining, the changes in the length of the retinal ganglion cell axon were video-recorded real-time, and the results are presented in a graph (FIG. 6c). After the immunostaining, the changes in the number, the thickness, and the length of the retinal ganglion cell axon/bundle were also observed and presented in a graph by the same manner as described in Example <4-1> (FIG. 6d). The value of the graph was presented as mean value and the error bar was presented by SD (non treated (n=11), Vax1 (n=10), Vax1+α-Vax1 (n=12)).

As a result, as shown in FIG. 6a, it was confirmed that the retinal ganglion cell axon growing toward the optic chiasm was reduced in the mouse transplanted with anti-Vax1 polyclonal antibody, compared with the mouse treated with pre-immune IgG (FIG. 6a, line 1, the darker area indicates the DiI-labeled retinal ganglion cell axon). It was also confirmed that that lots of the retinal ganglion cell axon displayed the reduced Vax1 immunoreactivity and the growth thereof was arrested in the outer wall of the ventral diencephalon similarly to the phenomenon shown in the Vax1 knock out mouse (FIG. 6a, line 2).

As shown in FIGS. 6b~6d, when the recombinant Vax1 protein was added to the growth medium, the number, the thickness, and the length of the retinal ganglion cell axon were all increased. In the meantime, when the recombinant Vax1 protein and the anti-Vax1 polyclonal antibody were added together to the medium, the number and the thickness of the retinal ganglion cell axon were not much different from those of the control and the length was even suppressed not to grow. Therefore, it was confirmed that the anti-Vax1 antibody was in the relationship of antagonism with the recombinant Vax1 protein co-cultured with the above in the aspects of the location and the growth of axon, and the recombinant Vax1 protein could stimulate the growth of the retinal ganglion cell axon significantly (FIGS. 6b~6d). From the results of Example 4, it was confirmed that the extracellularly secreted Vax1 directly stimulated the growth of retinal ganglion cell axon.

EXAMPLE 5

Intercellular Migration of In Vivo Vax1 Protein

According to the previous reports, Vax1 mRNA is expressed in the retinal ganglion cell axon associated structure including optic disc (OD), optic stalk (OS), preoptic area (POA), and ventral hypothalamus (vHT) of E14.5 mouse (Bertuzzi et al., 1999; Hallonet et al., 1999). To investigate whether or not Vax1 mRNA or Vax1 protein was expressed in the retina, in situ RNA hybridization, immunostaining, and qRT-PCR were performed.

Particularly, in situ RNA hybridization was performed with the retina prepared from the Vax1+/+ (WT) and Vax1lacZ/lacZ E14.5 mice obtained by the same manner as described in Example <1-1> using [33P]-CTP-labeled antisense Vax1 probe according to the method described in the following reference (Mui et al., 2005) for the visualization of the Vax1 mRNA expression (scale bar: 200 μm) (FIG. 7a).

The brain section was obtained by the same manner as described in Example <2-1> from the E14.5 Vax1lacZ/+ and vax1lacZ/lacZ mice obtained by the same manner as described in Example <1-1>, followed by immunostaining using rabbit anti-Vax1 antibody (green), mouse anti-β-galactosidase antibody (red), and DAPI (blue) for the visualization. i and iii indicate the visualized neural retina (NR) and ii and iv indicate the visualized optic disc (OS) (scale bar: 200 μm (lines 1 and 2), scale bar: 20 μm (lines 3 and 4)) (FIG. 7b).

The brain sections were prepared by the same manner as described in Example <2-1> from the Vax1+/+ and Vax1lacZ/lacZ E14.5 mice obtained by the same manner as described in Example <1-1>, followed by immunostaining using rabbit anti-Vax1 antibody (green), moue anti-NF160 antibody (red), and DAPI (blue) for the visualization. i and iii indicate the visualized neural retina (NR) and ii and iv indicate the visualized optic disc (OS) (scale bar: 200 μm (line 1), scale bar: 20 μm (lines 2 and 3)) (FIG. 7c).

The brain sections were obtained by the same manner as described in Example <2-1> from the Vax1+/+ (WT) or Vax1lacZ/lacZ E18.5 prepared by the same manner as described in Example <1-1>, followed by immunostaining with the retina (upper part) and the optic nerve (lower part) by using rabbit anti-Vax1 antibody and gold (250 nm)-labeled anti-rabbit IgG for the visualization with electron microscope (EM) (scale bar: 0.5 μm (line 1), scale bar: 0.2 μm (lines 2 and 3)) (FIG. 7d).

In situ RNA hybridization was performed with the brain sections obtained from the Vax1+/+(WT) and Vax1−/− E14.5 mice prepared by the same manner as described in Example <1-1> by using [33P]-CTP-labeled antisense Vax1 probe according to the method described in the following reference (Mui et al., 2005) for the visualization of the Vax1 mRNA expression. Immunostaining was also performed using anti-Vax1 antibody for the visualization (scale bar: 5 μm) (FIG. 7e-A). The brain sections were obtained by the same manner as described in Example <2-1> from the E14.5 Vax1+/lacZ and Vax1lacZ/lacZ mice prepared by the same manner as described in Example <1-1>, followed by immunostaining using rabbit anti-Vax1 antibody (green) and mouse anti-β-galactosidase antibody (DSHB) (red) for the visualization. The box in the left of the image indicates the enlarged image of the right (scale bar: 50 μm) (FIG. 7e-B).

As a result, as shown in FIG. 7a, the Vax1 mRNA expression was confirmed in the optic disc (OD), optic stalk (OS), preoptic area (POA), and ventral hypothalamus of the E14.5 Vax1+/+ mouse, but not in the retina, suggesting that the VAx1 was expressed in the retinal ganglion cell axon associated structures including optic disc, optic stalk, and preoptic area except the retina (FIG. 7a).

As shown in FIG. 7b, Vax1 protein was expressed in the Vax1lacZ/+ mouse retinal cells and Vax1 and β-galactosidase were co-expressed in the Vax1lacZ/+ mouse optic stalk astrocyte precursor cells (APCs). However, Vax1 protein was mainly found in the nuclei (FIG. 7b, line 1). The expression of Vax1 was not completed in the retinal ganglion cells and optic stalk astrocyte precursor cells (OS APCs) of the Vax1lacZ/lacZ heterozygote knock-in mouse (FIG. 7b, lower line). Therefore, it was confirmed that the Vax1 was specific to the Vax1lacZ/+ mouse retinal ganglion cells (FIG. 7b).

As shown in FIG. 7c, Vax1 and NF160 were co-expressed in the nuclei of the Vax1+/+ mouse optic stalk astrocyte precursor cells (FIG. 7c, line 1). However, in the Vax1lacZ/lacZ mouse optic stalk and neural retina, NF160 protein was expressed but Vax1 protein was not expressed (FIG. 7c, line 2). Therefore, it was confirmed that the Vax1 existed in the retinal ganglion cell axon of the Vax+/+ mouse optic nerve but was not expressed in the retinal ganglion cell axon of the defibered Vax1lacZ/lacZ mouse (FIG. 7c).

As shown in FIG. 7d, Vax1 protein was bound to the outer surface of the retinal ganglion cell plasma membrane and was expressed in the endocytic vesicles of the retinal ganglion cells as well (FIG. 7d, line 1). In the meantime, Vax1 existed with trafficking vesicles and nuclear chromatin (FIG. 7d, line 2) in the optic stalk astrocyte precursor cells (OS APCs) (FIG. 7d).

As shown in FIG. 7e, Vax1 mRNA was expressed in the hypothalamic cell cord, optic nerve, and optic chiasm but not in the brain of the Vax1lacZ/lacZ mouse (FIG. 7e).

From the above results, it was confirmed that the Vax1 was expressed in the retinal ganglion cell axon associated structures except the retina and the secreted Vax1 protein in the optic stalk or ventral hypothalamus safely arrived on the retinal ganglion cell axon membrane to go further in the retinal ganglion cells.

EXAMPLE 6

Intercellular Migration of Vax1 Regulated by Heparan Sulfate Proteoglycans (HSPG)

It has been reported that the homeodomain transcription factors such as En2 (engrailed-2) and Otx2 (orthodenticle homeodomain 2) are involved in intercellular migration (Brunet et al., 2007; Brunet et al., 2005; Sugiyama et al., 2008). But the mechanism of regulating the transport of those homeodomain transcription factors has not been explained, yet. Syndecan (Sdc), the gene encoding protein and the transmembrane heparan sulfate proteoglycan (HSPG) protein that might change the cell migration of Vax1, was identified in *drosophila* (Spring et al., 1994). To investigate whether or not the syndecan was involved in Vax1, the homeodomain transcription factor, mediated regulation of intercellular migration, immunostaining was performed with the *drosophila* expressing Ptc-Gal4 induced Vax1-EGFP and Ds-Red, the *drosophila* expressing Ptc-Gal4 induced Vax1-EGFP, Ds-Red and Sdc or Sdc mutant (sdc23), and the *drosophila* expressing Ptc-Gal4-induced Vax1-EGFP, Ds-Red, and Dlp (dally like protein) which is the homologous protein of heparan sulfate proteoglycans glypican (Glp).

Particularly, the imaginal discs obtained from the Ptc-gal4>Vax1-EGFP,Ds-Red *drosophila*, Ptc-gal4>Vax1-EGFP,Ds-Red,Sdc23 *drosophila*, Ptc-gal4>Vax1-EGFP,Ds-Red,Sdc *drosophila*, and Ptc-gal4>Vax1-EGFP,Ds-Red,Dlp *drosophilas* prepared by the same manner as described in Example <1-2> were fixed in 4% PFA/PBS for 30 minutes. To visualize the extracellular Vax1, those discs were reacted with the anti-Vax1 antibody diluted at the ratio of 1:10, at 4° C. for 10 minutes, followed by washing with PBS three times. Then, the discs were reacted with the Cy5-conjugated secondary antibody diluted at the ratio of 1:1000 at room temperature for 1 hour. Ptc-Gal4-induced green fluorescent signal and Ds-Red protein red fluorescent signal of the extracellular Vax1, EGFP, and Vax1-EGFP protein were visualized by using conforcal microscope (Olympus FV1000).

As a result, as shown in FIG. 8, the number of the cells expressing Vax1-EGFP in the front of the imaginal disc of the *drosophila* expressing Sdc mutant was increased, while the number of the cells expressing Vax1-EGFP in the front of the imaginal disc of the *drosophila* expressing Sdc (FIG. 8, line 3) and DlP (FIG. 8, line 4) was reduced. From the above results, it was confirmed that the syndecan (Sdc) over-expressed on the cell membrane of the *drosophila* imaginal disc was bound to the Vax1 protein co-expressed therein to interrupt the migration into the neighboring cells. Therefore, it was confirmed that the Vax1 protein migrated into the neighboring cells of the *drosophila* imaginal disc, like shown in the mammalian system, and the intercellular migration of Vax1 was mediated by heparan sulfate proteoglycans (HSPGs) (FIG. 8).

EXAMPLE 7

Heparan Sulfate Dependent Conjugation of Vax1 with Heparan Sulfate Proteoglycans <7-1> Conjugation of Vax1 with Heparan Sulfate Proteoglycans To investigate the role of syndecan in the migration of Vax1, immunoprecipitation and Western blotting were performed.

Particularly, the optic nerve obtained from the post-natal day 0 (P0) mouse was lysed in the lysis buffer containing 10 mM Tris-HCl (pH 7.4), 200 mM NaCl, 1% Triton X-100, and 1% NP-40. The cell lysate was centrifuged at 12,000×g for 10 minutes at 4° C. to obtain the supernatant. The obtained supernatant was treated with anti-Vax1 antibody and anti-Sdc2 antibodies (Santa Cruz Biotechnology), followed by reaction at 4° C. for 16 hours, to which protein A-agarose beads were added. For immuno-precipitation, the reaction mixture was further reacted at 4° C. for 16 hours. Then, the reaction mixture was washed with lysis buffer 5 times and the reaction was terminated by adding 2×SDS sample buffer. Western blotting was performed with the reaction mixture by using anti-Sdc2 antibody and anti-Vax1 antibody as the primary antibodies by the same manner as described in Example <3-1> (FIG. 9a). For the negative control, immuno-precipitation was performed by using rabbit IgG (rbIgG), followed by Western blotting by the same manner as described above.

The constructs encoding Vax1, Vax2, GFP-tagged Sdc1, and GFP-tagged Sdc2 were prepared. HEK293T cells were transfected with Vax1, GFP-Sdc1, or GFP-Sdc2 (FIG. 9b) or Vax2, GFP-Sdc1, or GFP-Sdc2 (FIG. 9c) by the same manner as described in Example <3-1>. 2 days later, the supernatant was obtained from the cell lysate prepared by the same manner as described above, followed by immuno-precipitation using anti-GFP antibody. Western blotting was performed with such primary antibody as anti-Vax1 (FIG. 9b) or anti-Vax2 antibody (FIG. 9c) by the same manner as described in Example <3-1> (FIGS. 9b and 9c).

As a result, as shown in FIGS. 9a-9c, Sdc2 was precipitated by Vax1 antibody in the E14.5 mouse optic nerve, while Vax1 was precipitated by Sdc2 (FIG. 9a). Also, Vax1 was precipitated by GFP antibody in HEK293T cells (FIG. 9b) but Vax2 was not precipitated (FIG. 9c). Therefore, it was confirmed that the Vax1 was interacted with not only the syndecan1 (Sdc1) and syndecan2 (Sdc2) over-expressed in HEK293T cells but also the syndecan2 existing in the E14.5 mouse optic nerve (FIGS. 9a~9c).

<7-2> Binding Site of Vax1 with Syndecan2

To identify the binding site of Vax1 with syndecan2 (Sdc2), immunoprecipitation and Western blotting were performed using N-terminal extracellular domain deficient Sdc2-C and C-terminal cytoplasmic domain deficient Sdc2-N.

Particularly, the construct encoding GFP-tagged Sdc2-N or Sdc2-C was prepared. HEK293T cells were transfected with Vax1 and the construct encoding GFP-Sdc2-N or Sdc2-C by the same manner as described in Example <3-1>. The supernatant was obtained from the cell lysate prepared by the same manner as described in Example <7-1>, followed by immunoprecipitation using anti-GFP antibody. Western blotting was performed with such primary antibody as anti-Vax1 by the same manner as described in Example <3-1> (FIG. 9d).

As a result, as shown in FIG. 9d, when GFP-Sdc2-N was over-expressed, Vax1 was precipitated by GFP antibody but when GFP-Sdc2-C was over-expressed, Vax1 was not precipitated by GFP antibody. Therefore, it was confirmed that the Vax1 was conjugated with the extracellular domain of Sdc (FIG. 9d).

<7-2> Vax1 Conjugated to the Side of Heparan Sulfate

The extracellular domain of Sdc is transformed by heparan sulfate sugar (Bishop et al., 2007). So, Vax1 can interact with not only the Sdc protein backbone but also the sugar group of the same. To investigate whether or not Vax1 could bind to the side chain of syndecan2 heparan sulfate (HS), immunoprecipitation was performed.

Particularly, the E14.5 mouse optic nerve was treated with 1 mg/ml of heparin (Acros Organics), followed by immunoprecipitation using anti-Vax1 antibody by the same manner as described in Example <7-1>. Then, Western blotting was performed using each antibody. For the negative control, immunoprecipitation was performed by using rabbit IgG (rbIgG), followed by Western blotting by the same manner as described above. As the primary antibodies, anti-Sdc2 antibody, anti-Sdc3 antibody (Santa Cruz Biotechnology), anti-Glp1 antibody (Santa Cruz Biotechnology), anti-Pax2 antibody (Invitrogen), and anti-Vax1 antibody (FIG. 9e) were used.

1 µg of Vax1-His protein was cultured with sepharose 4B resin coated with 0.2 mg/me of HS or CS (Chondroitin sulfate) at 4° C. for 1 hour. The Vax1 protein conjugated to the resin was treated with SDS sample buffer, followed by electrophoresis (10% SDS-PAGE) by the same manner as described in Example <3-1>. Then, Western blotting was performed by using anti-Vax1 antibody as the primary antibody. The relative intensity of Vax1 band was analyzed by using image-J software (FIG. 9f).

As a result, as shown in FIG. 9e, Sdc2, Sdc3, and Glp1were precipitated by Vax1 antibody in the absence of heparin, but they were not precipitated in the presence of heparin. From the above results, it was confirmed that the Vax1 competed with free heparin for heparan sulfate of heparan sulfate proteoglycans and also interacted with the heparan sulfate proteoglycans expressed in the retinal ganglion cell axon except the Pax2 forming a complex with Vax1 in optic stalk astrocyte precursor cells (FIG. 9e).

As shown in FIG. 9f, the recombinant Vax1 protein was conjugated to the resin coated with heparan sulfate, and accordingly the Vax1 was confirmed to bind to the side chain of heparan sulfate of the heparan sulfate proteoglycan protein expressed in the retinal ganglion cells (FIG. 9f). Therefore, the results of Example 7 confirmed that the Vax1 was specifically bound to the extracellular domain of heparan sulfate proteoglycans, particularly the side chain of heparan sulfate of the heparan sulfate proteoglycans.

EXAMPLE 8

Growth Stimulation of the Retinal Ganglion Cell Axon by the Interaction between Vax1 and Heparan Sulfate Proteoglycans <8-1> Growth Stimulation of the Retinal Ganglion Cell Axon by Vax1 Conjugated to Heparan Sulfate Proteoglycans To investigate the effect of the Vax1 conjugated to heparan sulfate proteoglycans on the growth of the retinal ganglion cell axon, and to investigate whether or not the growth stimulation of the retinal ganglion cell axon by Vax1 could be mediated by the Vax1 sugar binding motif displaying the homology with the motif of Otx2 as shown in Table 1 below, immunostaining was performed with the Vax1 KR-peptide or AA-bio peptide labeled with Vax1, heparinase I, chondroitinase ABC (ChnaseABC), and biotin, and the neural retina explant treated with Vax1 (KR/AA) His mutant protein.

Particularly, the neural retina explant prepared by the same manner as described in Example <1-1> was treated with 2.5 U/ml of heparinase I (Sigma) that could cut heparin and heparan sulfate sugar chain or 2.5 U/ml of chondroitinase ABC (ChnaseABC) (Sigma) capable of eliminating chondroitine sugar chain for 3 hours. 0.1 µg/ml of the Vax1-His recombinant protein was added thereto, followed by reaction for 24 hours. To investigate the presence of Vax1 in the retinal ganglion cell axon, immunostaining was performed using anti-Vax1 antibody (green) and anti-NF160 antibody (red), followed by visualization. The arrow indicates the enlarged area (scale bar: 500 µm) (FIG. 10a).

The length of the neural retina explant pre-cultured for 24 hours, prepared by the same manner as described in Example <1-1>, was measured by the same manner as described in Example <4-1>. The neural retina explant was treated with 0.1 µg/ml of the recombinant Vax1-His and the biotin labeled Vax1 KR-peptide (KR-bio; 100 ng/ml) encoding the amino acid sequence ranging from the $101^{st}$~$112^{th}$ residue displaying the homology with Otx2 sugar binding motif as shown in Table 1, Vax1-His (0.1 µg/ml) and AA-bio peptide (100 ng/ml) with the substitution of the two major sugar binding resides the $101^{st}$ lysine and the $102^{nd}$ arginine with alanine (Ala-Ala (AA)), or Vax1 (KR/AA)-His mutant protein (0.1 µg/ml) (AnyGen) with the substitution of Lys101-Arg102 (KR) with Ala-Ala (AA), followed by reaction for 24 hours. Then, the length of the axon was measured again by the same manner as described in Example <4-1>. The explant was fixed in 4% PFA/PBS, followed by immunostaining using anti-Vax1 antibody (green) and anti-NF160 antibody (red) by the same manner as described in Example <2-1> for the visualization (FIG. 10b). The arrow indicates the enlarged area (scale bar: 500 µm).

TABLE 1

| Sugar Binding Motif | Sequence |
|---|---|
| Otx2 | 44-RKQRRERTTFTR-55 (SEQ. ID. NO: 3) |
| Vax1 | 101-KRTRTSFTAEQL-112 (SEQ. ID. NO: 4) |

While the neural retina explants treated with heparinase I, chondroitinase ABC, KR-bio peptide, AA-bio peptide, and Vax1 (KR/AA) mutant protein were cultured for 24 hours, the changes in the length of the retinal ganglion cell axon were measured by the same manner as described in Example <4-1>, and the results are presented in a graph. The values were averaged and the error bar was analyzed by SD (Vax1 (n=7), Vax1+Heparinase 1 (n=6), Vax1+Chnase ABC n=6), Vax1+RK-bio (n=6), Vax1+AA-bio (n=6), Vax1 (KR/AA) (n=5)). P-value was calculated by student t-test (*, p<0.01; **, p<0.001) (FIG. 10c).

As a result, as shown in FIGS. 10a and 10c, the growth of the retinal ganglion cell axon was suppressed in the neural retina explant treated with heparinase I compared with the neural retina extract treated with chondroitinase ABC. The immunostaining signal of the axon was also reduced, suggesting that the heparan sulfate sugar chain of heparan sulfate proteoglycans was digested with heparinase I so that the Vax1 could not bind to heparan sulfate and resultingly the growth of the retinal ganglion cell axon was inhibited (FIGS. 10a and 10c).

As shown in FIGS. 10b and 10c, it was confirmed that the growth of the retinal ganglion cell axon was suppressed by the treatment of KR-bio peptide or Vax1 (KR/AA) mutant protein, while the growth continued when AA-bio peptide was treated similarly to when Vax1 alone was treated thereto (FIGS. 10b and 10c).

<8-2> Stimulation of the Retinal Ganglion Cell Axon Growth by the Conjugation of the Vax1 Sugar Binding Motif and Heparan Sulfate Proteoglycans To investigate the effect of Vax1 (KR/AA) mutant protein on the growth of the retinal ganglion cell axon, immunoprecipitation, Western blotting, and immunostaining were performed.

Particularly, the construct encoding V5-tagged Vax1 or Vax1 (KR/AA) was prepared, and HEK293T cells were transfected with the construct by the same manner as described in Example <3-1>, which were then treated with 10 mg/ml of heparin for 3 hours, followed by culture. The cells were lysed by the same manner as described in Example <3-1> and the growth medium was centrifuged to obtain supernatant (S3). The obtained supernatant was mixed with 3 M trichloroacetic acid (TCA, final concentration 20%) to precipitate the macromolecules. The precipitate was washed with cold acetone three times, which was then dried to obtain pellet. Western blotting was performed with the obtained cell lysate and the pellet using anti-V5 antibody (GenWay Biotech) as the primary antibody by the same manner as described in Example <2-1> (FIG. 11a, upper part). The relative intensity of Vax1 band was measured and presented in a graph by using image-J software (FIG. 11a, lower part).

HEK293T cells were transfected with the GFP-Sdc2, Myc-Vax1 or Myc-Vax1 (KR/AA) construct by the same manner as described in Example <3-1>. The cells were lysed by the same manner as described in Example <7-1> and the growth medium was centrifuged to obtain supernatant. Immunoprecipitation was performed with the supernatant using anti-Vax1 antibody. Then, Western blotting was performed using anti-GFP antibody as the primary antibody by the same manner as described in Example <3-1> (FIG. 11b).

HEK293T cells were transfected with the Myc-Vax1 or Myc-Vax1 (KR/AA) construct by the same manner as described in Example <3-1>. The supernatant of the cell culture fluid was obtained (S3), which was added to COS7 cells, followed by culture for 3 hours. The COS7 cells were immunostained with anti-Myc antibody (green, cell surface), anti-Vax1 antibody (red), and DAPI (blue), followed by visualization (scale bar: 20 μm) (FIG. 11c).

As a result, as shown in FIGS. 11a~11c, it was confirmed that the amount of Vax1 precipitated in the HEK293T cells treated with heparin was similar to that of Vax1 (KR/AA). However, the level of Vax1 (KR/AA) was higher than Vax1 in the heparin non-treated HEK293T cells (FIG. 11a). It was also confirmed that Vax1 (KR/AA) did not bind to Sdc2 (FIG. 11b); Vax1 (KR/AA) did not migrate into the cells (FIG. 11c); and the number of the retinal ganglion cell axon growing in the neural retina was reduced (FIG. 10c). It was also confirmed that the conjugation of Vax1 (KR/AA) mutant protein to heparan sulfate proteoglycans was less efficient than Vax1 did, resulting in the inhibition of the growth of the retinal ganglion cell axon (FIGS. 11a~11c, and FIG. 10c). Therefore, it was confirmed from the result of Example 8 that the conjugation of Vax1 to heparan sulfate proteoglycans was necessary for stimulating the growth of the retinal ganglion cell axon.

EXAMPLE 9

Intracellular Vax1 Invasion and the Growth of the Retinal Ganglion Cell Axon Stimulated by the Local Protein Synthesis <9-1> Confirmation of the Growth of the Retinal Ganglion Cell Axon Stimulated by the Intracellular Invasion of Vax1

It was confirmed from the results of Example 7 and Example 8 that the extracellular Vax1 could not only bind to heparan sulfate proteoglycans but also migrate into the cytoplasm of the retinal ganglion cell axon. Therefore, in order to investigate whether or not Vax1 could stimulate the growth of the retinal ganglion cell axon by regulating cytoplasmic response after invading in the cells or whether or not Vax1 could stimulate the growth of the retinal ganglion cell axon by activating the down stream signal of heparan sulfate proteoglycans, the present inventors constructed the Vax1 (WF/SR) mutant that was able to bind to heparan sulfate proteoglycans but could not invade into target cells. Then, immunoprecipitation and immunostaining were performed using the same.

Particularly, HEK293T cells were transfected with the Vax1 (WF/SR) mutant wherein the $147^{th}$ tryptophan (Trip) and the $148^{th}$ phenylalanine (Phe) residues, having the homology with the major residues involved in the cell-invasion of GFP-Sdc2 and antennapedia (Antp), were replaced with Ser-Arg (SR) or Vax1 by the same manner as described in Example <3-1>. Then, cell lysate was obtained from the same.

Immunoprecipitation was performed with the supernatant of the cell lysate by using anti-GFP antibody by the same manner as described in Example <7-1>, and Western blotting was performed with the same by using anti-Vax1 antibody as the primary antibody by the same manner as described in Example <3-1> (FIG. 12a).

COS 7 cells were added with the growth medium supernatant (S3) of HEK293T cells over-expressing Vax1 and vax1 (WF/SR) according to the method of Example <3-1>, followed by culture for 3 hours. The COS7 cells were immunostained with anti-Myc antibody (green), anti-Vax1 antibody (red), and DAPI (blue) by the same manner as described in Example <3-1>, followed by visualization (scale bar: 20 μm) (FIG. 12b).

COS7 cells were transfected with the Myc-Vax1 (WT) or Vax1 (WF/SR) mutant by the same manner as described in Example <3-1>. Then, the transfected COS7 cells were co-cultured with the neural retina explant obtained by the same manner as described in Example <1-1> for 48 hours, followed by immunostaining using anti-Vax1 antibody (green) and anti-NF160 antibody (red) by the same manner as described in Example <2-1> for the visualization (scale bar: 500 μm (upper part), 200 μm (lower part)) (FIG. 12c). The growth direction was measured (FIG. 12d).

As a result, as shown in FIGS. 12a and 12b, Vax1 and Vax1 (WF/SR) were all precipitated by anti-GFP antibody (FIG. 12a), but Vax2 (WF/SR) was not found in the cells (FIG. 12b). Therefore, it was confirmed that the Vax1 (WF/SR) mutant could bind to heparan sulfate proteoglycans but could not invade into target cells (FIGS. 12a and 12b).

As shown in FIGS. 12c and 12d, the growth of the retinal ganglion cell axon toward COS7 cells was suppressed in the neural retina explant co-cultured with the Vax1 (WR/SR) over-expressing COS7 cells. Therefore, it was confirmed that the invasion of extracellular Vax1 was necessary for the stimulation of the Vax1 induced growth of the retinal ganglion cell axon.

<9-2> Confirmation of Vax1 Protein Complex in Cytoplasm

To investigate the functions of Vax1 in cytoplasm, the GST-Vax1 protein complex was purified, followed by silver staining. Then, MALDI-TOF was performed to confirm the protein.

Particularly, the constructs encoding GST and GST-Vax1 were constructed. HEK293T cells were transfected with the constructs by the same manner as described in Example <3-1>. The HEK293T cells over-expressing GST and GST-Vax1 were lysed to obtain cell lysate. The obtained cell lysate was centrifuged at 4° C., 12,000×g for 10 minutes to obtain supernatant (S3). The supernatant was cultured with glutathione sepharose 4B resin at 4° C. for 1 hour. The mixture was then washed with lysis buffer 5 times, followed by elution with 2×SDS sample buffer. The eluted protein was electrophoresed, followed by silver-staining using a silver staining kit (Thermo) according to the manufacturer's protocol. The cells were lysed in PBS containing 0.1% SDS and 1% Triton X-100. The supernatant was obtained from the cell lysate, which was then cultured with resin. Then, the mixture was washed with high salt buffer (10 mM Tris-HCl (pH 7.4), 1 M NaCl, 1% Triton X-100, and 1% NP-40) and PBS twice. GST-conjugated protein was eluted by using PBS containing 10 mM glutathione. The obtained sample was electrophoresed (10% SDS-PAGE), followed by staining using Pierce Silver Stain Kit for Mass Spectrometry® (Pierce) according to the manufacturer's protocol. The stained bands were analyzed by MALDI-TOF mass spectrometry by Korea Basic Science Institute.

As a result, as shown in FIG. 13a, the major proteins separated by Vax1 affinity purification were identified as the ribosomal proteins (RPs) which were the ribosomal components, such as L11, L23A, L26, S14, and S16, and the translation regulators eIF (eukaryotic translation initiation factor) 3B and 3C, and HSPA1A (chaperon heat shock 70-KD protein 1A). Therefore, it was confirmed that the Vax1 protein was involved in the local protein synthesis, the similar mechanism of the regulation of the retinal ganglion cell axon growth by cytoplasmic En2 (Brunet et al., 2005; Yoon et al., 2012) (FIG. 13a).

<9-3> Acceleration of the Local Protein Synthesis by Vax1 Invaded in the Retinal Ganglion Cell Axon To investigate whether or not Vax1 was involved in the local protein synthesis, immunostaining was performed using Vax1 (WF/SR) mutant.

Particularly, the E13.5 mouse neural retina explant obtained by the same manner as described in Example <1-1> was cultured for 24 hours and then transferred in the medium containing Vax1 (WF/SR), followed by further culture for 24 hours. Then, the culture medium was replaced with methionine free medium. 30 minutes later, 50 μM of bioorthogonal noncanonical amino acid AHA (L-azidohomoalanine, Invitrogen) was added thereto. 6 hours later, the neural retina explant was washed with D-PBS containing 1% FBS, and added with 30 μM of DIBO-Alexa Fluore (Invitrogen) included in D-PBS containing 1% FBS, followed by culture at room temperature for 1 hour in a dark room. Then, the explant was washed with D-PBS containing 1% FBS 4 times, followed by culture in 4% PFA/D-PBS at room temperature for 15 minutes. The fluorescence in the protein containing AHA-Alexa488 was visualized and the protein synthesis in the retinal ganglion cell axon (FIG. 13b, line 2) and the cell body (FIG. 13b, line 3) was confirmed (scale bar: 500 μm (line 1), scale bar: 100 μm (line 3)) (FIG. 13b).

To investigate the effect of Vax1 on the nucleus in the course of the growth of the retinal ganglion cell axon mediated by Vax1, the neural retina explant was placed on the microscope and the axon was round cut with placing the cell body in the center by using a dissection knife. Finally, the axon was separated from the cell body by eliminating the cell body alone. 50 μM of AHA was added to the axon, followed by culture for 6 hours. The fluorescence in the protein containing AHA-Alexa488 was visualized and thereafter the protein synthesis rate was calculated (scale bar: 500 μm) (FIG. 13c). The length of the retinal ganglion cell axon growing for 6 hours was measured and presented in a graph by the same manner as described in Example <4-1>(**, p<0.001) (FIG. 13d).

As a result, as shown in FIG. 13a, when the WT recombinant Vax1 was expressed, the fluorescence intensity of the Alexa Fluor 488-labeled protein was significantly increased in the retinal ganglion cell axon (FIG. 13b, line 2). In the meantime, the invasion deficient Vax1 (WF/SR) mutant reduced the density of the newly synthesized protein in the retinal ganglion cell axon (FIG. 13b, line 3). Therefore, it was confirmed that the exogenous Vax1 invaded into the axon to stimulate the protein synthesis (FIG. 13b).

As shown in FIGS. 13c and 13d, the density of the synthesized protein was increased in the retinal axon separated from the cell body when the recombinant Vax1 was expressed (FIG. 13c, line 2). In the meantime, the density of the synthesized protein was just similar to that of the control when the Vax1 (WF/SR) mutant was expressed (FIG. 13c, line 3). In the retinal axon separated from the cell body, the growth of the axon was accelerated by Vax1 but the growth of the axon was suppressed in the retinal axon wherein the Vax1 (WF/SR) mutant was expressed (FIG. 13d). Therefore, it was confirmed from the results of Example 9 that the Vax1 migrated into cells and stimulated the local protein synthesis and as a result it could stimulate the growth of the retinal ganglion cell axon.

EXAMPLE 10

Regulation of the Retinal Ganglion Cell Axon Growth Toward the Midline by the Exogenous Vax1 Protein <10-1> Recovery of the Growth of the Retinal Ganglion Cell Axon Damaged by the Exogenous Vax1 Protein To investigate whether or not the growth of the retinal ganglion cell axon suppressed in the Vax1−/− mouse was recovered by the exogenous Vax1 protein, immunostaining was performed with the Vax1 recombinant protein and the Vax1 (WF/SR) recombinant protein.

Particularly, 0.1 μg/ml of 6X-His peptide and the collagen gel mixture comprising Vax1-His or Vax1 (WF/SR)-His protein were transplanted in the third ventricle of the Vax1lacZ/lacZ mouse embryo brain slap for 24 hours by the same manner as described in Example <4-2>. DiI surface fluorescence was visualized, followed by immunostaining with anti-Vax1 antibody (green) and anti-NF160 antibody (red) for the visualization (FIG. 14a-A). 1/Robo 1-Fc fragment (12.35 pmol, R&D Systems) and the collagen gel comprising 4.78/6X-His peptide (5.69 nmol) or 200/Vax1-His (5.69 nmol) protein were transplanted in the third ventricle of the Vax1lacZ/lacZ mouse embryo brain slab for 12 hours by the same manner as described in Example <4-2>, followed by visualization of the upper part fluorescence image using a photodetector. For the visualization of the lower part image, immunostaining was performed using anti-Vax1 antibody (green) and anti-NF160 antibody (red). The fluorescence intensity of the immunostained image was measured by using image-J software and presented in a graph. The expression intensity of the sample treated with rb-IgG was compared and the number on the graph indicates the number of the analyzed brain slab. The error bar was analyzed by SD. P-value was calculated by ANOVA **p<0.001) (FIG. 14a-B).

As a result, as shown in FIG. 14a, the approach and the growth of the retinal ganglion cell axon toward the ventral hypothalamus was not successful in the Vax1 knock out mouse embryo and the mouse transplanted with Vax1 (WF/SR) mutant protein. In the meantime, in the Vax1 knock out mouse embryo transplanted with the collagen gel comprising Vax1 protein, many retinal ganglion cell axons were observed in the ventral hypothalamus and the axon started re-growing therein (+Vax1-His). The transplantation of Vax1 and Vax1 (WF/SR) did not affect the deficiency of EphB3 in the medial diencephalon and the expression of Slit1 in the ventral lateral diencephalon. Therefore, it was confirmed that the Vax1 protein invaded in the axoplasm and stimulated the growth of the retinal ganglion cell axon regardless of the axon inducing molecule expression. It was also confirmed that the growth of the retinal ganglion cell axon in the ventral hypothalamus was more stimulated when the collagen gel mixture comprising Vax1-His and Robo 1-Fc was transplanted (FIG. 14a).

<10-2> Regulation of the Retinal Ganglion Cell Axon Growth by the Antagonism between the Exogenous Vax1 Protein and Slit2

The projection of the retinal ganglion cell axon in optic chiasm is often compared with the spinal commissural axonal projection heading for the floor plate (FP). The spinal commissural axon is prevented from entering the midline as immature and instead induced to growth toward the ventral direction by Slit1 expressed in the medial spinal cord. Likewise, Slit1 in the preoptic area (POA) and ventral latral diencephalon prevent the retinal ganglion cell axon from entering the brain. In the meantime, the spinal commissural axon recognizes the attractive signals such as netrin and Shh. The netrin and Shh attractive signals compete with the repulsive signal of Slit2 possibly accumulated locally by heparan sulfate proteoglycans (Matsumoto et al., 2007; Wright et al., 2012). However, neither netrin nor Shh are necessary for the induction of the retinal ganglion cell axon toward ventral hypothalamus (Deiner and Sretavan, 1999; Sanchez-Camacho and Bovolenta, 2008; data not shown). Therefore, to investigate the interrelation between Vax1 and Slit2, immunostaining was performed using Vax1 and slit2 protein and the length of the retinal ganglion cell axon was measured.

Particularly, the E13.5 mouse neural retina explant obtained by the same manner as described in Example <1-1> was cultured for 24 hours, to which 10 ng/ml of Slit2-His (R&D Systems) was treated along with 0 ng/ml (left), 10 ng/ml (middle), and 100 ng/me (right) of Vax1 (FIG. 14b-A, upper line). In the meantime, 10 ng/ml of Vax1-His was treated thereto along with 0 ng/ml (left), 10 ng/ml (middle), and 100 ng/ml (right) of Slit2-His (FIG. 14b-A, lower line). Then, visualization was performed (FIG. 14b-A). The length of the retinal ganglion cell axon changed in 24 hours was measured and presented in a graph by the same manner as described in Example <4-1>. The error bar was analyzed by SD and the number presented on the graph indicates the number of the analyzed axon (non-treated group (n=22), Vax1 (10 ng/ml) (n=10), Vax1 (100 ng/ml) (n=9), Slit2 (10 ng/ml) (n=5), Slit2 (100 ng/ml) (n=5), Vax1 (10 ng/ml)+Slit2 (10 ng/ml) (n=7), Vax1 (10 ng/ml)+Slit2 (100 ng/ml) (n=6), Vax1 (10 ng/ml)+Slit2 (10 ng/ml) (n=13), and Vax1 (100 ng/ml)+Slit2 (10 ng/ml) (n=7)) (FIG. 14b-B).

The E13.5 mouse neural retina explant and the Vax1-knock out ventral hypothalamic explant obtained by the same manner as described in Example <1-1> were co-cultured in the presence (FIG. 14c-A) or absence (FIG. 14c-B) of Robo 1-Fc (100 ng/ml) for 24 hours. Then, visualization was performed (left) or immunostaining was performed for the visualization (right) (scale bar: 500 µm) (FIG. 14c-A). The direction of the retinal ganglion cell axon growth was calculated by counting the immunostained image pixel of the axon marker NF160, and presented in a graph. + indicates the forward direction, 0 indicates the neutral, and − indicates the reverse direction. The error bar was analyzed by SD and the number of y axis of the graph indicates the number of the analyzed explants. P-value was calculated by ANOVA (p<0.01) (FIG. 14c-B).

The E13.5 mouse neural retina explant obtained by the same manner as described in Example <1-1> was cultured for 24 hours, to which 10 ng/ml of Slit2-His (R&D Systems) was treated along with 0 ng/ml (left), 10 ng/ml (middle), and 100 ng/ml (right) of Vax1 (FIG. 14b-A, lower line). In the meantime, 10 ng/me of Vax1-His was treated thereto along with 0 ng/me (left), 10 ng/ml (middle), and 100 ng/ml (right) of Slit2-His (FIG. 14b-A, lower line). Visualization was performed (FIG. 14b-A). The fluorescence intensity was presented in a graph using image J-software. The error bar was calculated by SD and the number presented on the graph indicates the number of the analyzed areas (scale bar: 20 µm) (FIG. 14d).

The neural retina explant obtained by the same manner as described in Example <1-1> was treated with Vax1-His (10 ng/ml), and Vax1-His (10 ng/ml) and Slit2-His (10 ng/ml), followed by visualization. Immunostaining was performed using anti-Vax1 antibody (green) and anti-His antibody (red) by the same manner as described in Example <2-1>, followed by visualization (scale bar: 500 µm (dark field), scale bar: 10 µm (dotted box)) (FIG. 14e).

The cortical explant was obtained by the same manner as described in Example <1-1>, to which Vax1, Vax1 (R152S), and Vax1 (WF/SR) were treated. Then, immunostaining was performed using anti-Vax1 antibody (green), anti-NF160 antibody (red), and DAPI (blue) by the same manner as described in Example <3-1>, followed by visualization (FIG. 14f).

As a result, as shown in FIG. 14b, the growth of the retinal ganglion cell axon was suppressed in the group co-treated with Vax1 and Slit2, compared with the group treated with Vax1 alone (Vax1 (10 ng/ml) and Slit non-treated image was compared with Vax1 (10 ng/ml) and Slit2 (10 ng/ml) image). On the contrary, in the group treated with both Slit2 and Vax1, the growth of the retinal ganglion cell axon was stimulated, compared with the group treated with Slit2 alone (Slit2 (10 ng/ml) and Vax1 non-treated image was compared with Slit2 (10 ng/ml) and vax1 (10 ng/ml) image) (FIG. 14b-A). Compared with the group treated with Vax1 alone, the group treated with both Vax1 and Slit2 displayed the decrease of the length of the axon (FIG. 14b-B). Therefore, it was confirmed that Vax1 competed with Slit2 and Vax1 had antagonism against the Slit2-induced retinal ganglion cell axon retraction response (FIG. 14b).

As shown in FIGS. 14c~14d, when Vax1 and Robo 1-Fc were treated together, the retinal ganglion cell axon growth was peculiarly stimulated (FIG. 14c) and Vax1 competition with Slit2 was once again confirmed (FIG. 14d).

As shown in FIG. 14e, Vax1 could invade in the retinal ganglion cell axon but Slit2 was arrested on the surface of the axon, suggesting that the reciprocal antagonism between Vax1 and Slit2 was not mediated by heparan sulfate proteoglycans (FIG. 14e).

As shown in FIG. 14f, when Vax1 and Vax1 (R152S) were co-treated, the growth of the axon was induced in the cortical explant, suggesting that the Vax1 protein could not only induce the growth of the retinal ganglion cell axon but also the growth of the cortical nerve axon. Therefore, it was confirmed that various nerve axon midline passes could be also regulated by Vax1 protein as the retinal ganglion cell axon was controlled by Vax1 protein (FIG. 14f).

<10-3> Growth Regulation Model of the Retinal Ganglion Cell Axon by the Secreted Vax1 Protein The function of Vax1 as the axon growth factor secreted in the ventral hypothalamus of the mammalian brain was confirmed from the results of Examples 2~9.

As shown in FIG. 14f, Vax1 is secreted in the radial glial cells of the ventral hypothalamus and neural progenitor cells (NPC) and then secreted extracellularly. The secreted Vax1 is located in the midline at a high concentration by forming density gradient and thus spreads wide to the side. Once Vax1 binds to heparan sulfate proteoglycans (HSPGs) including syndecan of the retinal ganglion cell axon approaching the ventral hypothalamus, the concentration of Vax1 is locally increased in the retinal ganglion cell growth region. Thereafter, Vax1 invades into the retinal ganglion cell axon to stimulate the protein synthesis so as to induce the growth of the axon toward the midline. Additionally, the retinal ganglion cell axon attracting factors rich in the midline of the ventral hypothalamus such as VEGF164-neurophilin and ephrinB2-EphB1 determine the growth direction of the retinal ganglion cell axon in the midline for the formation of optic chiasm. As a result, the growth regulation model of the retinal ganglion cell axon by Vax1 protein was completed.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

The invention claimed is:

1. A method for increasing axonal outgrowth of retinal ganglion neurons comprising administering to a subject a pharmaceutically effective dose of Vax protein to a subject having retinal ganglion damage, thereby increasing axonal outgrowth of retinal ganglion neurons in the subject, wherein the Vax protein is selected from the group consisting of a) Vax1 protein comprising the amino acid sequence of SEQ ID NO: 1 and b) Vax2 protein comprising the amino acid sequence of SEQ ID NO: 2.

2. The method for increasing axonal outgrowth of retinal ganglion neuron according to claim 1, wherein the Vax protein comprises the amino acid sequence of SEQ ID NO: 1.

3. The method for accelerating the growth of retinal ganglion cell axons according to claim 1, wherein the Vax protein comprises the amino acid sequence of SEQ ID NO: 2.

* * * * *